(12) United States Patent
Olefsky et al.

(10) Patent No.: US 8,987,332 B2
(45) Date of Patent: Mar. 24, 2015

(54) METHODS OF TREATING INFLAMMATORY CONDITIONS

(75) Inventors: Jerrold M. Olefsky, Solana Beach, CA (US); Da Young Oh, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 137 days.

(21) Appl. No.: 13/493,241

(22) Filed: Jun. 11, 2012

(65) Prior Publication Data

US 2012/0295975 A1 Nov. 22, 2012

Related U.S. Application Data

(63) Continuation of application No. PCT/US2010/059699, filed on Dec. 9, 2010.

(60) Provisional application No. 61/379,626, filed on Sep. 2, 2010, provisional application No. 61/377,601, filed on Aug. 27, 2010, provisional application No. 61/285,086, filed on Dec. 9, 2009.

(51) Int. Cl.
*A61K 31/20* (2006.01)
*A61K 31/202* (2006.01)

(52) U.S. Cl.
CPC ............... *A61K 31/20* (2013.01); *A61K 31/202* (2013.01)
USPC ........................................................ 514/558

(58) Field of Classification Search
CPC .................................................... A61K 31/202
USPC ........................................................ 514/558
See application file for complete search history.

(56) References Cited

U.S. PATENT DOCUMENTS

2006/0026702 A1 2/2006 Rockman et al.
2009/0274730 A1 11/2009 Watson et al.

FOREIGN PATENT DOCUMENTS

WO 2007/134613 A1 11/2007
WO 2008/074839 A2 6/2008

OTHER PUBLICATIONS

Lattin et al., 2007, "G-Protein-Coupled Receptor Expression, Function, and Signaling in Macrophages," Journal of Leukocyte Biology, 82:16-32.
Sangiovanni et al., 2005, "The Role of Omega-3 Long-Chain Polyunsaturated Fatty Acids in Health and Disease of the Retina," Progress in Retinal and Eye Research, 24:87-138.
Wang et al., 2009, "Fenoterol, a beta2-adrenoceptor Agonist, Inhibits LPS-Induced Membrane-Bound CD14, TLR4/CD14 Complex, and Inflammatory Cytokines Production Through Beta-Arrestin-2 in THP-1 Cell Line," Acta Pharmacologica Sinica, 30:1522-1528.
Zhang et al., 2005, "Beta-Arrestin1 and Beta-Arrestin2 are Differentially Required for Phosphorylation-Dependent and -Independent Internalization of Delta-Opioid Receptors," Journal of Neurochemistry, 95:169-178.
Acta Pharmalogica Sinica: Issues [online]; downloaded from: http:\\www.chinaphar.com/167-4083/2009.htm on Mar. 19, 2011; provided to verify the publication of Wang, above, in Nov. 2009.
PCT International Search Report for PCT/US2010/059699 mailed on Apr. 20, 2011 (2 pages).

*Primary Examiner* — Kevin E Weddington
(74) *Attorney, Agent, or Firm* — Sutherland Asbill & Brennan LLP

(57) ABSTRACT

The present invention provides methods of treating a β-arrestin2 mediated and/or GPR120 mediated response in a subject. The β-arrestin2 mediated and/or GPR120 mediated response can be inflammation, including diabetes, inflammation associated with obesity and obesity. The methods can comprise administering to a subject a therapeutically effective amount of a compound predicted to bind a β-arrestin2 molecule and/or GPR120, wherein the compound selectively activates a β-arrestin2-dependent signaling pathway of GPR120.

16 Claims, 29 Drawing Sheets

```
                        SEQUENCE LISTING

<160> NUMBER OF SEQ ID NOS: 50

<210> SEQ ID NO 1
<211> LENGTH: 21
<212> TYPE: RNA
<213> ORGANISM: Mus musculus

<400> SEQUENCE: 1
ggccuguggu guggauuauu u                                              21

<210> SEQ ID NO 2
<211> LENGTH: 23
<212> TYPE: RNA
<213> ORGANISM: Mus musculus

<400> SEQUENCE: 2
aaggaccgga aaguuucgu guu                                             23

<210> SEQ ID NO 3
<211> LENGTH: 20
<212> TYPE: DNA
<213> ORGANISM: Homo sapiens

<400> SEQUENCE: 3
gctattcctg gggtgtgtgt                                                20

<210> SEQ ID NO 4
<211> LENGTH: 20
<212> TYPE: DNA
<213> ORGANISM: Homo sapiens

<400> SEQUENCE: 4
ccctgtgatg agtcccaact                                                20

<210> SEQ ID NO 5
<211> LENGTH: 18
<212> TYPE: DNA
<213> ORGANISM: Homo sapiens

<400> SEQUENCE: 5
ctgctcctgc tcctcttc                                                  18

<210> SEQ ID NO 6
<211> LENGTH: 19
<212> TYPE: DNA
<213> ORGANISM: Homo sapiens

<400> SEQUENCE: 6
ccaggcgact gtagcagta                                                 19

<210> SEQ ID NO 7
<211> LENGTH: 19
```

-continued

```
<212> TYPE: DNA
<213> ORGANISM: Homo sapiens

<400> SEQUENCE: 7
ggctctacag cagcatcta                                                 19

<210> SEQ ID NO 8
<211> LENGTH: 20
<212> TYPE: DNA
<213> ORGANISM: Homo sapiens

<400> SEQUENCE: 8
aagcacacca ggaaattaag                                                20

<210> SEQ ID NO 9
<211> LENGTH: 20
<212> TYPE: DNA
<213> ORGANISM: Homo sapiens

<400> SEQUENCE: 9
tccaattctg tctccatcct                                                20

<210> SEQ ID NO 10
<211> LENGTH: 19
<212> TYPE: DNA
<213> ORGANISM: Homo sapiens

<400> SEQUENCE: 10
ctgactggct cagatgaaa                                                 19

<210> SEQ ID NO 11
<211> LENGTH: 20
<212> TYPE: DNA
<213> ORGANISM: Homo sapiens

<400> SEQUENCE: 11
ccatccctct agtgctcgtc                                                20

<210> SEQ ID NO 12
<211> LENGTH: 20
<212> TYPE: DNA
<213> ORGANISM: Homo sapiens

<400> SEQUENCE: 12
tgcggaagag tcggtagtct                                                20

<210> SEQ ID NO 13
<211> LENGTH: 22
<212> TYPE: DNA
<213> ORGANISM: Homo sapiens

<400> SEQUENCE: 13
atcagagagt tgaccgcagt tg                                             22

<210> SEQ ID NO 14
<211> LENGTH: 22
<212> TYPE: DNA
<213> ORGANISM: Homo sapiens

<400> SEQUENCE: 14
aatgaaccga agcacaccat ag                                             22

<210> SEQ ID NO 15
```

```
<211> LENGTH: 20
<212> TYPE: DNA
<213> ORGANISM: Homo sapiens

<400> SEQUENCE: 15
gccaccacgc tcttctgcct                                               20

<210> SEQ ID NO 16
<211> LENGTH: 20
<212> TYPE: DNA
<213> ORGANISM: Homo sapiens

<400> SEQUENCE: 16
ggctgatggt gtgggtgagg                                               20

<210> SEQ ID NO 17
<211> LENGTH: 23
<212> TYPE: DNA
<213> ORGANISM: Homo sapiens

<400> SEQUENCE: 17
ccagagatac aaagaaatga tgg                                           23

<210> SEQ ID NO 18
<211> LENGTH: 22
<212> TYPE: DNA
<213> ORGANISM: Homo sapiens

<400> SEQUENCE: 18
actccagaag accagaggaa at                                            22

<210> SEQ ID NO 19
<211> LENGTH: 20
<212> TYPE: DNA
<213> ORGANISM: Homo sapiens

<400> SEQUENCE: 19
tctggaccca ttccttcttg                                               20

<210> SEQ ID NO 20
<211> LENGTH: 20
<212> TYPE: DNA
<213> ORGANISM: Homo sapiens

<400> SEQUENCE: 20
aggtccctgt catgcttctg                                               20

<210> SEQ ID NO 21
<211> LENGTH: 20
<212> TYPE: DNA
<213> ORGANISM: Homo sapiens

<400> SEQUENCE: 21
aaatacctgt ggccttgggc                                               20

<210> SEQ ID NO 22
<211> LENGTH: 21
<212> TYPE: DNA
<213> ORGANISM: Homo sapiens

<400> SEQUENCE: 22
cttgggatcc acactctcca g                                             21
```

```
<210> SEQ ID NO 23
<211> LENGTH: 20
<212> TYPE: DNA
<213> ORGANISM: Homo sapiens

<400> SEQUENCE: 23
aatcttggag cgagttgtgg                                               20

<210> SEQ ID NO 24
<211> LENGTH: 21
<212> TYPE: DNA
<213> ORGANISM: Homo sapiens

<400> SEQUENCE: 24
caggaagtag gtgagggctt g                                             21

<210> SEQ ID NO 25
<211> LENGTH: 24
<212> TYPE: DNA
<213> ORGANISM: Homo sapiens

<400> SEQUENCE: 25
acgtcagtac aaggagatgt tgga                                          24

<210> SEQ ID NO 26
<211> LENGTH: 26
<212> TYPE: DNA
<213> ORGANISM: Homo sapiens

<400> SEQUENCE: 26
atcctattgc agaatgcttc tttacc                                        26

<210> SEQ ID NO 27
<211> LENGTH: 21
<212> TYPE: DNA
<213> ORGANISM: Homo sapiens

<400> SEQUENCE: 27
atggaagaga ccttcagcta c                                             21

<210> SEQ ID NO 28
<211> LENGTH: 21
<212> TYPE: DNA
<213> ORGANISM: Homo sapiens

<400> SEQUENCE: 28
gctgtcttcc caagagttgg g                                             21

<210> SEQ ID NO 29
<211> LENGTH: 20
<212> TYPE: DNA
<213> ORGANISM: Homo sapiens

<400> SEQUENCE: 29
catggcccag aaatcaagga                                               20

<210> SEQ ID NO 30
<211> LENGTH: 20
<212> TYPE: DNA
<213> ORGANISM: Homo sapiens

<400> SEQUENCE: 30
ggagaaatcg atgacagcgc                                               20
```

```
<210> SEQ ID NO 31
<211> LENGTH: 20
<212> TYPE: DNA
<213> ORGANISM: Homo sapiens

<400> SEQUENCE: 31
atgatgtctg ccagagaacc                                               20

<210> SEQ ID NO 32
<211> LENGTH: 22
<212> TYPE: DNA
<213> ORGANISM: Homo sapiens

<400> SEQUENCE: 32
atcacagatt tcagcaacct ta                                            22

<210> SEQ ID NO 33
<211> LENGTH: 20
<212> TYPE: DNA
<213> ORGANISM: Homo sapiens

<400> SEQUENCE: 33
gggcatacct ttatcctgag                                               20

<210> SEQ ID NO 34
<211> LENGTH: 20
<212> TYPE: DNA
<213> ORGANISM: Homo sapiens

<400> SEQUENCE: 34
ccactgaagt catccatgtc                                               20

<210> SEQ ID NO 35
<211> LENGTH: 23
<212> TYPE: DNA
<213> ORGANISM: Homo sapiens

<400> SEQUENCE: 35 aggttttct cagtcttgcc ttc                                            23

<210> SEQ ID NO 36
<211> LENGTH: 22
<212> TYPE: DNA
<213> ORGANISM: Homo sapiens

<400> SEQUENCE: 36
gggagcagtg tctcttactt cc                                            22

<210> SEQ ID NO 37
<211> LENGTH: 20
<212> TYPE: DNA
<213> ORGANISM: Homo sapiens

<400> SEQUENCE: 37
ctcgtggatc tccgtgacac                                               20

<210> SEQ ID NO 38
<211> LENGTH: 20
<212> TYPE: DNA
<213> ORGANISM: Homo sapiens

<400> SEQUENCE: 38
gcaaatggag ccgtctgtgc                                               20
```

<210> SEQ ID NO 39
<211> LENGTH: 20
<212> TYPE: DNA
<213> ORGANISM: Homo sapiens

<400> SEQUENCE: 39
gttgaaccag tctccgacca                                                   20

<210> SEQ ID NO 40
<211> LENGTH: 21
<212> TYPE: DNA
<213> ORGANISM: Homo sapiens

<400> SEQUENCE: 40
cgactcgcta tctccaagtg a                                                 21

<210> SEQ ID NO 41
<211> LENGTH: 21
<212> TYPE: DNA
<213> ORGANISM: Homo sapiens

<400> SEQUENCE: 41
ctgcataacg gtctggactt c                                                 21

<210> SEQ ID NO 42
<211> LENGTH: 19
<212> TYPE: DNA
<213> ORGANISM: Homo sapiens

<400> SEQUENCE: 42
cagcaactgc ccgtactcc                                                    19

<210> SEQ ID NO 43
<211> LENGTH: 21
<212> TYPE: DNA
<213> ORGANISM: Homo sapiens

<400> SEQUENCE: 43
ggaggtggtg atagccggta t                                                 21

<210> SEQ ID NO 44
<211> LENGTH: 21
<212> TYPE: DNA
<213> ORGANISM: Homo sapiens

<400> SEQUENCE: 44
tgggtaatcc atagagccca g                                                 21

<210> SEQ ID NO 45
<211> LENGTH: 22
<212> TYPE: DNA
<213> ORGANISM: Homo sapiens

<400> SEQUENCE: 45
taatgggctg cttctgtgac tc                                                22

<210> SEQ ID NO 46
<211> LENGTH: 22
<212> TYPE: DNA
<213> ORGANISM: Homo sapiens

<400> SEQUENCE: 46

```
ctcaatatcg ccatcagtct tg                                               22

<210> SEQ ID NO 47
<211> LENGTH: 20
<212> TYPE: DNA
<213> ORGANISM: Homo sapiens

<400> SEQUENCE: 47
gctctgctca ttgccatcag                                                  20

<210> SEQ ID NO 48
<211> LENGTH: 21
<212> TYPE: DNA
<213> ORGANISM: Homo sapiens

<400> SEQUENCE: 48
tgttgcagcc tctctacttg g                                                21

<210> SEQ ID NO 49
<211> LENGTH: 19
<212> TYPE: DNA
<213> ORGANISM: Homo sapiens

<400> SEQUENCE: 49
tcaccaccat ggagaaggc                                                   19

<210> SEQ ID NO 50
<211> LENGTH: 20
<212> TYPE: DNA
<213> ORGANISM: Homo sapiens

<400> SEQUENCE: 50
gctaagcagt tggtggtgca                                                  20
```

METHODS OF TREATING INFLAMMATORY CONDITIONS

CROSS REFERENCES TO RELATED APPLICATIONS

This patent application is a continuation of PCT Application No. PCT/US2010/059699 filed Dec. 9, 2010, which claims priority benefit of U.S. Provisional Application Ser. Nos. 61/285,086, 61/377,601, and 61/379,626 filed Dec. 9, 2010, Aug. 27, 2010, and Sep. 2, 2010, respectively, each of which is incorporated herein by reference in its entirety.

STATEMENT REGARDING FEDERALLY SPONSORED RESEARCH

This invention was made with government support under Grant Numbers 4 R37 DK 33651 and 1 P01 DK 074868 awarded by National Institute of Health/National Institute of Diabetes and Digestive and Kidney Diseases. The Government has certain rights in the invention.

REFERENCE TO SEQUENCE LISTING IDENTIFICATION

The Sequence Listing, which is a part of the present disclosure, includes a computer readable file "RUC_112WO_ST25.txt" generated by U.S. Patent & Trademark Office PatentIn version 3.5 software comprising nucleotide and/or amino acid sequences of the present invention. The subject matter of the Sequence Listing is incorporated herein by reference in its entirety.

FIELD OF THE INVENTION

The present teachings relate to methods of treating inflammatory conditions, including diabetes mellitus, by modulating β-arrestin2 and/or GPR120 mediated responses in a subject, as well as methods of screening compounds predicted to bind β-arrestin2 and/or GPR120.

BACKGROUND OF THE INVENTION

The traditional view of G protein-coupled receptors (GPCRs) has been that ligands, whether agonists or antagonists, affected both the G protein-dependent and β-arrestin-dependent pathways equally. Recently, however, it has been shown that the two pathways are pharmacologically separable. Certain ligands are capable of selectively activating one of the two pathways. These ligands are referred to as biased ligands, and the phenomenon is termed "biased agonism" or "ligand-directed signaling." To date, no compounds or methods for identifying compounds that selectively activate one of the two pathways have been provided. Therefore, what is needed in the art are such compounds that have biased effects for treating β-arrestin and/or GPCR mediated responses, as well as methods of screening for such compounds. In addition, methods of using such ligands to treat conditions associated with the G protein-dependent and/or β-arrestin-dependent pathways are needed.

SUMMARY OF THE INVENTION

The present teachings include methods of treating inflammation in a subject. In various embodiments, the method comprises administering a therapeutically effective amount of a compound that binds GPR120, the compound selectively activating a β-arrestin2-dependent signaling pathway of GPR120. In various aspects, the compound that selectively activates a β-arrestin2-dependent signaling pathway is an ω-3 fatty acid, including DHA and EPA. The compound can selectively activate a β-arrestin2-dependent signaling pathway and not activate a β-arrestin1-dependent signaling pathway. In various aspects, the inflammatory condition can be diabetes, an inflammatory condition is associated with obesity, and obesity. In various aspects, the subject is an animal, particularly a human.

A method is also provided of treating an inflammatory condition associated with β-arrestin2 function. In various embodiments, the method comprises administering a therapeutically effective amount of a β-arrestin2 modulating agent to a subject in need thereof. In various aspects, the inflammatory condition can be diabetes, an inflammatory condition is associated with obesity, and obesity. In various aspects, the compound that selectively activates a β-arrestin2-dependent signaling pathway is an ω-3 fatty acid, including DHA and EPA. The compound can selectively activate a β-arrestin2-dependent signaling pathway and not activate a β-arrestin1-dependent signaling pathway. In various aspects, the subject is an animal, particularly a human.

A method is also provided of treating an inflammatory condition associated with β-arrestin2 function and GPR120 function. In various embodiments, the method comprises administering a therapeutically effective amount of a β-arrestin2 modulating agent and a GPR120 modulating agent to a subject in need thereof. In various aspects, the inflammatory condition can be diabetes, an inflammatory condition is associated with obesity, and obesity. In various aspects, the compound that selectively activates a β-arrestin2-dependent signaling pathway is an ω-3 fatty acid, including DHA and EPA. The compound can selectively activate a β-arrestin2-dependent signaling pathway and not activate a β-arrestin1-dependent signaling pathway. In various aspects, the subject is an animal, particularly a human.

In addition, a method is provided of treating a β-arrestin2 mediated response. In various embodiments, the method comprises administering to a subject in need thereof a therapeutically effective amount of a compound predicted to bind GPR120, the compound selectively activating a β-arrestin2-dependent signaling pathway of said GPR120. In various aspects, the β-arrestin2 mediated response includes inflammation, including a lipopolysaccharide-induced inflammatory response and a TNFα-induced inflammatory response.

A method is also provided of inhibiting cytokine secretion. In various embodiments, the method comprising administering to a cell an effective amount of a compound predicted to bind GPR120, the compound selectively activating a β-arrestin2-dependent signaling pathway of GPR120. In various aspects, the β-arrestin2 mediated response includes inflammation, including a lipopolysaccharide-induced inflammatory response. In various aspects, the cytokine secretion inhibited is a lipopolysaccharide-induced cytokine secretion.

A method is also provided of screening a compound predicted to bind GPR120 for β-arrestin2 biased activity. In various embodiments, the method comprises (a) administering to a subject an amount of a compound predicted to bind GPR120 sufficient to generate a physiological response, (b) evaluating at a first time said physiological response, (c) administering to said subject an effective amount of a dsRNA capable of binding a β-arrestin2 RNA, (d) allowing a period of time to pass sufficient for said dsRNA to substantially bind said β-arrestin2 RNA, and (e) evaluating at a second time said physiological response, wherein if said physiological response is reversed at said second time as compared to said first time, said compound predicted to bind GPR120 is a β-arrestin2 biased compound. In various aspects, the physiological response relates to a lipopolysaccharide-induced inflammatory response. In various aspects, the physiological response relates to a TNF-α-induced inflammatory response. In various aspects, the physiological response relates to a lipopolysaccharide-induced cytokine secretion.

A kit is also provided. In various embodiments, the kit can comprise an effective amount of at least one dsRNA molecule capable of binding a β-arrestin2 RNA, and written indicia providing a user of said kit with instructions for using said kit in conjunction with the methods above. The kit can further comprise cells suitable for use in evaluating a compound predicted to bind GPR120, and provided in an amount sufficient for use in evaluating said GPR120 ligand. In various aspects, the cells can be mouse monocyte cells. In various aspects, the mouse monocyte cells are from cell line Raw264.7.

A dsRNA is also provided for inhibiting functional β-arrestin2 protein expression in a cell. In various embodiments, the dsRNA comprising a sense strand and an antisense strand, wherein said antisense strand comprises a region of complementarity having a sequence substantially complementary to a f-arrestin2 target sequence, wherein said sense strand is substantially complementary to said antisense strand, and wherein said dsRNA, upon contact with a cell expressing functional β-arrestin2 protein, inhibits functional β-arrestin2 protein expression. In various aspects, the β-arrestin2 target sequence comprises a sequence having SEQ ID NO. 2, or sequences complementary thereto.

In addition, a method is provided of inhibiting expression of a β-arrestin2 gene in a cell. In various embodiments, the method comprises introducing into the cell a dsRNA, wherein the dsRNA comprises two sequences that are complementary to each other and wherein a sense strand comprises a first sequence and an antisense strand comprises a second sequence comprising a region of complimentarity that is substantially complementary to at least a part of an mRNA encoding β-arrestin2. In various aspects, the dsRNA comprises a sequence selected having SEQ ID NO. 2, or sequences complementary thereto.

These and other features, aspects and advantages of the present teachings will become better understood with reference to the following description, examples and appended claims.

BRIEF DESCRIPTION OF DRAWINGS

Those of skill in the art will understand that the drawings, described below, are for illustrative purposes only. The drawings are not intended to limit the scope of the present teachings in any way.

DETAILED DESCRIPTION OF THE INVENTION

Abbreviations and Definitions

Figure 1A:
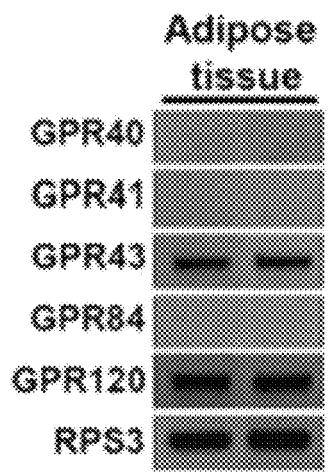
FIG. 1. Expression level of GPR120 and GPR120-mediated anti-inflammatory response in RAW 264.7 cells. (A) The mRNA expression pattern of various lipid sensing GPCRs is shown in adipose tissue, (B) CD11c+ bone marrow-derived dendritic cells (BMDCs), bone marrow-derived macrophages (BMDMs), IPMacs, 3T3-L1 preadipocytes, differentiated 3T3-L1 adipocytes, RAW 264.7 cells and L6 myocytes. Ribosomal protein S3 (RPS3) was used as internal control. (C) Expression of GPR120 in SVF, adipocytes and hepatic Kupffer cells from chow (NC)- or HFD-fed mice was examined by q-PCR. Data are expressed as the mean±SEM of at least three independent experiments in triplicate. *, $p<0.05$ versus NC. (D) RAW 264.7 cells, transfected with scrambled (Scr) or GPR120 #2 siRNA (GPR120 KD), were treated with 100 μM of GW9508 for 1 hr prior to LPS (100 ng/ml) treatment for 10 min and then subjected to western blotting. Left panel is a representative image from three independent experiments, and the scanned bar graph (right panel) shows fold induction over basal conditions. Knockdown efficiency of GPR120 siRNA is shown in FIG. 8. (E) Cytokine secretion level was measured in RAW 264.7 cells by ELISA. Data are expressed as the mean±SEM of three independent experiments. *, $p<0.05$ versus LPS treatment in scrambled siRNA transfected cells. See also FIGS. 8 and 9.

To facilitate understanding of the invention, a number of terms and abbreviations as used herein are defined below as follows:

"G," "C," "A," "T," and "U" (irrespective of whether written in capital or small letters) each generally stand for a nucleotide that contains guanine, cytosine, adenine, thymine, and uracil as a base, respectively. It will be understood, however, that the term "ribonucleotide" or "nucleotide" can also refer to a modified ribonucleotide, as further define below, or a surrogate replacement moiety. The skilled person is well aware that guanine, cytosine, adenine, thymine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequence of the invention by a nucleotide containing, for example, inosine. Sequences comprising such replacement moieties are embodiments of the invention.

Antisense Strand: As used herein, the term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus. Most preferably, the mismatches are located within 6, 5, 4, 3, or 2 nucleotides of the 5' terminus of the antisense strand and/or the 3' terminus of the sense strand.

Complementary: As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3, or 2 mismatched base pairs upon hybridization, while retaining the ability to hybridize under the conditions most relevant to their ultimate application. However, where two oligonucleotides are designed to form, upon hybridization, one or more single. stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from natural and modified nucleotides, in as far as the above requirements with respect to their ability to hybridize are fulfilled.

The terms "complementary," fully complementary," and "substantially complementary" herein may be used with respect to the base matching between the sense and antisense strand of a dsRNA, or between the antisense strand of a dsRNA and a target sequence, as will be understood from the context of their use.

Double-Stranded RNA or dsRNA: As used herein, the term "double-stranded RNA" or "dsRNA" refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop" and the entire structure is referred to as a "short hairpin RNA" or "shRNA." Where the two strands are connected covalently by means other than an uninterrupted chain, of nucleotides between the 3'-end of one strand and the 5'-end of the respective other strand forming the duplex structure, the connecting structure is referred to as the "linker." The RNA strands may have the same or a different number of nucleotides. The maximum number of base pairs is the number of nucleotides in the shortest strand of the dsRNA, minus any overhangs that are present in the duplex. In addition to the duplex structure, a dsRNA may comprise one or more nucleotide overhangs.

Nucleotide Overhang: As used herein, the term "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e. no nucleotide overhang. A "blunt ended" dsRNA is a dsRNA that has no nucleotide overhang at either end of the molecule.

Pharmaceutically Acceptable: As used herein, the term "pharmaceutically acceptable" means approved by a regulatory agency of the Federal or a state government or listed in the U.S. Pharmacopeia or other generally recognized pharmacopeia for use in animals, and more particularly in humans.

Pharmaceutically Acceptable Carrier: As used herein, the term "pharmaceutically acceptable carrier" refers to a diluent, adjuvant, excipient, or vehicle with which a compound is administered. Such carriers can be sterile liquids, such as water and oils, including those of petroleum, animal, vegetable, or synthetic origin, such as peanut oil, soybean oil, mineral oil, sesame oil and the like, polyethylene glycols, glycerine, propylene glycol, or other synthetic solvents. Water is a preferred carrier when a compound is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. A compound, if desired, can also combine minor amount of wetting or emulsifying agents, or pH buffering agents such as acetates, citrates, or phosphates. Antibacterial agents such as a benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compounds in combination with carriers are known to those of skill in the art.

Pharmaceutically Acceptable Salt: As used herein, the term "pharmaceutically acceptable salt" includes those salts of a pharmaceutically acceptable compound formed with free amino groups such as those derived from hydrochloric, phosphoric, acetic, oxalic, and tartaric acids, and those formed with free carboxyl groups such as those derived from sodium, potassium, ammonium, calcium, ferric hydroxides, isopropylamine, triethylamine, 2-ethylamino ethanol, histidine, and procaine. If the compound is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. Particularly preferred are besylate, hydrobromic, hydrochloric, phosphoric, and sulfuric acids. If the compound is acidic, salts may be prepared from pharmaceutically acceptable organic and inorganic bases. Suitable organic bases include, but are not limited to, lysine, N,N'-dibenzylethylenediamine, chloroprocaine, choline, diethanolamine, ethylene diamine, meglumine (N-methyl-glucamine) and procaine. Suitable inorganic bases include, but are not limited to, alkaline and earth-alkaline metals such as aluminum, calcium, lithium, magnesium, potassium, sodium, and zinc. Methods for synthesizing such salts are known to those of skill in the art.

Sense Strand: As used herein, the term "sense strand" refers to the strand of a dsRNA that includes a region that is substantially complementary to a region of the antisense strand.

Silence and Inhibit the Expression Of: As used herein, the terms "silence" and "inhibit the expression of," insofar as they refer to a β-arrestin gene, e.g. a β-arrestin2 gene, refer to at least the partial suppression of the expression of a β-arrestin gene as manifested by a reduction of the amount of mRNA transcribed from a β-arrestin gene which may be isolated from a first cell or group of cells in which a β-arrestin gene is transcribed and which has or have been treated such that the expression of a β-arrestin gene is inhibited, as compared to a second cell or group of cells substantially identical to the first cell or group of cells but which has or have not been so treated (control cells). The degree of inhibition is usually expressed in terms of $$\frac{(mRNA \text{ in control cells})}{(mRNA \text{ in control cells}) - (mRNA \text{ in treated cells})} \times 100$$

Alternatively, the degree of inhibition may be given in terms of a reduction of a parameter that is functionally linked to β-arrestin gene transcription, e.g. the amount of protein encoded by a β-arrestin gene which is secreted by a cell, or found in solution after lysis of such cells, or the number of cells displaying a certain phenotype, e.g. apoptosis or cell surface CF-TR. In principle, β-arrestin silencing may be determined in any cell expressing the target, either constitutively or by genomic engineering, and by any appropriate assay. However, when a reference is needed in order to determine whether a given dsRNA inhibits the expression of a β-arrestin gene by a certain degree and therefore is encompassed by the instant invention, the methods provided in the Examples below shall serve as such reference.

Strand Comprising a Sequence: As used herein, the term "strand comprising a sequence" refers to an oligonucleotide comprising a chain of nucleotides that is described by the sequence referred to using the standard nucleotide nomenclature.

Substantially Complementary: As used herein, a polynucleotide that is "substantially complementary" to at least part of a messenger RNA (mRNA) refers to a polynucleotide that is substantially complementary to a contiguous portion of the mRNA of interest. For example, a polynucleotide is complementary to at least part of a β-arrestin mRNA if the sequence is substantially complementary to a non-interrupted portion of an mRNA encoding β-arrestin.

Target Sequence: As used herein, "target sequence" refers to a contiguous portion of the nucleotide sequence of an mRNA molecule formed during the transcription of a β-arrestin gene, including mRNA that is a product of RNA processing of a primary transcription product. The target sequence of any given RNAi agent of the invention means an mRNA-sequence of X nucleotides that is targeted by the RNAi agent by virtue of the complementarity of the antisense strand of the RNAi agent to such sequence and to which the antisense strand may hybridize when brought into contact with the mRNA, wherein X is the number of nucleotides in the antisense strand plus the number of nucleotides in a single stranded overhang of the sense strand, if any.

Therapeutically Effective Amount: As used herein, the term "therapeutically effective amount" refers to those amounts that, when administered to a particular subject in view of the nature and severity of that subject's disease or condition, will have a desired therapeutic effect, e.g. an amount that will cure, prevent, inhibit, or at least partially arrest or partially prevent a target disease or condition.

Transformed Cell: As used herein, the term "transformed cell" is a cell into which a vector has been introduced from which a dsRNA molecule may be expressed.

Treatment: As used herein in the context of β-arrestin expression, the terms "treat", "treatment", and the like, refer to relief from or alleviation of pathological processes mediated by β-arrestin expression. In the context of the present invention insofar as it relates to any of the other conditions recited herein below (other than pathological processes mediated by β-arrestin expression), the terms "treat", "treatment", and the like mean to relieve or alleviate at least one symptom associated with such condition, or to slow or reverse the progression of such condition.

Treating Conditions Mediated by β-Arrestin2 and/or GPCR

The present invention provides methods of treating a 1-arrestin2 mediated and/or GPR120 mediated response in a subject. In one aspect of the invention, the β-arrestin mediated and/or GPCR mediated response is inflammation. The method can comprise administering to a subject in whom inflammation is to be treated a therapeutically effective amount of a compound predicted to bind a β-arrestin2 molecule and/or a G protein-coupled receptor, where the compound selectively activates a β-arrestin2-dependent signaling pathway of the GPCR. β-arrestin2 has a GenBank Gene ID No. 109689 and β-arrestin1 has a GenBank Gene ID No. 216869.

The invention further provides that GPR120, a GPCR contemplated in the invention and having GenBank Accession No. NP_859529, is expressed in proinflammatory macrophages and is induced in macrophages and Kupffer cells in obesity. DHA and EPA, major omega-3 FAs (ω-3 FAs) in fish oil, and GPR120 function as an ω-3 FA receptor/sensor. In vitro, ω-3 FAs exert robust and broad anti-inflammatory effects through GPR120 in macrophages. In vivo, an ω-3 FA supplemented diet exerts both anti-inflammatory and anti-diabetic/insulin sensitizing effects in obese mice, but is without effect in GPR120 KO mice. Hence, the invention provides methods for treating conditions associated with inflammation and insulin sensitization including, but not limited to, diabetes and obesity.

Treatment of Diseases and Disorders

Diseases and disorders that are characterized by β-arrestin2 and/or GPR120 biological activity (such as diabetes and other diseases and disorders associated with GPR120 expression) may be treated with therapeutics that agonize GPR120 activity. Agonists may be administered in a therapeutic or prophylactic manner. Therapeutics that may be used include omega-3 fatty acids, analogs thereof and derivatives thereof, and other modulators that alter the interaction between GPR120 and its binding partners. In addition to the agonists described herein, methods for screening for other agonists are provided herein, including in the Examples section. In various embodiments, the agonist can selectively activate β-arrestin2-dependent signaling pathway and not activate a β-arrestin1-dependent signaling pathway. In various embodiments, the agonist can selectively activate a β-arrestin2-dependent signaling pathway and not activate a G protein-dependent signaling pathway. Conversely, the agonist can selectively activate a G protein-dependent signaling pathway and not activate a β-arrestin2-dependent signaling pathway. Diseases and disorders that are characterized by decreased GPR120 levels or biological activity may be treated with therapeutics that increase (i.e., are agonists to) activity. Therapeutics that upregulate activity may be administered therapeutically or prophylactically.

Prophylactic Methods

The invention provides a method for preventing, in a subject, a disease or condition associated with an aberrant GPR120 activity by administering an agent that modulates GPR120 activity. In various aspects, aberrant activity includes inflammatory conditions, including diabetes, inflammatory condition is associated with obesity, and obesity.

Subjects at risk for a disease that is caused or contributed to by aberrant GPR120 expression or activity can be identified by, for example, an assay provided in the Examples section herein. Administration of a prophylactic agent can occur prior to the manifestation of symptoms characteristic of the GPR120 aberrancy, such that a disease or disorder is prevented or, alternatively, delayed in its progression. Depending on the type of GPR120 aberrancy, for example, a GPR120 agonist can be used to treat the subject. The appropriate agent can be determined based on screening assays. In various aspects throughout, the subject can be an animal, and in particular a human.

Therapeutic Methods

Another aspect of the invention pertains to methods of modulating β-arrestin2 and/or GPR120 biological activity for therapeutic purposes. The modulatory methods of the invention involve contacting a cell with an agent that modulates one or more of the activities of β-arrestin2 and/or GPR120 biological activity associated with the cell. An agent that modulates β-arrestin2 and/or GPCR biological activity can be a naturally occurring cognate ligand of GPR120 such as an omega-3 fatty acid, a peptide, a GPR120 and/or β-arrestin2 peptidomimetic, dsRNA, small molecule, and the like. Modulatory methods can be performed in vitro (e.g., by culturing the cell with the agent) or in vivo (e.g., by administering the agent to a subject). As such, the invention provides methods of treating an individual afflicted with a disease or disorder characterized by expression or activity of a β-arrestin and/or GPCR. In one embodiment, the method involves administering an agent (e.g., an agent identified by a screening assay), or combination of agents that modulates (e.g., up-regulates) β-arrestin2 and/or GPR120 biological activity.

In another aspect of the invention, the inflammation being treated by the method is a lipopolysaccharide ("LPS") induced inflammatory response. In a further aspect of the invention, the inflammation being treated by the method is a TNF-α-induced inflammatory response. In another aspect of the invention, the β-arrestin2 mediated response is cytokine secretion. Such cytokines include, but are not limited to TNF-α and interleukin-6. The method can comprise administering to a subject in whom cytokine secretion is sought to be inhibited a therapeutically effective amount of a compound predicted to bind GPR120, where the compound selectively activates a β-arrestin2-dependent signaling pathway of GPR120. In a further aspect of the invention, the cytokine secretion being inhibited is a lipopolysaccharide-induced cytokine secretion.

In still another aspect of the present invention, a method for screening compounds predicted to bind GPR120 in such a manner as to produce β-arrestin2 biased activity is provided. The method includes administering to a subject an amount of a compound predicted to bind a GPCR sufficient to generate a physiological response, evaluating that response, administering to the subject an effect amount of an siRNA capable of binding a β-arrestin2 RNA, allowing the binding to occur, and then evaluating the response once again. If the physiological response is reversed at the time of the second evaluation, then the compound being evaluated is a β-arrestin2 biased compound.

In still another aspect of the present invention, the method for screening described above is provided, wherein the physiological response evaluated is a lipopolysaccharide-induced inflammatory response or TNF-α-induced inflammatory response. In another aspect of the present invention, the method for screening described above is provided, wherein the physiological response is a lipopolysaccharide-induced cytokine secretion.

Agents that Modulate Functional β-arrestin and/or Functional GPCR

Various agents that modulate functional β-arrestin2 and/or functional GPR120 are contemplated by certain aspects of the present invention. Such agents are useful in treating conditions associated with β-arrestin2 function and/or GPR120 function. Such agents are also useful for screening for β-arrestin2 biased ligands or other compounds for GPCRs. These agents are useful in both in vivo and in vitro screening methods.

Agents that decrease levels of functional β-arrestin2 can target functional β-arrestin2 or nucleotides encoding therefor, resulting in a decrease in β-arrestin2 activity. The various classes of agents for use herein as agents that decrease levels of functional β-arrestin2 generally include, but are not limited to, RNA interference molecules, antibodies, small inorganic molecules, antisense oligonucleotides, and aptamers.

Agents that agonize functional GPCR, and specifically GPR120, can include the ω-3 FAs identified herein. Naturally occurring ω-3 FAs are well known in the art. In addition, modified ω-3 FAs can be made by methods known in the art. See, e.g., *Bailey's Industrial Oil and Fat Products*, Sixth Edition, Six Volume Set. Edited by Fereidoon Shahidi. John Wiley & Sons, Inc. (2005), incorporated herein by reference in its entirety. ω-3 FAs having a biological activity useful in performing the methods of the invention can be indentified by employing the methods described herein.

RNA interference (RNAi) can be used to decrease the levels of functional β-arrestin2. RNAi methods can utilize double-stranded RNAs, for example, small interfering RNAs (siRNA), short hairpin RNAs (shRNA), and micro RNAs (miRNA). The following discussion focuses on dsRNA generally, but one skilled in the art will recognize many approaches that are available for other RNAi molecules, such as shRNA and miRNA.

Several dsRNA molecule design programs using a variety of algorithms are known to the art (see e.g., Cenix algorithm, Ambion; BLOCK-iT™ RNAi Designer, Invitrogen; dsRNA Whitehead Institute Design Tools, Bioinformatics & Research Computing). Traits influential in defining optimal dsRNA sequences include G/C content at the termini of the dsRNAs, $T_m$ of specific internal domains of the dsRNA, dsRNA length, position of the target sequence within the CDS (coding region), and nucleotide content of the 3' overhangs.

Administration of dsRNA molecules specific for functional β-arrestin2, and/or other related molecules with similar functions, can effect the RNAi-mediated degradation of the target (β-arrestin2) mRNA. For example, a therapeutically effective amount of dsRNA specific for β-arrestin2 can be adminstered to patient in need thereof to treat a condition mediated by (3-arrestin2.

Generally, an effective amount of dsRNA molecule comprises an intercellular concentration at or near the site of misfolding from about 1 nanomolar (nM) to about 100 nM, preferably from about 2 nM to about 50 nM, more preferably from about 2.5 nM to about 10 nM. It is contemplated that greater or lesser amounts of dsRNA can be administered.

The dsRNA can be administered to the subject by any means suitable for delivering the RNAi molecules to the cells of interest. For example, dsRNA molecules can be administered by gene gun, electroporation, or by other suitable parenteral or enteral administration routes, such as intravitreous injection. RNAi molecules can also be administered locally (lung tissue) or systemically (circulatory system) via pulmonary delivery. RNAi molecules can be used in conjunction with a variety of delivery and targeting systems, as described in further detail below. For example, dsRNA can be encapsulated into targeted polymeric delivery systems designed to promote payload internalization.

The dsRNA can generally be targeted to any stretch of less than 30 contiguous nucleotides, generally about 19-25 contiguous nucleotides, in the functional β-arrestin2 mRNA target sequences. Exemplary siRNAs targeting β-arrestin 1 and 2 are provided in Table 1 and Table 2, below. Searches of the human genome database (BLAST) can be carried out to ensure that selected dsRNA sequence will not target other gene transcripts. Techniques for selecting target sequences for dsRNA are known in the art (see e.g., Reynolds et al. (2004) Nature Biotechnology 22(3), 326-330). Thus, the sense strand of the present dsRNA can comprise a nucleotide sequence identical to any contiguous stretch of about 19 to about 25 nucleotides in the target mRNA of functional β-arrestin2. Generally, a target sequence on the target mRNA can be selected from a given cDNA sequence corresponding to the target mRNA, preferably beginning 50 to 100 nt downstream. (i.e., in the 3' direction) from the start codon. The target sequence can, however, be located in the 5' or 3' untranslated regions, or in the region nearby the start codon.

TABLE 1

| Target | Sequence (5'-3') | SEQ ID NO: |
|---|---|---|
| Mouse β-arrestin1 | GGC CUG UGG UGU GGA UUA UUU | 1 |
| Mouse β-arrestin2 | AAG GAC CGG AAA GUG UUC GUG UU | 2 |

The dsRNA of the invention can comprise an RNA strand (the antisense strand) having a region which is less than 30 nucleotides in length, generally 19-25 nucleotides in length, and is substantially complementary to at least part of an mRNA transcript of a β-arrestin2 gene. Using cell-based and animal assays, very low dosages of these dsRNA can specifically and efficiently mediate RNAi, resulting in significant inhibition of expression of a β-arrestin2 gene. Thus, the methods and compositions of the invention comprising these dsRNAs are useful for screening compounds for selectively activating a β-arrestin2 pathway when binding a GPCR.

The following detailed description discloses how to make and use the dsRNA and compositions containing dsRNA to inhibit the expression of a β-arrestin2 gene. The pharmaceutical compositions of the invention comprise a dsRNA having an antisense strand comprising a region of complementarity which is less than 30 nucleotides in length, generally 19-25 nucleotides in length, and is substantially complementary to at least part of an RNA transcript of a β-arrestin2 gene, together with a pharmaceutically acceptable carrier. These pharmaceutical compositions are useful in administering the dsRNA to an animal for use in animal models for screening compounds that can selectively activate a β-arrestin2 pathway when binding a GPCR.

Accordingly, certain aspects of the invention provide pharmaceutical compositions comprising the dsRNA of the invention together with a pharmaceutically acceptable carrier, as well as methods of using the compositions to inhibit expression of a β-arrestin2 gene.

On aspect of the invention provides dsRNA molecules for inhibiting the expression of a β-arrestin2 gene in a cell or mammal, wherein the dsRNA comprises an antisense strand comprising a region of complementarity that is complementary to at least a part of an mRNA formed in the expression of a β-arrestin2 gene, and wherein the region of complementarity is less than 30 nucleotides in length, generally 19-25 nucleotides in length.

Preferably, the dsRNA has at least 5, at least 10, at least 15, at least 18, or at least contiguous nucleotides per strand in common with at least one strand, but preferably both strands, of one of the dsRNAs shown in Tables 1 and 2. Alternative dsRNAs that target elsewhere in the target sequence of one of the dsRNAs provided in Tables 1 and 2 can readily be determined using the target sequence and the flanking β-arrestin2 sequence.

The dsRNA comprises two RNA strands that are complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of a β-arrestin2 gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s). For example, deoxyribonucleotide sequence "tt" or ribonucleotide sequence "UU" can be connected to the 3'-end of both sense and antisense strands to form overhangs. The dsRNA can be synthesized by standard methods known in the art as further discussed below, e.g., by use of an automated DNA synthesizer, such as are commercially available from, for example, Biosearch, Applied Biosystems, Inc.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well.

The dsRNA of the invention can contain one or more mismatches to the target sequence. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity, and preferably from the 5'-end. For example, for a 23 nucleotide dsRNA strand which is complementary to a region of a β-arrestin2 gene, the dsRNA generally does not contain any mismatch within the central 13 nucleotides. The methods described within the invention can be used to determine whether a dsRNA containing a mismatch to a target sequence is effective in inhibiting the expression of a β-arrestin2 gene. Consideration of the efficacy of dsRNAs with mismatches in inhibiting expression of a β-arrestin2 gene is important, especially if the particular region of complementarity in a β-arrestin2 gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of preferred dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference.

Preferred modified dsRNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other preferred dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are dsRNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$.] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$$OCH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

Other preferred modifications include 2'-methoxy (2'-$OCH_3$), 2'-aminopropoxy (2'-$OCH_2CH_2$ $CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

dsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687, 808, those disclosed in The Concise Encyclopedia Of Polymer Science And Engineering, pages 858-859, Kroschwitz, J. L., ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-5-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within a dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of a dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al. FEBS Lett., 1990, 259:327; Svinarchuk et al., Biochimie, 1993, 75:49), a phospholipid, e.g., di-hexadecyl-rac-glycerol or tri-ethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Therefore, what is provided in another aspect of the invention, a dsRNA is provided for inhibiting functional β-arrestin protein expression in a cell, the dsRNA having a sense strand and an antisense strand. The antisense strand includes a region of complementarity having a sequence substantially complementary to a β-arrestin target sequence. The sense strand is substantially complementary to said antisense strand. Further, the dsRNA, upon contact with a cell expressing functional β-arrestin protein, inhibits functional β-arrestin protein expression.

In still another aspect of the present invention, a β-arrestin target sequence includes a sequence selected from the group consisting of SEQ ID NO. 1 and SEQ ID NO. 2 or sequences complementary thereto.

Another aspect of the present invention provides a method for inhibiting expression of a β-arrestin gene in a cell. The method includes introducing into the cell a dsRNA having two sequences that are complementary to each other. A sense strand includes a first sequence and an antisense strand includes a second sequence having a region of complimentarity that is substantially complementary to at least a part of an mRNA encoding β-arrestin.

In another aspect of the invention, a method for inhibiting β-arrestin expression is provided, where the dsRNA used includes a sequence selected from the group consisting of SEQ ID NO. 1 and SEQ ID NO. 2, or sequences complementary thereto.

Vector Encoded RNAi Agents

The dsRNA of the invention can also be expressed from recombinant viral vectors intracellularly in vivo. The recombinant viral vectors of the invention comprise sequences encoding the dsRNA of the invention and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the dsRNA in a particular tissue or in a particular intracellular environment. The use of recombinant viral vectors to deliver dsRNA of the invention to cells in vivo is discussed in more detail below.

dsRNA of the invention can be expressed from a recombinant viral vector either as two separate, complementary RNA molecules, or as a single RNA molecule with two complementary regions.

Any viral vector capable of accepting the coding sequences for the dsRNA molecule(s) to be expressed can be used, for example vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20: 1006-1010.

Suitable AAV vectors for expressing the dsRNA of the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Non-dsRNA AGENTS

Antibodies can be used to decrease levels of functional β-arrestin2. Antibodies within the scope of the invention include, for example, polyclonal antibodies, monoclonal antibodies, antibody fragments, and antibody-based fusion molecules. Engineering, production, screening, purification, fragmentation, and therapeutic use of antibodies are well known in the art (see generally, Carter (2006) Nat Rev Immunol. 6(5), 343-357; Coligan (2005) Short Protocols in Immunology, John Wiley & Sons, ISBN 0471715786); Teillaud (2005) Expert Opin Biol Ther. 5(Supp. 1) S15-27; Subramanian, ed. (2004) Antibodies: Volume 1: Production and Purification, Springer, ISBN 0306482452; Brent et al., ed. (2003) Current Protocols in Molecular Biology, John Wiley & Sons Inc, ISBN 047150338X; Lo, ed. (2003) Antibody Engineering Methods and Protocols, Humana Press, ISBN 1588290921; Ausubel et al., ed. (2002) Short Protocols in Molecular Biology 5th Ed., Current Protocols, ISBN 0471250929). Various types of antibodies specific for functional β-arrestin2 can also be obtained from a variety of commercial sources. Antibodies can be altered or selected so as to achieve efficient antibody internalization. As such, the antibodies can more effectively interact with target intracellular molecules, such as functional β-arrestin2. Further, antibody-drug conjugates can increase the efficiency of antibody internalization. Efficient antibody internalization can be desirable for delivering functional β-arrestin2 specific antibodies to the intracellular environment for screening ligands or compounds predicted to bind GPCRs for selective activation of β-arrestin2 pathways. Conjugation of antibodies to a variety of agents that can facilitate cellular internalization of antibodies is known in the art (see generally Wu et al. (2005) Nat Biotechnol. 23(9), 1137-1146; McCarron et al. (2005) Mol Interv 5(6), 368-380; Niemeyer (2004) Bioconjugation Protocols, Strategies and Methods, Humana Press, ISBN 1588290980; Hermanson (1996) Bioconjugate Techniques, Academic Press, ISBN 0123423368).

Purified aptamers that specifically recognize and bind to functional β-arrestin2 nucleotides or proteins can be used to decrease the level of functional β-arrestin2. Aptamers are nucleic acids or peptide molecules selected from a large random sequence pool to bind to specific target molecule. The small size of aptamers makes them easier to synthesize and chemically modify and enables them to access epitopes that otherwise might be blocked or hidden. And aptamers are generally nontoxic and weak antigens because of their close resemblance to endogenous molecules. Generation, selection, and delivery of aptamers is within the skill of the art (see e.g., Lee et al. (2006) Curr Opin Chem Biol. 10, 1-8; Yan et al. (2005) Front Biosci 10, 1802-1827; Hoppe-Seyler and Butz (2000) J Mol Med. 78(8), 426-430). Negative selection procedures can yield aptamers that can finely discriminate between molecular variants. Aptamers can also be used to temporally and spatially regulate protein function (e.g., functional β-arrestin2 function) in cells and organisms. For example, the ligand-regulated peptide (LiRP) system provides a general method where the binding activity of intracellular peptides is controlled by a peptide aptamer in turn regulated by a cell-permeable small molecule (see e.g., Binkowski (2005) Chem & Biol. 12(7), 847-55). Using LiRP or a similar delivery system, the binding activity of functional β-arrestin2 could be controlled by a cell-permeable small molecule that interacts with the introduced intracellular functional β-arrestin2-specific protein aptamer. Thus, aptamers can provide an effective means to decrease functional β-arrestin2 levels by, for example, directly binding the functional β-arrestin2 mRNA and/or functional β-arrestin2 expressed protein.

Purified antisense nucleic acids that specifically recognize and bind to ribonucleotides encoding functional β-arrestin2 can be used to decrease the levels of functional 1-arrestin2. Antisense nucleic acid molecules within the invention are those that specifically hybridize (e.g., bind) under cellular conditions to cellular mRNA and/or genomic DNA encoding, for example functional β-arrestin2 protein, in a manner that inhibits expression of that protein, e.g., by inhibiting transcription and/or translation. Antisense molecules, effective for decreasing functional β-arrestin2 levels, can be designed, produced, and administered by methods commonly known to the art (see e.g., Chan et al. (2006) Clinical and Experimental Pharmacology and Physiology 33(5-6), 533-540).

Ribozyme molecules designed to catalytically cleave target mRNA transcripts can also be used to decrease levels of functional β-arrestin2. Ribozyme molecules specific for functional β-arrestin2 can be designed, produced, and administered by methods commonly known to the art (see e.g., Fanning and Symonds (2006) Handbook Experimental Pharmacology 173, 289-303G, reviewing therapeutic use of hammerhead ribozymes and small hairpin RNA). Triplex-forming oligonucleotides can also be used to decrease levels of related molecules with similar activity (see generally, Rogers et al. (2005) Current Medicinal Chemistry 5(4), 319-326).

Administration

In aspects of the present invention wherein dsRNAs or other compounds for inhibiting functional β-arrestin2 are used in animal models, these dsRNAs or other compounds must be effectively administered to the animals in question. Any suitable methods of administration may be used, and it is understood that many such methods of administration will be readily apparent to those of skill in the art upon reading this disclosure.

Screening

As noted above, another aspect of the invention is directed to a system for screening candidate agents predicted to bind GPCRs for selective activation of functional β-arrestin2 expression. Assays can be performed on living mammalian cells, which more closely approximate the effects of a particular serum level of drug in the body. Studies using extracts offer the possibility of a more rigorous determination of direct agent/enzyme interactions. Exemplary screening methods are detailed in the examples, below.

In one aspect of the present invention, screening is accomplished by administering to a subject an amount of a compound predicted to bind a GPCR sufficient to generate a physiological response, evaluating that response, administering to the subject an effect amount of a dsRNA (such as, for example, a siRNA) capable of binding a β-arrestin2 RNA, allowing the binding to occur, and then evaluating the response once again. If the physiological response is reversed at the time of the second evaluation, then the compound being evaluated is a β-arrestin2 biased compound. The physiological response can be any response mediated by β-arrestin2. For some responses, a reversal may include an increase of an observed physiological response, while with respect to other responses a reversal may include a decrease of an observed physiological response. The physiological response may, for example, relate to a LPS-induced or TNF-α-induced inflammatory response, or may relate to a LPS-induced cytokine secretion. As used herein, the phrase "relate to" with respect to a physiological response can refer to an increase in the measured physiological response, a decrease in the measured physiological response, or any other measurable variation in the physiological response.

Kits

Various embodiments of the present invention include kits. Such kits can include a compound of the present invention, optionally one or more ingredients for preparing a pharmaceutically acceptable formulation of the compound, and instructions for use (e.g., administration). When supplied as a kit, different components of a compound formulation can be packaged in separate containers and admixed immediately before use. Such packaging of the components separately can, if desired, be presented in a pack or dispenser device which may contain one or more unit dosage forms containing the compound. The pack may, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

Kits may include reagents in separate containers such as, for example, sterile water or saline to be added to a lyophilized active component packaged separately. For example, sealed glass ampules may contain lyophilized superoxide dismutase mimetics and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, videotape, audio tape, and the like. Detailed instructions may not be physically associated with the kit; instead, a user may be directed to an Internet web site specified by the manufacturer or distributor of the kit, or supplied as electronic mail.

In another aspect of the present invention, a kit is provided. The kit includes an effective amount of at least one siRNA molecule capable of binding a β-arrestin RNA, and written indicia providing a user of the kit with instructions for using the kit in accordance with one of the methods described herein. In still another aspect of the present invention, the kit further includes cells suitable for use in evaluating a compound predicted to bind a GPCR in an amount sufficient to evaluate the compound. In another aspect of the present invention, the cells provided in the kit are mouse monocyte cells. In still another aspect of the present invention, the mouse monocyte cells provided are from the cell line Raw 264.7.

EXAMPLES

Example 1

GPR120, Inflammation, Diabetes and Obesity
GPR120 Expression

Figure 1B:
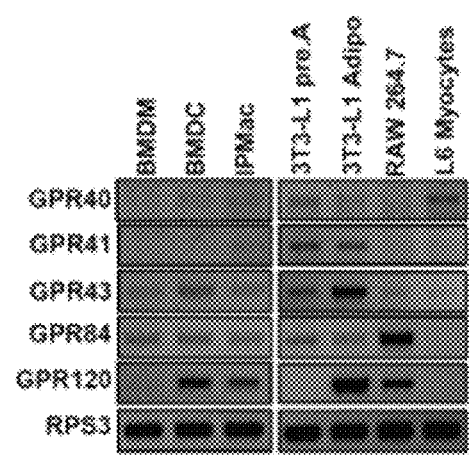
Figure 1C:
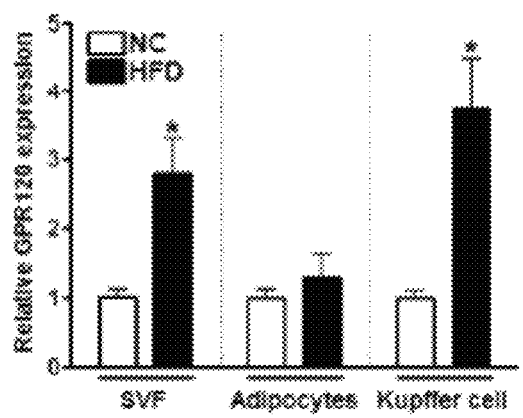

Fatty acids (FAs) can function as endogenous ligands modulating inflammatory responses, but not all FAs work in the same way. In general, saturated FAs (SFAs) are pro-inflammatory, unsaturated FAs are weakly pro-inflammatory or neutral, and ω3-FAs can be anti-inflammatory (Lee et al., 2003; Calder, 2005; Solinas et al., 2007). Because of the importance of inflammation in a number of chronic human diseases including insulin resistance, obesity, and type 2 diabetes mellitus, we surveyed the family of FA sensing GPCRs (GPR40, 41, 43, 84, and 120). Based on its tissue expression pattern, GPR120 emerged as a receptor of particular interest. As seen in FIG. 1, GPR120 is the only lipid sensing GPCR which is highly expressed in adipose tissue, pro-inflammatory CD11c+ macrophages (BMDCs), mature adipocytes, and monocytic RAW 264.7 cells (FIGS. 1A and 1B). GPR120 is induced in the stromal vascular fraction (SVF) of adipose tissue (which contains the macrophages), as well as in hepatic Kupffer cells, during high fat diet (HFD) feeding in mice (FIG. 1C). GPR120 is also expressed in enteroendocrine L cells with negligible expression in muscle (FIG. 11C), hepatocytes or other cell types (Hirasawa et al., 2005, Gotoh et al., 2007).

Ligand Stimulated GPR120 Exerts Anti-Inflammatory Effects

Figure 1D:
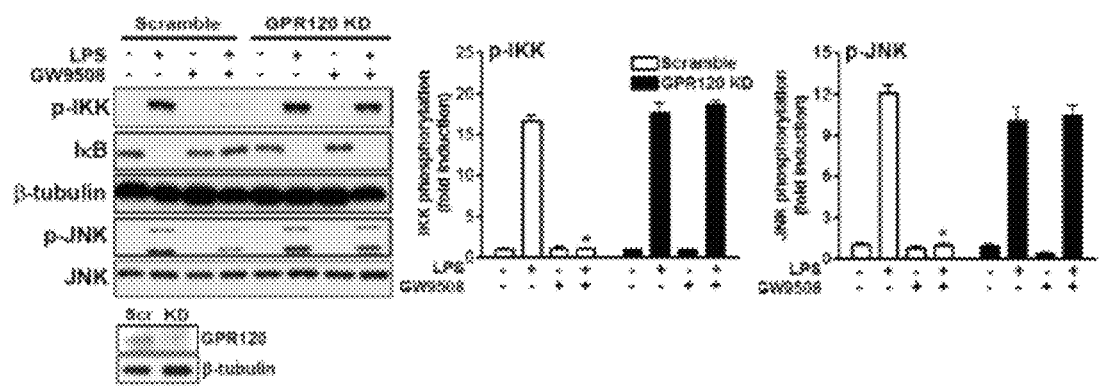
Figure 1E:
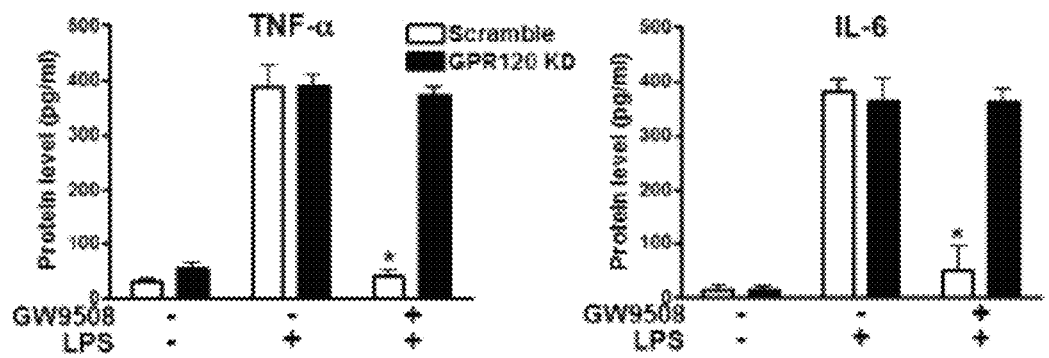
Figure 5A:
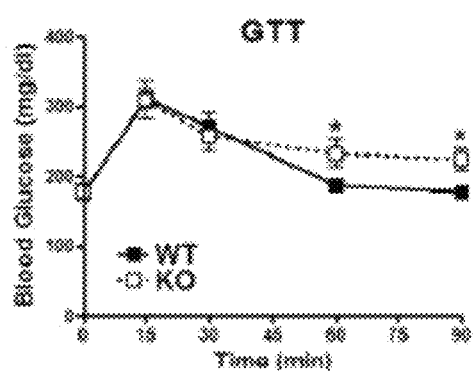
FIG. 5. In vivo metabolic studies in GPR120 KO mice. (A) GTT in NC-fed WT and GPR120 KO mice. n=7 per group. (B) insulin concentration were measured at the indicated time points and (C) area-under-curve analysis of the insulin data shows a significant difference between WT and GPR120 KO mice on NC. (D) Hyperinsulinemic/euglycemic clamp studies in chow-fed WT and GPR120 KO mice on. (E) Clamp studies in HFD, ω-3 FA supplemented (+ω3), and Rosiglitazone treated HFD mice (+Rosi). n=8 per group, *, $p<0.05$ compared to HFD-fed WT group. (F) mean±SEM plasma concentration (mole (%)) of DHA and EPA for each diet in WT and GPR120 KO mice. n=7 per each group. *, $p<0.05$, compared to NC, and **, $p<0.05$ compared to HFD. Data are represented as mean±SEM. See also FIGS. 11, 12, 13 and Table 2.
Figure 5B:
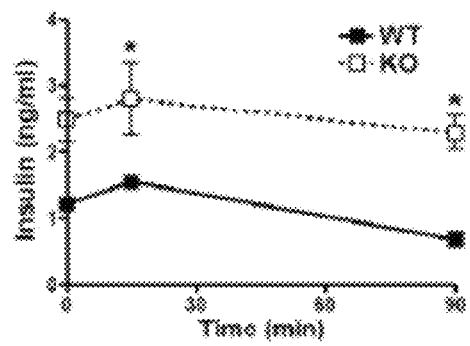
Figure 5C:
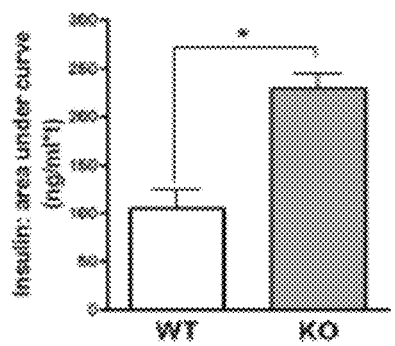
Figure 5D:
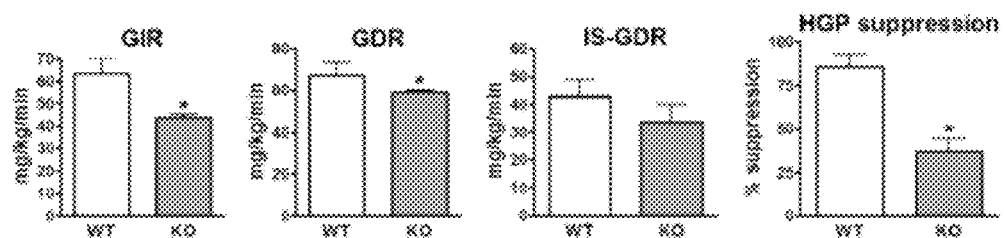
Figure 5E:
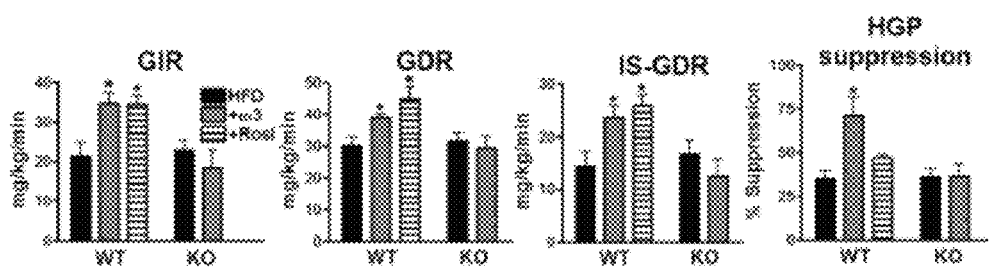
Figure 5F:
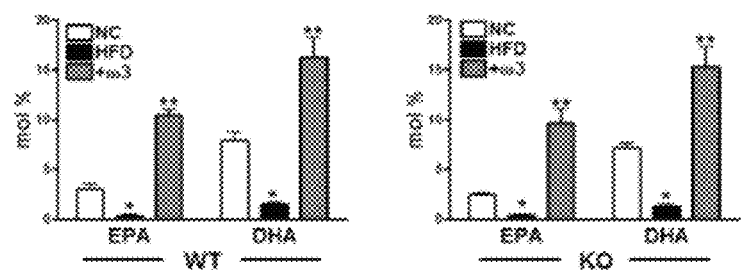
Figure 8A:
FIG. 8, related to FIG. 1. Validation of GPR120 siRNA knockdown efficiency. (A) Relative gene expression level of GPR120 and GPR40 in IPMac, RAW 264.7 cells, and 3T3-L1 adipocytes by q-PCR. (B) SiRNA transfection did not lead to an increase of IFN-γ expression. Four different sequences of GPR120 siRNA were electroporated into RAW 264.7 cells (C) and 3T3-L1 adipocytes (D). Knockdown efficiencies and specificity of siRNA knockdown by RT-PCR (gel image, left panel) and q-PCR (bar graph, right panel). SiRNA #2 showed >90% inhibition of GPR1120 mRNA expression without off-target effects on other fatty acid responsive GPCRs in both cell types. (E) The #2 GPR120 siRNA effectively inhibited GPR120 protein expression in RAW 264.7 cells. The scanned bar graph (right panel) shows % inhibition over scrambled siRNA (Scr) electroporation. Data are expressed as the mean±SEM of three independent experiments. *, $p<0.05$. (F) To rule out off-target effects of the siRNA, other GPR120 siRNAs were tested for their effects on GPR120 activation. All GPR120 siRNAs reversed GPR120-mediated-anti-inflammation. Therefore, #2 GPR120 siRNA was used for the entire study.
Figure 8B:
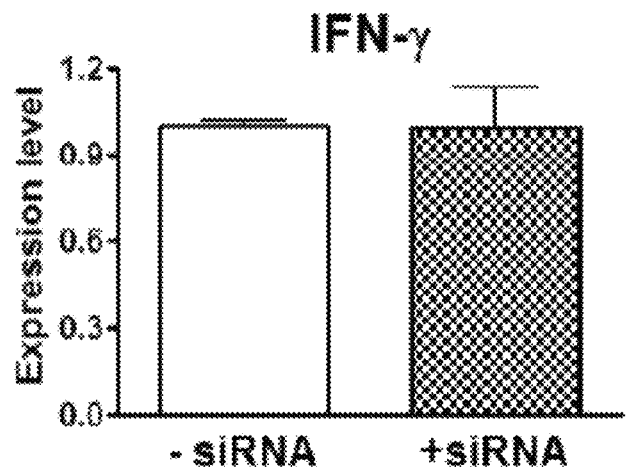
Figure 8C:
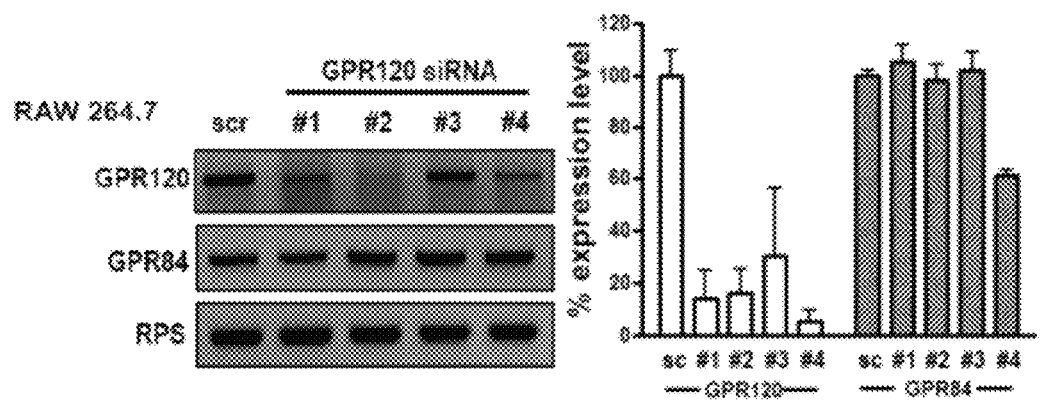
Figure 8D:
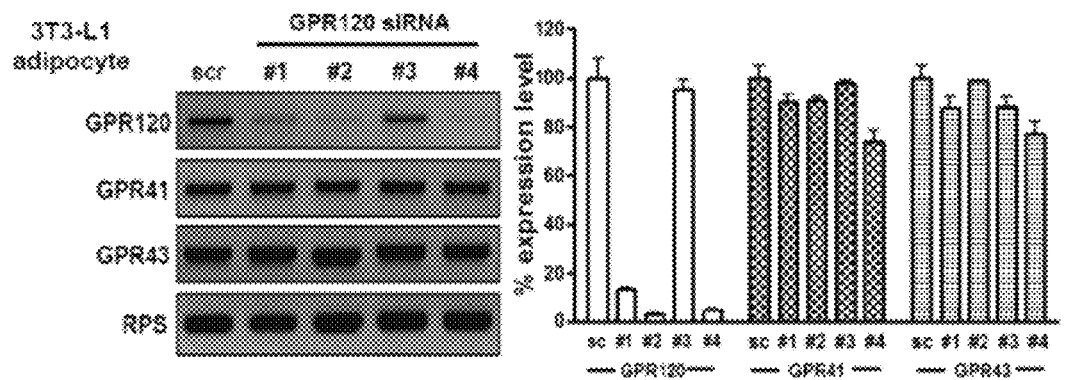
Figure 8E:
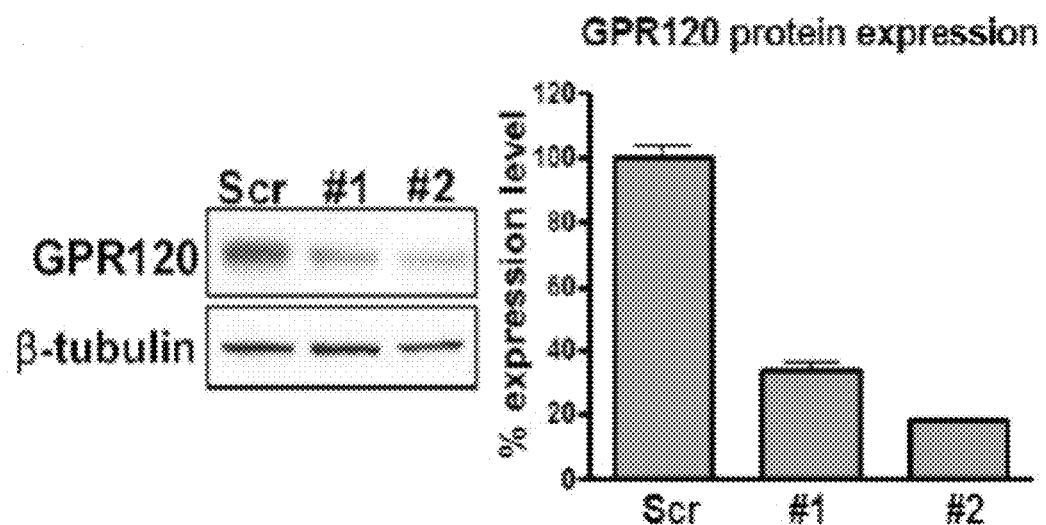
Figure 8F:
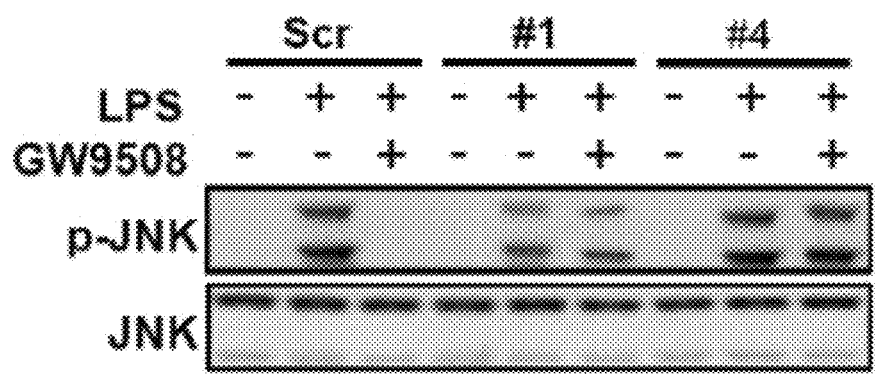

It has been previously reported that GPR120 signals via a Gαq/11-coupled pathway and can respond to long chain FAs (Hirasawa et al., 2005). To pursue the biology of GPR120, a tool compound was needed, and, some years ago, Glaxo published GW9508 as a GPR40 selective agonist. However, this compound was not specific and also stimulated GPR120 (Briscoe et al., 2006). Since macrophages and adipocytes do not express GPR40 (this was confirmed by repeated q-PCR and RT-PCR measures, FIG. 8A), GW9508 is a functional GPR120 specific compound in these cell types. Using this approach, we found that GW9508 treatment broadly and markedly repressed the ability of the TLR4 ligand LPS to stimulate inflammatory responses in RAW 264.7 cells (FIGS. 1D and E). Thus, GW9508 inhibited LPS stimulated phosphorylation of IKKβ and JNK, prevented IκB degradation, and inhibited TNF-α and IL-6 secretion. All of these effects of GW9508 were completely abrogated by siRNA mediated knockdown of GPR120 (FIG. 1D, E and FIG. 5F).

Figure 2A:
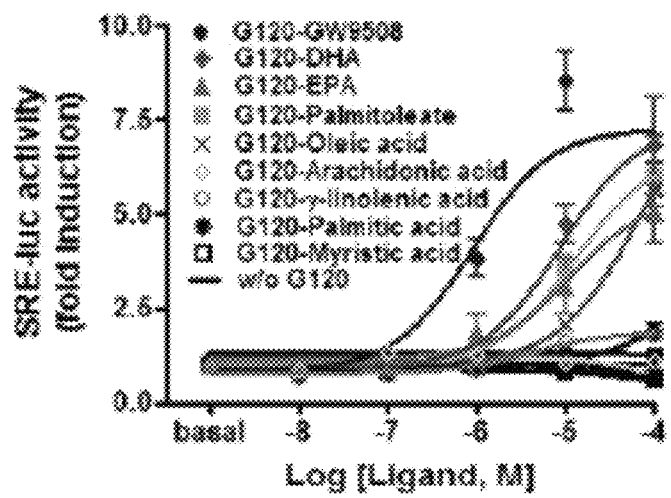
FIG. 2. Omega-3 FA stimulates GPR120 and mediates anti-inflammatory effects. (A) GPR120-mediated SRE-luc activity after treatment with various FAs (circles GPR120-GW9508; diamonds GPR120-DHA; triangles GPR120-EPA; squares GPR120-Palmitoleate; Xs GPR120-Oleic acid; empty diamonds GPR120-Arachidonic acid; empty circles GPR120-γ-linoleic acid; asterics GPR120-Palmitic acid; empty squares GPR120-Myristic acid). Results are fold activities over basal. Each data point represents mean±SEM of three independent experiments performed in triplicate. Black lines indicate SRE-luc activities without GPR120 transfection or with non-stimulating FAs. DHA inhibits LPS-induced inflammatory signaling (B), cytokine secretion (C) and inflammatory gene mRNA expression level (D) in RAW 264.7 cells, but not in GPR120 knockdown cells. (E and F) GPR120 stimulation inhibits LPS-induced inflammatory response in WT primary macrophage, Data are expressed as the mean±SEM of three independent experiments. *, $p<0.05$ versus LPS treatment in scrambled siRNA transfected cells or WT IPMacs. See also FIG. 9.
Figure 2B:
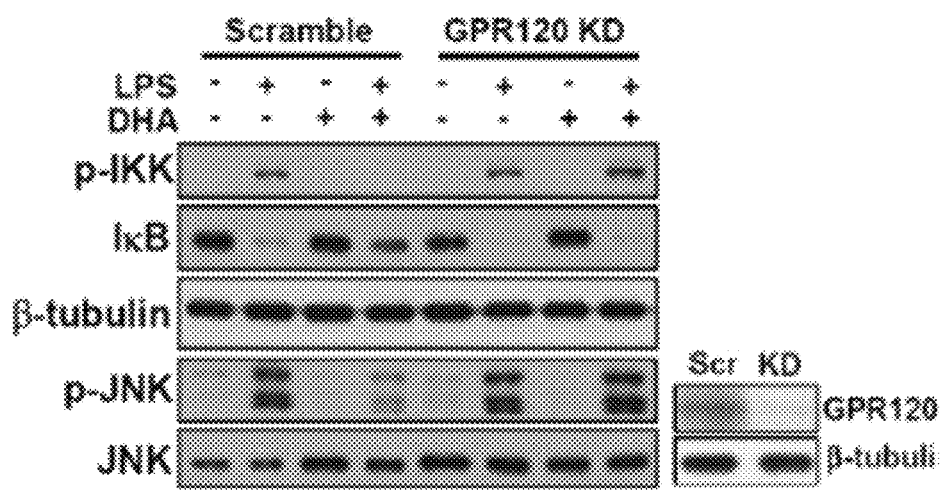
Figure 2C:
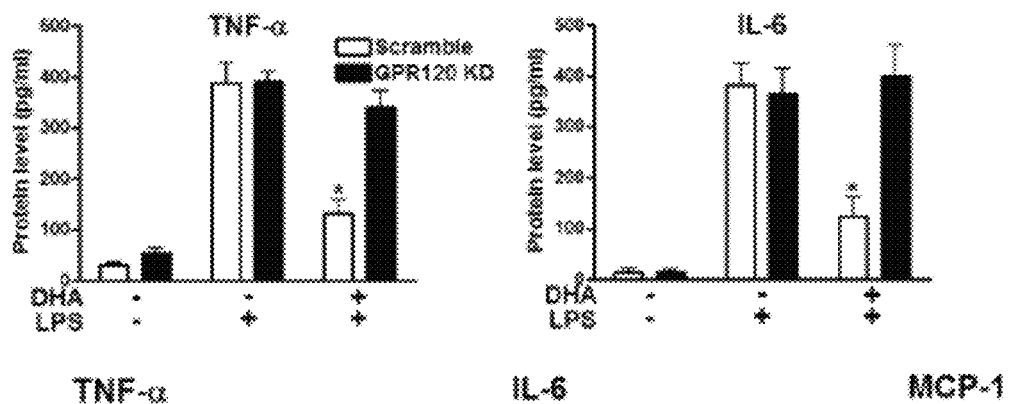
Figure 2D:
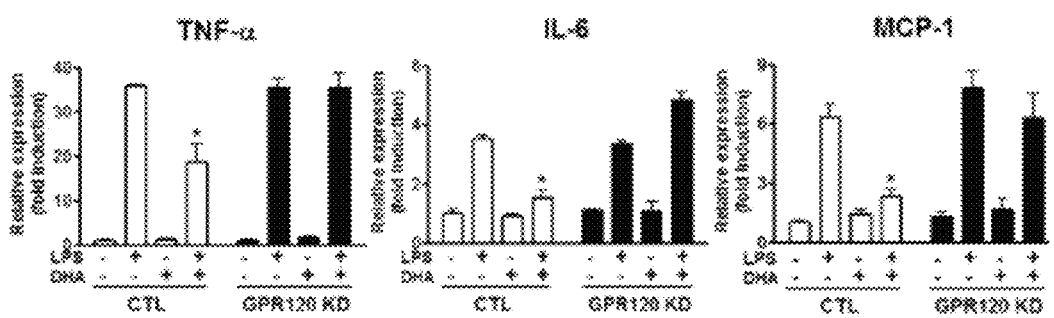
Figure 9A:
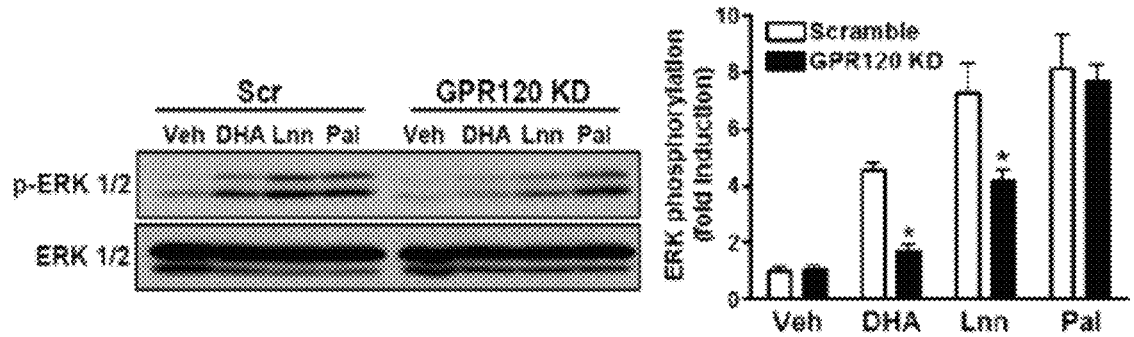
FIG. 9, related to FIGS. 2 and 3. DHA-stimulated GPR120 inhibits TNF-α, TLR2 and TLR3-induced inflammation via a β-arrestin2 dependent mechanism. (A) ERK1/2 phosphorylation stimulated by GPR120 activation in RAW 264.7 cells transfected with scrambled or GPR120 siRNA. Cells were treated with 100 μM of DHA, α-linolenic acid or palmitic acid for 5 min. Left panel is a representative image from three independent experiments, and the scanned bar graph (right panel) shows fold induction over the vehicle treatment. Data are expressed as the mean±SEM of three independent experiments. *, $p<0.05$ versus scrambled siRNA transfected cells. (B) Differentiated 3T3-L1 adipocytes were transfected with scrambled or GPR120 siRNA (GPR120 KD) and then 48 hr after siRNA transfection, cells were treated with 100 μM of DHA or GW9508 for 1 hr prior to TNF-α (10 ng/ml) treatment for 7 min prior to harvesting and then subjected to western blotting with the indicated antibodies. (C) RAW 264.7 cells, transfected with scrambled or GPR120 siRNA (GPR120 KD), were treated with 100 μM of DHA for 1 hr prior to 10 min TLR2 ligand, Pam3CSK4 (50 ng/ml), or TLR3 ligand, poly(I:C) (1 μg/ml), treatment and then subjected to western blotting. (D) To characterize the interaction site between β-arrestin2 and GPR120 or TAB1, HA-tagged GPR120 and FLAG-tagged serial C-terminal deletion mutants of β-arrestin2 (full, 1-300, 1-253, 1-176, and 1-163) or an N-terminal deletion mutant (80-410) were cotransfected in 293 cells. For immunoprecipitation of FLAG-βarr2 and HA-GPR120, cells were treated with DHA for 30 min, while DHA was used for 1 hr to detect endogenous TAB1 and FLAG-βarr2 interactions.
Figure 9B:
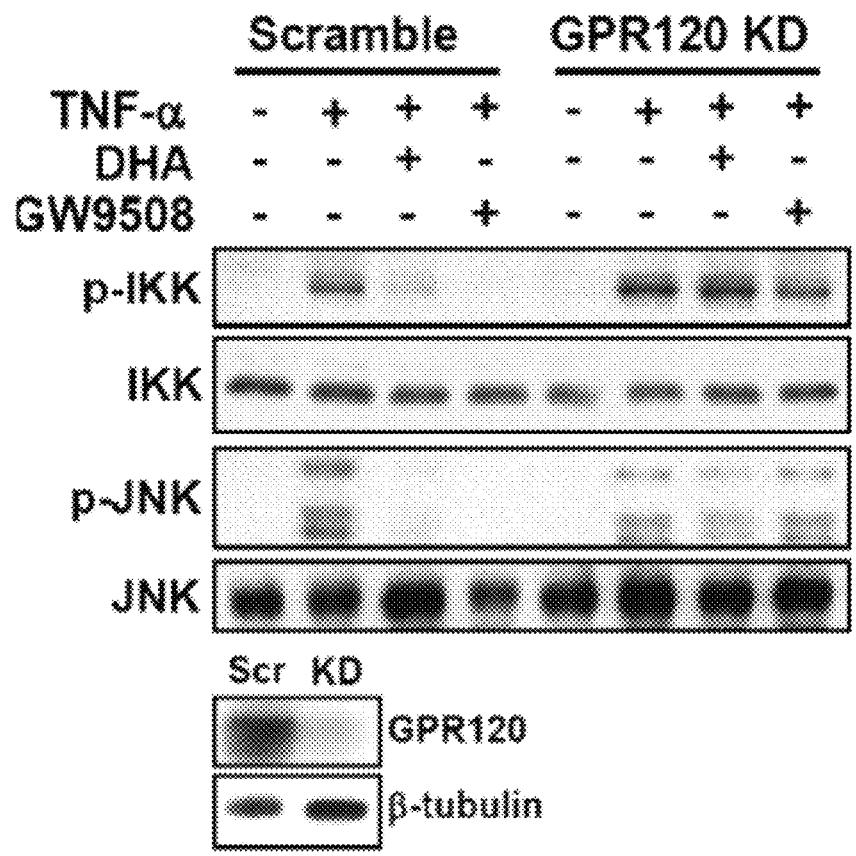

Based on these remarkable anti-inflammatory effects of GPR120 stimulation, we established a cell based reporter system by transfecting HEK 293 cells with constructs for GPR120 along with a serum response element-luciferase promoter/reporter (SRE-luc). Since GPR120 is a Gαq/11-coupled receptor, it stimulates both PKC and MAP kinase, and both of these biologic effects are detected by the SRE-driven reporter system (Oh et al., 2005). The reporter cells were treated with various FAs and the synthetic GW9508 ligand. We found that GW9508, the ω-3 FAs (DHA and EPA) and palmitoleate (C16:1n7), all activated the SRE-luc reporter with an $EC_{50}$ of 1-10 μM (FIG. 2A), while SFAs were without effect. GW9508 and DHA were used at 100 μM in all subsequent studies to achieve maximal action. The ω-3 FAs (DHA and α-linolenic acid), and SFA (palmitic acid (C16:0)) activated ERK phosphorylation in RAW 264.7 cells, but only DHA- and α-linolenic acid-mediated ERK phosphorylation were abolished by GPR120 knockdown (FIG. 9A). These results indicate that ω-3 FAs, but not SFAs, specifically activated ERK via GPR120.

Figure 2E:
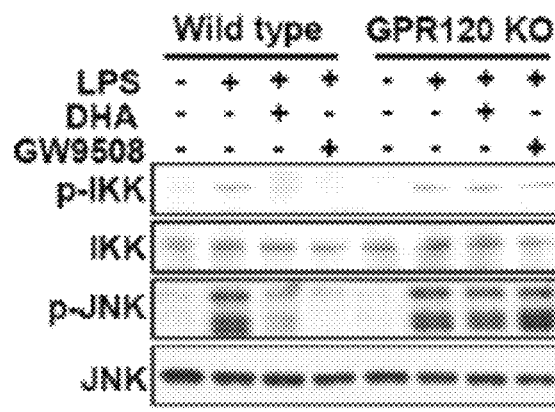
Figure 2F:
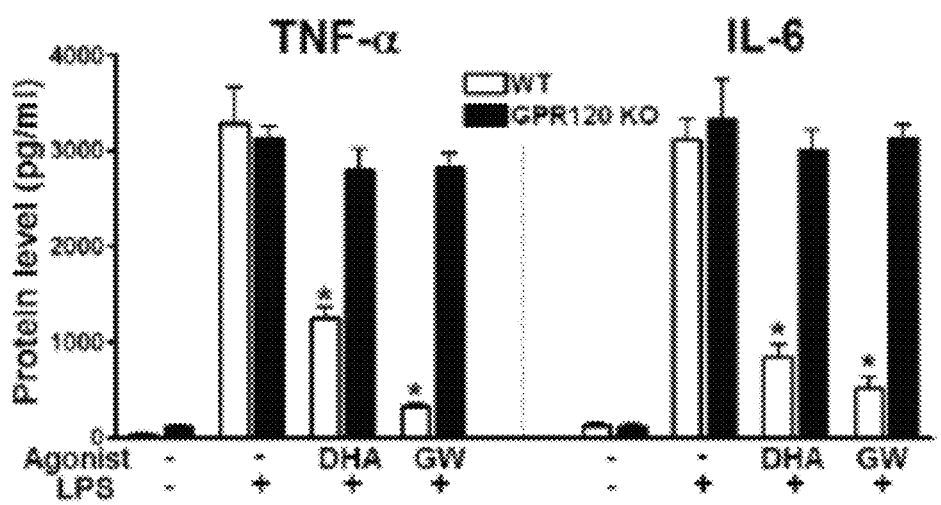
Figure 9C:
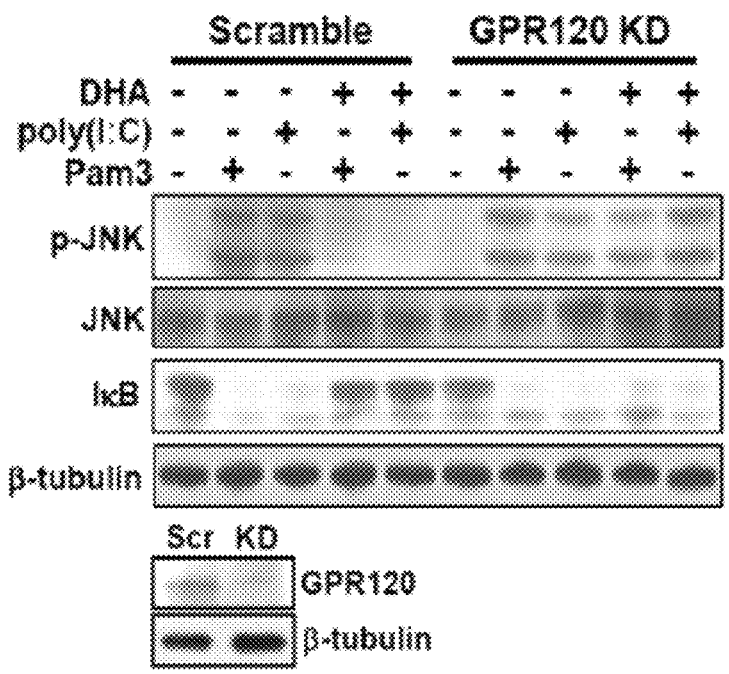

The activation of GPR120 by ω-3 FAs, as well as its expression in adipocytes and macrophages, led us to study whether DHA, a representative ω-3 FA, can modulate inflammation through GPR120 in these cells. To examine this, we pre-treated RAW 264.7 cells and 3T3-L adipocytes with GW9508 or DHA for 1 hr, followed by LPS (TLR4), TNF-α, TLR2, or TLR3 stimulation, respectively. We found that GW9508 and, more importantly, DHA, strongly inhibited LPS-induced phosphorylation of JNK and IKKβ, IκB degradation, cytokine secretion and inflammatory gene expression level in RAW 264.7 cells (FIG. 2B-D) as well as TNF-α, TLR2 and TLR3- induced JNK and IKKβ phosphorylation in 3T3-L1 adipocytes (Fig. S2B) or RAW 264.7 cells (FIG. 9C). All of the effects of GW9508 and DHA were completely prevented by GPR120 knockdown, demonstrating that these anti-inflammatory effects were specifically exerted through GPR120 (FIGS. 1, 2, 8, and 9). Similar results were seen in primary wild type (WT) intraperitoneal macrophages (IPMacs) and GPR120 knockout (KO) IPMacs (FIGS. 2E and F). These data argue that GPR120 is an ω-3 FA receptor or sensor, and provide a molecular mechanism for the anti-inflammatory effects of this class of FAs.

Role of β-Arrestin2 in GPR120 Signaling

Figure 3A:
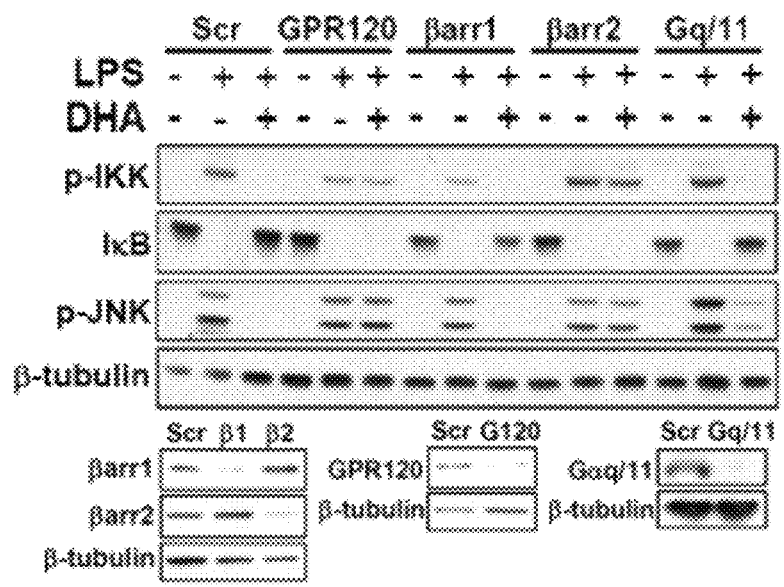
FIG. 3. GPR120 internalization with β-arrestin2 mediates anti-inflammatory effects. (A) RAW 264.7 cells were transfected with siRNA as indicated and stimulated with or without 100 μM of DHA 1 hr prior to LPS (100 ng/ml) treatment for 10 min and then subjected to western blotting. (B) TNF-α secretion was measured in RAW 264.7 cell cultured media with or without RNA interference as indicated. (C) Phosphorylation of TAK1 and MKK4 in RAW 264.7 cells with or without siRNA transfection as indicated. (D) HEK 293 cells were co-transfected with HA-GPR120 and β-arrestin2.GFP to analyze GPR120 internalization after DHA stimulation for the indicated times. GPR120 (left column) and β-arrestin2 (middle column) were localized by confocal microscopy. (E) Co-immunoprecipitation between GPR120 and β-arrestin2 with DHA stimulation for 30 min in RAW 264.7 cells and, (F) HEK 293 cells (HA-GPR120 and (β-arrestin2*GFP), respectively. Lysate indicates 1/10 input in each experiment. Interaction between TAB1 and β-arrestin2 (G), and interaction between TAB1 and TAK1 (H) were detected by co-immunoprecipitation and the scanned bar graph quantitates the association in RAW 264.7 cells. (I) Schematic diagram of the β-arrestin2 and GPR120-mediated anti-inflammatory mechanism. The left half of the diagram indicate the DHA-mediated anti-inflammatory effect, and the right half of the diagram indicate the LPS- and TNF-α-induced inflammatory pathway. See also FIG. 9.
Figure 3B:
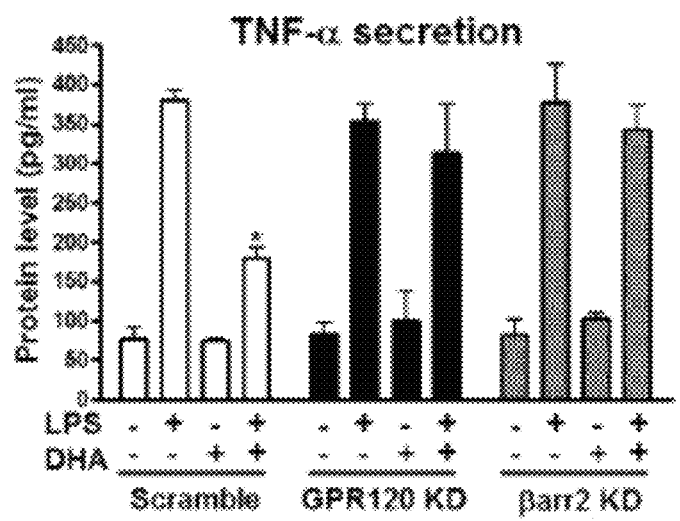

Given these potent cell selective anti-inflammatory effects, it was of interest to understand the specific mechanisms whereby signals from GPR120 inhibit inflammatory pathways. To further assess this, we used RNA interference to examine molecules involved in generation of GPR120 signals. As seen in FIGS. 3A and B, LPS signaling was not affected by β-arrestin 1, 2 or Gαq/11 knockdown. However, with β-arrestin2 knockdown, DHA-mediated anti-inflammatory signaling was extinguished, while β-arrestin and Gαq/1 knockdown were without effect (FIG. 3A).

Figure 3C:
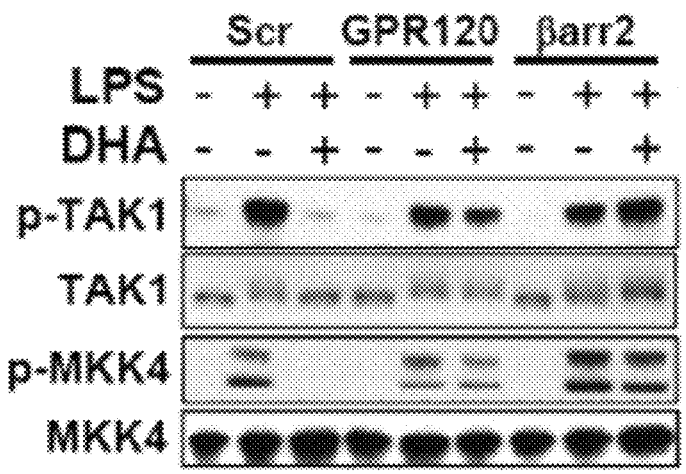
Figure 3D:
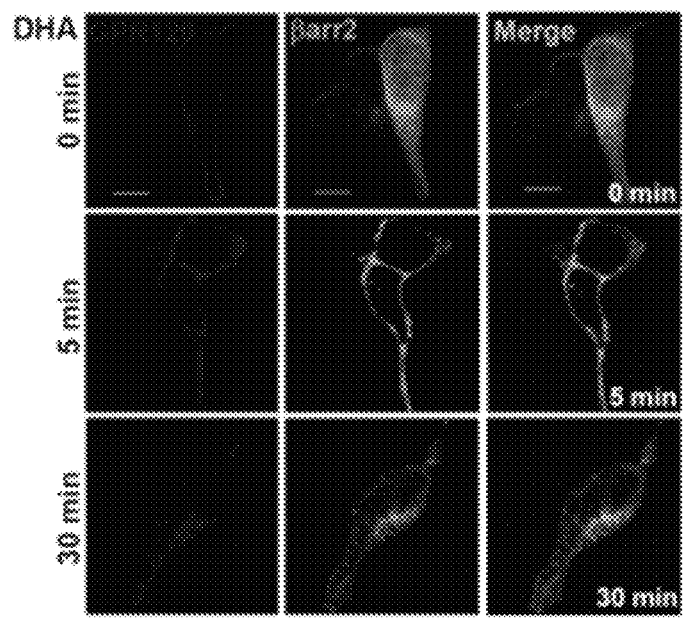
Figure 3E:
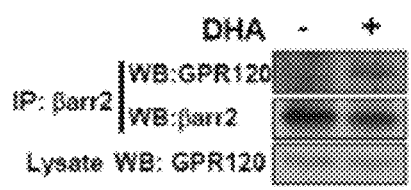
Figure 3F:
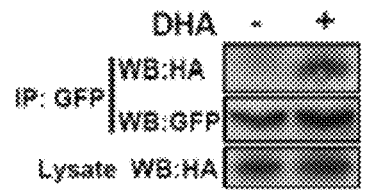
Figure 3G:
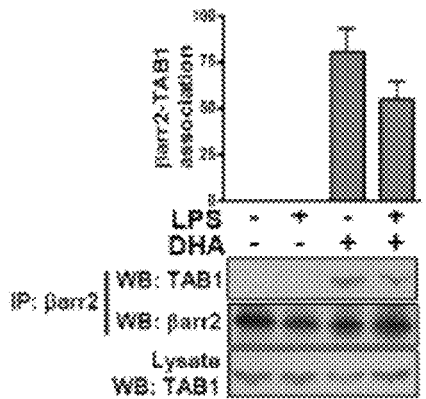
Figure 3H:
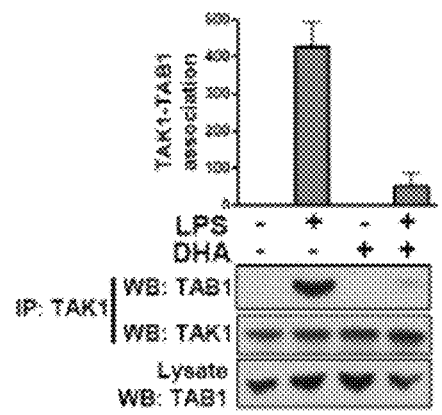
Figure 3I:
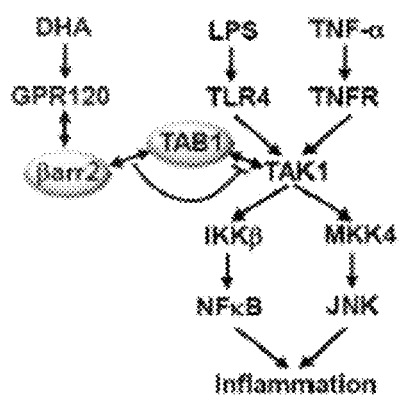

FIG. 3A and FIG. 9 show that GPR120 stimulation inhibits both TLR4- and TNF-α mediated inflammatory responses. Since the TNF-α and TLR signaling cascades converge downstream of GPR120 activation, these results indicate that the site of GPR120-induced inhibition is either at, or upstream, of JNK/IKKβ. LPS activates inflammation through the TLR4 pathway by engaging the serine kinase IRAK, leading to phosphorylation of transforming growth factor-β activated kinase 1 (TAK1) which is upstream of MKK4/JNK and IKKβ (Kawai and Akira, 2006, FIG. 3I). TNF-α and TLR2/3 also leads to stimulation of TAK1, resulting in activation of IKKβ and JNK (Takaesu et al., 2003). Consequently, we determined whether DHA stimulation of GPR120 inhibited TAK1 and MKK4. As seen in FIG. 3C, DHA treatment abrogated LPS-induced TAK1 and MKK4 phosphorylation in a GPR120 and β-arrestin2-dependent manner. Since TLR2/3/4 and TNF-α signaling were inhibited by GPR120 activation, these results indicate that DHA signaling intersects at TAK1 and inhibits all upstream input activating signals via a GPR120/β-arrestin2 interaction (FIG. 3I).

After ligand stimulation, β-arrestin2 can translocate to a number of GPCRs where it mediates receptor internalization and signaling (Barak et al., 1997). We transfected HEK 293 cells with β-arrestin2.GFP to visualize intracellular trafficking of β-arrestin2 following activation of GPR120 (FIG. 3D). In the basal state, GPR120 was localized to the plasma membrane as assessed by immunostaining (red fluorescence, FIG. 3D), while β-arrestin2 exhibited a diffuse, largely cytoplasmic staining pattern (green, FIG. 3D). Following DHA treatment for 5 min, β-arrestin2*GFP translocated from the cytosol to the plasma membrane and can be seen colocalized with GPR120 (merged, right fields). After 30 min of DHA treatment, much of the GPR120 is internalized, as visualized by punctate intracellular staining (lower left panel), and 1-arrestin2*GFP is now co-localized with the intracellular GPR120 (lower right panel, FIG. 3D). DHA-stimulated binding of β-arrestin2 to activated GPR120 was also detected by co-immunoprecipitation (FIGS. 3E and F).

Figure 9D:
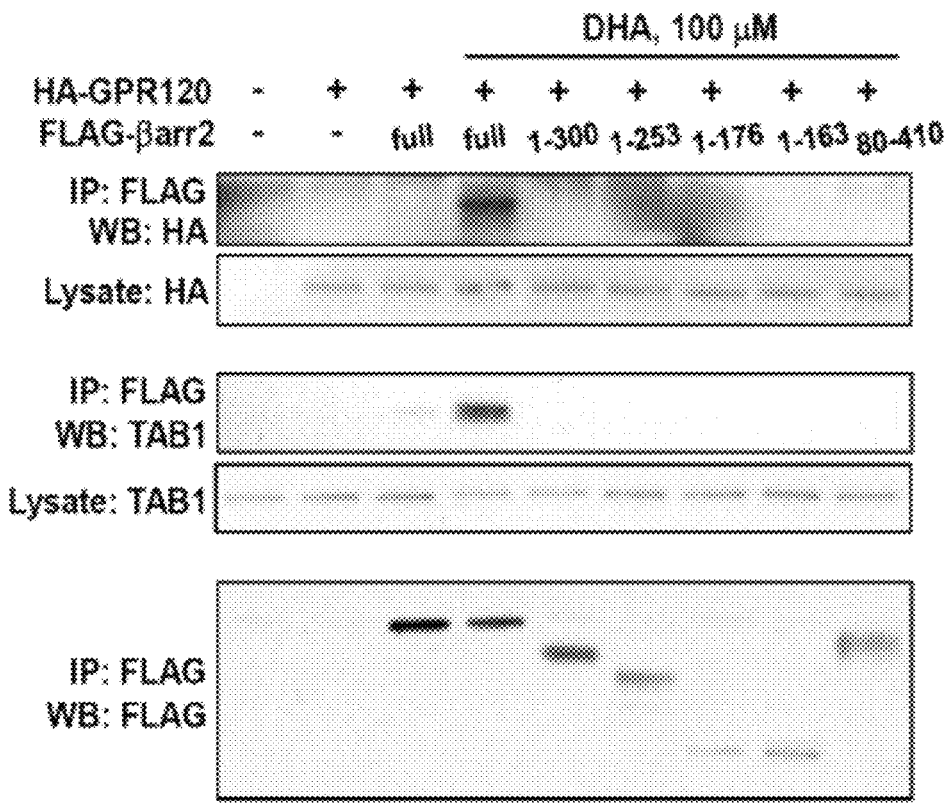

LPS or TNF-α signaling activate TAK1 by causing the association of TAK1 binding protein 1 (TAB1) with TAK1. FIG. 3H shows that LPS stimulation of RAW 264.7 cells causes TAB1/TAK1 association. DHA treatment leads to the association of β-arrestin2 with TAB1 (FIG. 3G) and largely blocks TAK1/TAB1 association (FIG. 3H). To further examine the interaction site of β-arrestin2 and GPR120 or TAB1, we pursued co-immunoprecipitation with a series of β-arrestin2 truncation/deletion mutants (FIG. 9D). Full length β-arrestin2 was able to bind to GPR120 and TAB1 only in the presence of DHA, clearly showing the DHA dependency of this interaction. Interestingly, only the full length β-arrestin2 co-precipitated with GPR120 and TAB1, while a series of deletion/truncation β-arrestin2 mutants did not, indicating that the interactions are dependent on the complete tertiary structure of β-arrestin2 (FIG. 9D; Luttrell et al., 1999). Taken together, these results suggest that GPR120 activation leads to association of β-arrestin2 with the receptor and that this complex subsequently internalizes, whereupon β-arrestin2 can bind to TAB1. The data further suggest that association of β-arrestin2 with TAB1 blocks TAB1/TAK1 binding, resulting in inhibition of TAK1 phosphorylation and activation (FIG. 3I).

GPR120 Activation Enhances Glucose Uptake in 3T3-L1 Adipocytes.

Figure 4A:
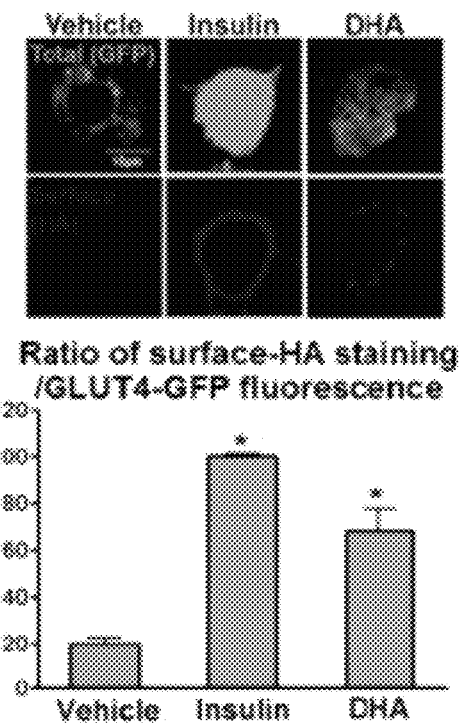
FIG. 4. GPR120 activation enhances GLUT4 translocation and glucose uptake. (A) 3T3-L1 adipocytes were transfected with a dually tagged HA-GLUT4-GFP construct. Total GLUT4 expression was determined by GFP fluorescence, and GLUT4 translocation to the cell surface after 100 ng/ml insulin or 100 μM DHA stimulation for 30 min was determined by indirect immunofluorescence of the HA-conjugated with Alexa 594 in fixed cells. Translocation following insulin stimulation was expressed as a percentage of the maximum response. Bar graph represents the mean±SEM data from four independent experiments. *, $p<0.05$ vs. vehicle treatment. (B) Glucose uptake was measured in WT and GPR120 KO mouse primary adipose tissue and in (C-F) 3T3-L1 adipocytes±siRNA with the indicated treatment. Whereas knockdown Gαq/11 completely blocked the effects of DHA to stimulate glucose transport in (F), knockdown β-arrestin1 and β-arrestin2 in (G) and (H), respectively, had no effect. Data are expressed as mean±SEM of three independent experiments in triplicate. *, $p<0.05$ vs. basal activity. The indicated siRNA knockdown efficiency was validated by western blotting. See also FIG. 10.
Figure 4B:
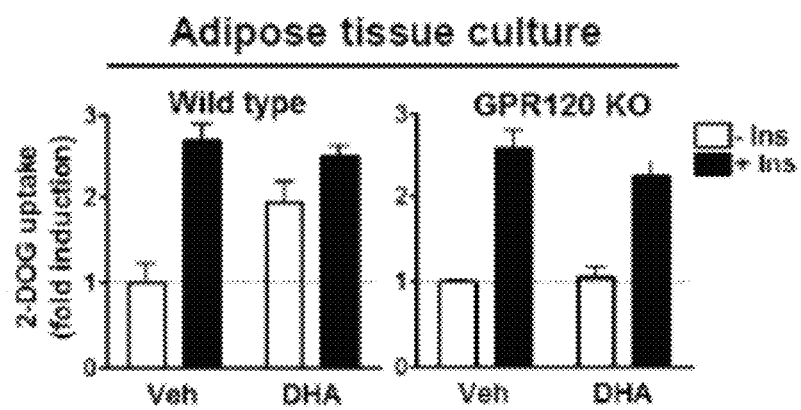
Figure 4C:
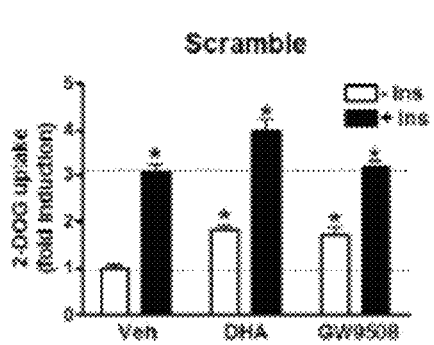
Figure 4D:
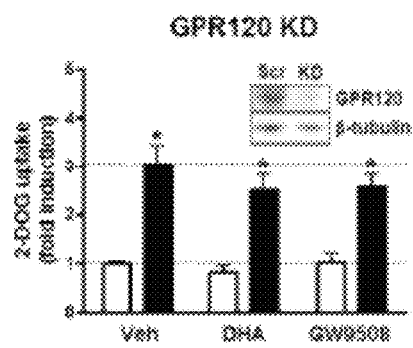
Figure 4E:
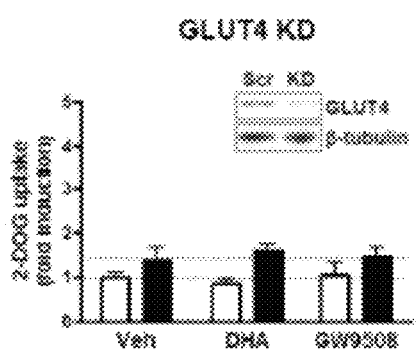
Figure 4F:
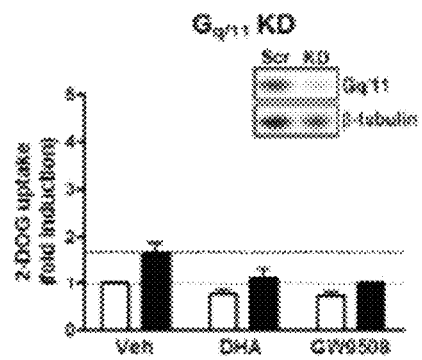
Figure 4G:
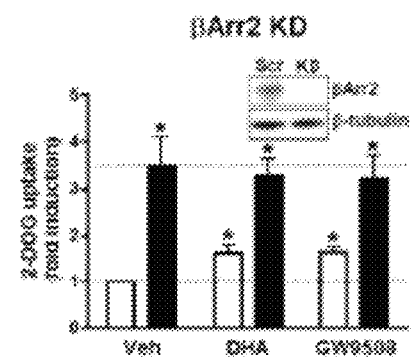
Figure 4H:
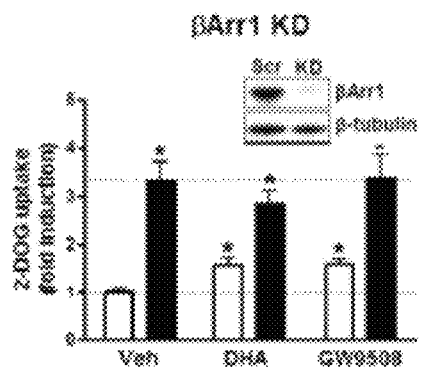
Figure 10A:
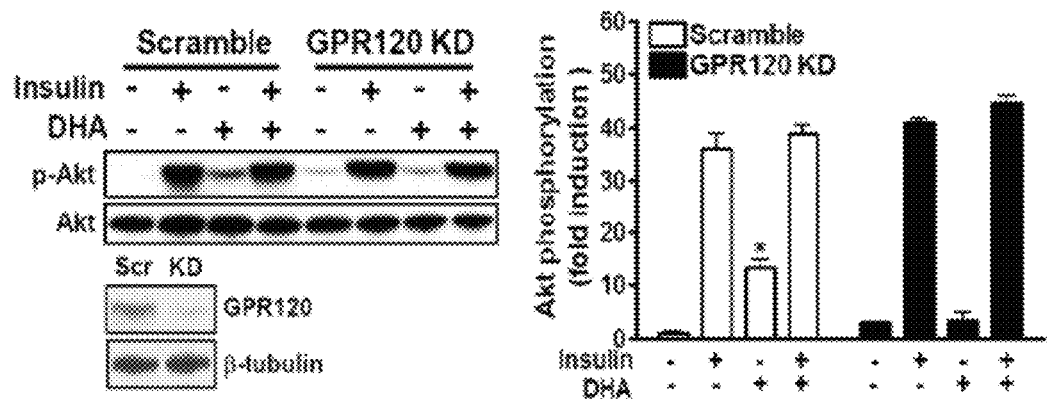
FIG. 10, related to FIG. 4. DHA activates Akt phosphorylation in a GPR120-dependent manner. (A) Differentiated 3T3-L1 adipocytes were transfected with scrambled or GPR120 siRNA and then 48 hr after siRNA transfection, cells were treated with 100 μM of DHA 30 min prior to insulin (3 ng/ml) treatment for 7 min followed by western blotting with phosphorylated Akt (S473) antibody. Left panel is a representative image from three independent experiments, and the scanned bar graph (right panel) shows fold induction over basal after normalization for total Akt. Data are expressed as the mean±SEM of three independent experiments. *, $p<0.05$ versus basal. (B) Cells were treated with the PI3K inhibitor LY294002 (50 μM) for 30 min before DHA (100 μM) or insulin (3 ng/ml) treatment. (C) Phosphorylation of IRS-1 was detected after DHA or insulin treatment of 3T3-L1 adipocytes. (D) Schematic diagram of GPR120-mediated Akt activation in 3T3-L1 adipocytes.
Figure 10B:
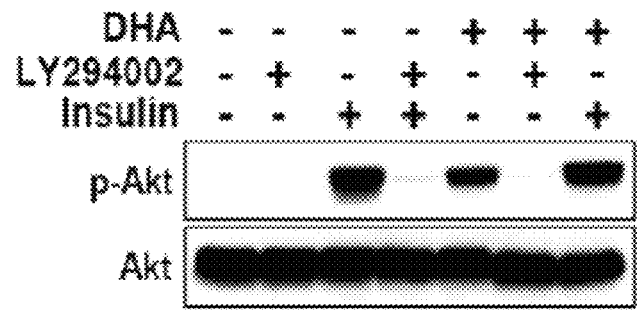
Figure 10C:
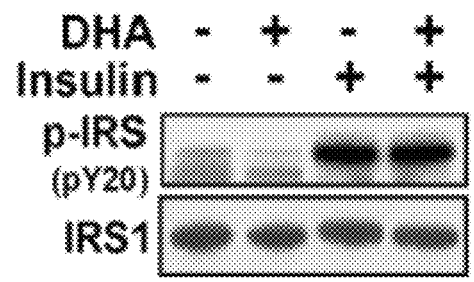
Figure 10D:
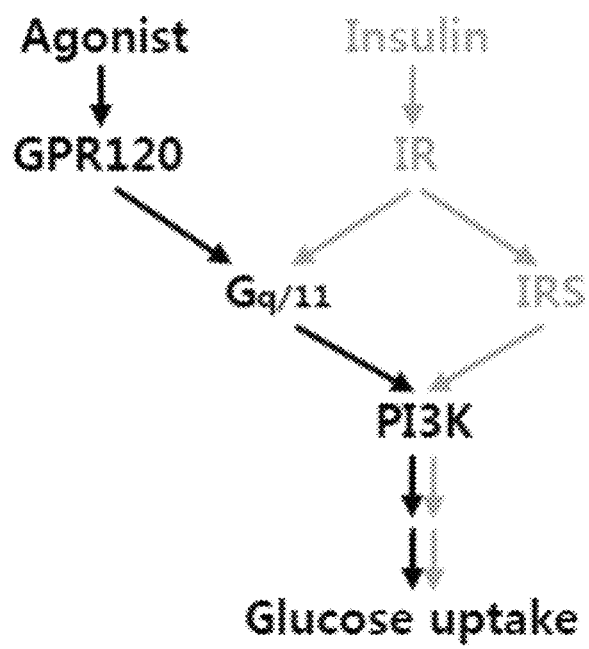
Figure 11A:
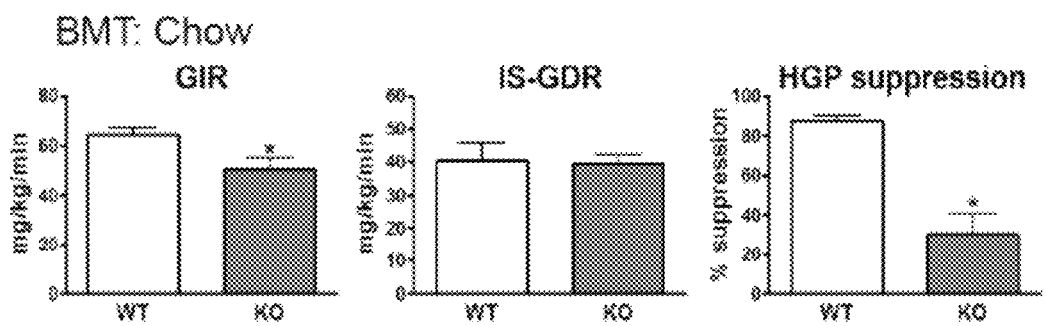
FIG. 11, related to FIG. 5. Hyperinsulinemic/euglycemic clamp studies in bone marrow transplanted animals and muscle expression of GPR120. For bone marrow transplantation studies, WT or GPR120 KO mouse bone marrow (BM) was injected into irradiated WT C57B1/6 animals after 8 weeks for BM reconstitution, GPR120 was >90% reduced in circulating monocytes. Animals were then kept on either chow or switched to 60% HFD for weeks (±supplemention with ω-3 FAs for 5 weeks). (A) BMT GPR120 KO animals on chow are insulin resistant compared to WT controls. This effect is mediated by decreased GIR and a greater suppression of HGP in WT animals compared to KOs (n=5 for WT and n=6 per KO group). (B) BMT GPR120 KO animals on HFD supplemented with 0ω-3 FAs (+ω3) are insulin resistant compared to WT controls. This effect is shown by decreased GIR, decreased IS-GDR, and a greater suppression of HGP in WT animals compared to KOs. (C) GPR120 expression levels in various tissues. RPS3 was the internal control for normalization. GPR120 is not expressed in soleus, or EDL muscle. (D) Glucose uptake is not altered by DHA treatment (100 µM) in L6 myocytes, compared to vehicle treated cells. (E) Hyperinsulinemic/euglycemic clamp studies performed on WT animals on 60% HFD for 15 weeks. On the day of the clamp, the animals were gavaged with saline or DHA (300 µl EPAX 1050TG) for 2 hr after fasting. Four hr after gavage, the animals were clamped using 8 mU/kg/min of insulin. Acute DHA treatment has no effect on whole body glucose homeostasis compared to saline administered controls. Data are expressed as mean±SEM. *, p<0.05 compared to WT in (A) and (B).
Figure 11B:
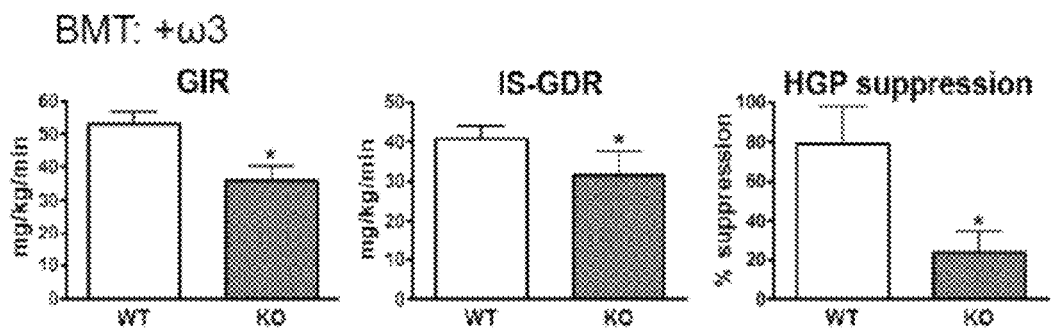
Figure 11C:
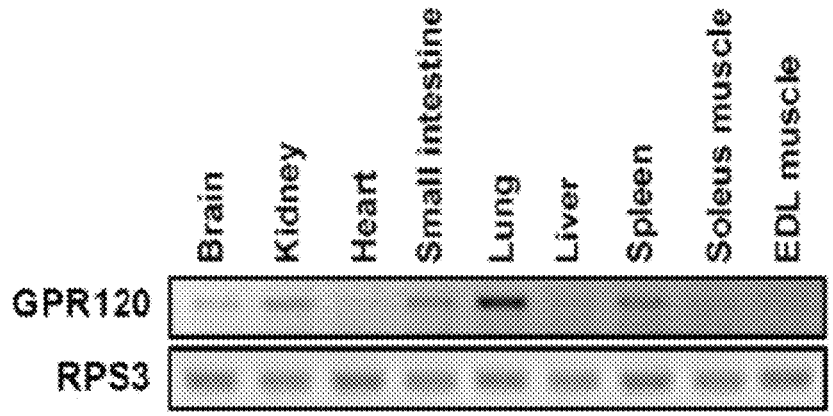

Since our data show that GPR120 is expressed in mature adipocytes and signals through Gαq/11 in these cells, we assessed the effects of GPR120 stimulation on insulin sensitivity in primary adipose tissue cultures and in 3T3-L1 adipocytes. Primary adipose tissue explants and 3T3-L1 adipocytes were pretreated for 30 min with GW9508 or DHA, followed by measurement of basal and insulin stimulated GLUT4 translocation (FIG. 4A) and 2-deoxyglucose (2-DOG) transport (FIG. 4B-H). Ligand-stimulation of GPR120 led to an increase in glucose transport and translocation of GLUT4 to the plasma membrane in adipocytes, but was without effect in muscle cells (FIG. 11D) which don't express GPR120 (FIGS. 1B and 11C). This stimulatory effect of DHA and GW9508 was blocked when GPR120 or Gαq/11 was depleted by siRNA knockdown (FIGS. 4D and F). GLUT4 knockdown also blocked the effects of DHA and GW9508, while the effects of insulin were decreased by ~90% (FIG. 4E). This, along with the GLUT4 translocation data provided in FIG. 4A, indicates that the stimulatory effects of GPR120 are indeed working through GLUT4. Further assessment of this pathway showed that DHA had a modest effect to stimulate phosphorylation of Akt, but that this was abrogated with GPR120 knockdown (FIG. 10A). The effects of DHA to stimulate Akt were blocked by inhibiting PI3 kinase with LY294002 (FIG. 10B). Finally, DHA did not stimulate IRS-1 phosphorylation (FIG. 10C), indicating that its glucose transport stimulatory effects were downstream of IRS-1. Knockdown of Gαq/11 also completely blocked the effects of DHA to stimulate glucose transport (FIG. 4F), while β-arrestin1 or 2 knockdown was without effect (FIGS. 4G and H). Interestingly, Gαq/11 knockdown not only inhibited DHA and GW9508 stimulated glucose transport, but it also attenuated insulin stimulatory effects, and the latter is fully consistent with previous publication (Imamura et al., 1999) showing the role of Gαq/11 in insulin signaling to glucose transport in adipocytes. This scheme is shown in FIG. 10D.

In Vivo Metabolic Studies in GPR120 KO mice

Since chronic tissue inflammation can cause insulin resistance, we hypothesized that deletion of GPR120 would enhance the pro-inflammatory tone, promoting glucose intolerance and decreased insulin sensitivity. To test this idea, GPR120 KO mice and WT littermates were evaluated on normal chow diet (NC). Body weights were similar in both groups, and as summarized in FIG. 5, glucose tolerance tests (GTT) showed a mild degree of impairment in GPR120 KO animals compared to WTs (FIG. 5A). More impressively, insulin secretion was more than 2-fold greater in the KO animals, and the combination of hyperinsulinemia and mild glucose intolerance indicates the presence of insulin resistance (FIGS. 5B and C). This was confirmed by performing hyperinsulinemic/euglycemic clamp studies in the chow fed WT and KO mice (FIG. 5D). These studies revealed a 31% decrease in the glucose infusion rate (GIR) required to maintain euglycemia in the KO mice. Since 70-80% of total body insulin stimulated glucose disposal is accounted for by skeletal muscle glucose uptake (Baron et al., 1988), the decreased insulin stimulated (IS)-glucose disposal rate (GDR) provides direct evidence for skeletal muscle insulin resistance in the KO mice. Likewise, the GPR120 KO mice exhibited a marked decrease in the ability of insulin to suppress hepatic glucose production (HGP), demonstrating the presence of hepatic insulin resistance. Thus, the decreased GIR was ~50% related to muscle and ~50% due to liver insulin resistance, respectively. Since the chow diet contains exogenous ω-3 FAs, we conclude that blunted ω-3 FA signaling in the KO mice, accounts for the decreased insulin sensitivity.

Figure 13A:
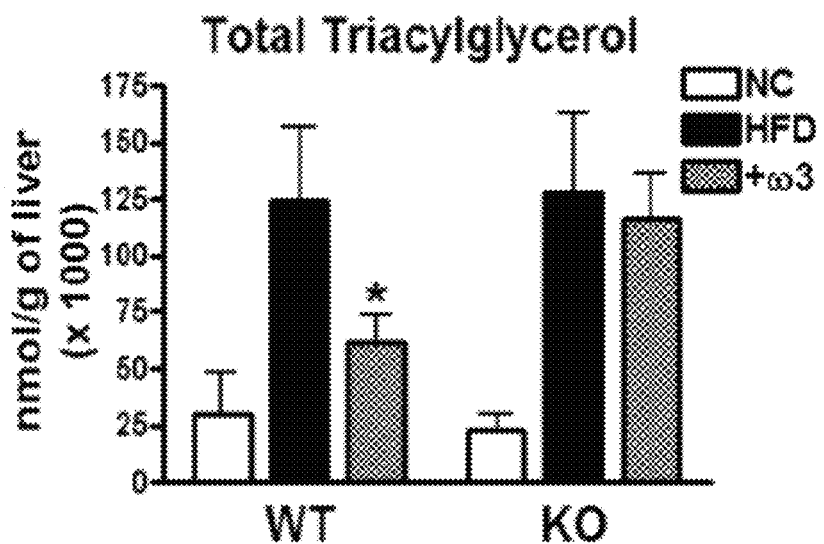
FIG. 13, related to FIGS. 5 and 7. Omega-3 FAs decrease hepatic steatosis and metabolic gene expression, and increase M2 anti-inflammatory gene expression in liver. (A) Hepatic TAG was measured by lipidomic analysis in WT and GPR120 KO mice. Hepatic TAG was decreased in HFD+ω3-fed WT, but not in GPR120 KOs. Data represent mean±SEM.*, p<0.05 and n=7 per group. (B) H&E staining of frozen sections of livers obtained from chow (NC), HFD and HFD+ω3-fed WT and GPR120 KO mice. Representative images are shown from WT and KO in each diet group, respectively (n=4 per WT for each diet group, n=3 per KO). (C) Q-PCR analysis of the indicated metabolic genes in liver of WT and GPR120 KO mice fed HFD or HFD+ω3 as indicated. n=7 per group, *, p<0.05 compared to the HFD-fed WT group. Relative mRNA levels for M pro-inflammatory genes (D) and M2 anti-inflammatory genes (E) in liver from chow, H-FD or H-TFD+ω3-fed (+ω3) WT and GPR120 KO mice as measured by q-PCR. Data are expressed as mean±SEM of three independent experiments in triplicate. n=7 per group, *, p<0.05 compared to the HFD-fed WT group. Primer sequences are shown in Table 2.

Since ω-3 FA administration can improve insulin sensitivity in rats (Buettner et al., 2006), we reasoned that ω-3 FA supplementation could alleviate HFD/obesity-induced insulin resistance in WT mice, but would be ineffective in GPR120 KOs. Accordingly, WT and GPR120 KO mice were placed on 60% HFD for 15 weeks. At this point, separate groups of 15 mice each, were treated for five additional weeks with 60% HFD or an isocaloric HFD diet containing 27% fish oil supplementation enriched in ω-3 FAs. This diet provided 50 and 100 mg of DHA and EPA, respectively, per mouse, per day. FIG. 5E shows that administration of the ω-3 FA diet led to improved insulin sensitivity with increased glucose infusion rates, enhanced muscle insulin sensitivity (increased IS-GDR), greater hepatic insulin sensitivity (increased HGP suppression), and decreased hepatic steatosis (FIGS. 13A and B). Importantly, the ω-3 FA diet was completely without effect in the GPR120 KO mice. A separate group of WT mice were treated with the insulin sensitizing thiazolidinedione Rosiglitazone, and the effects of ω-3 FAs were equal to or greater (HGP suppression) than the effects of this clinically used insulin sensitizing drug.

Figure 13B:
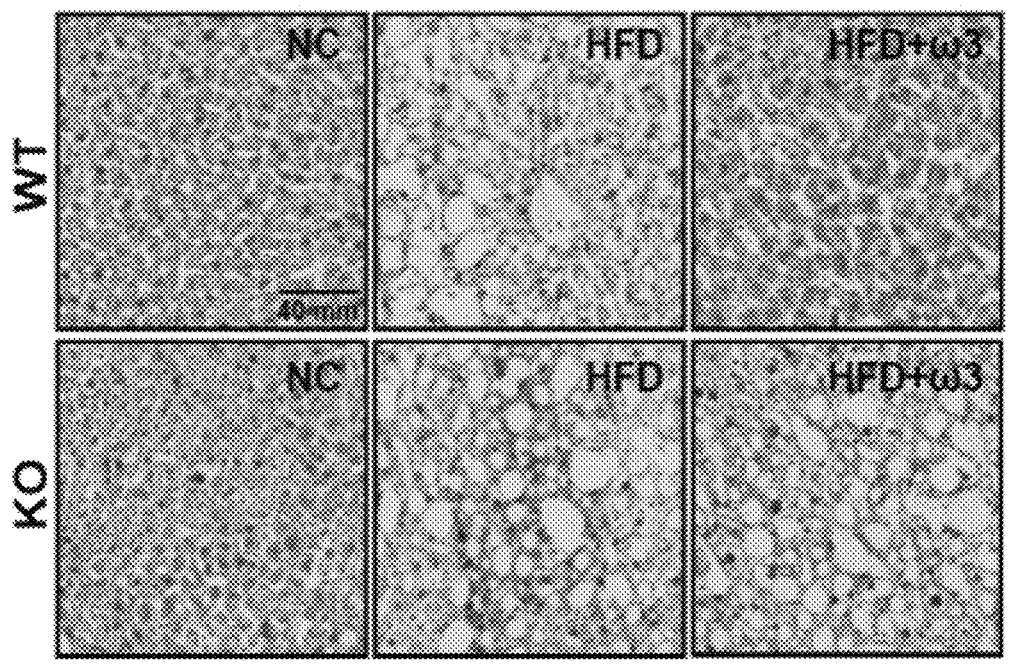
Figure 13C:
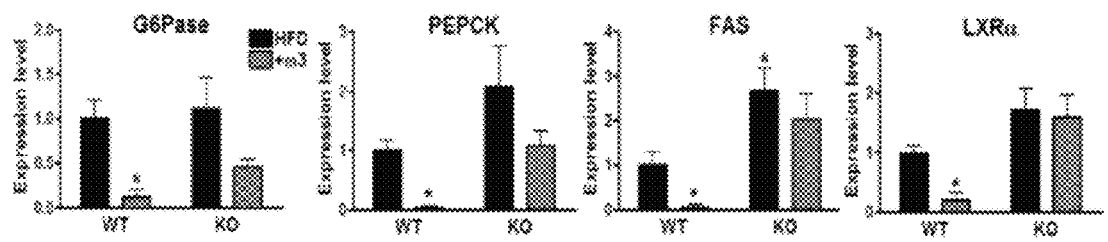
Figure 13D:
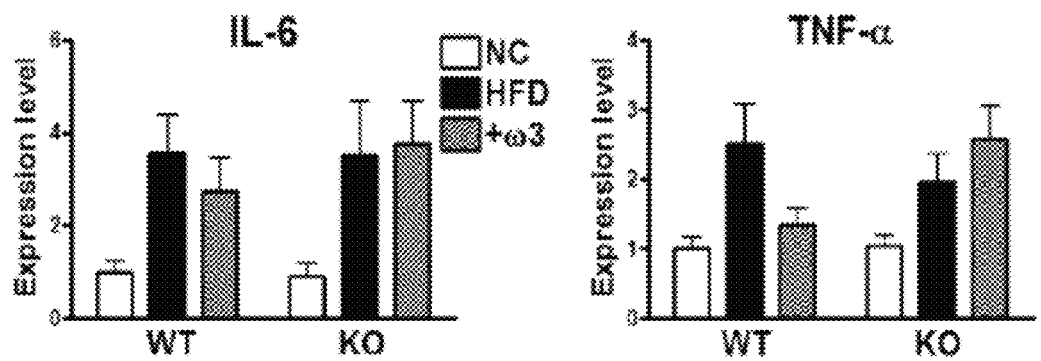
Figure 13E:
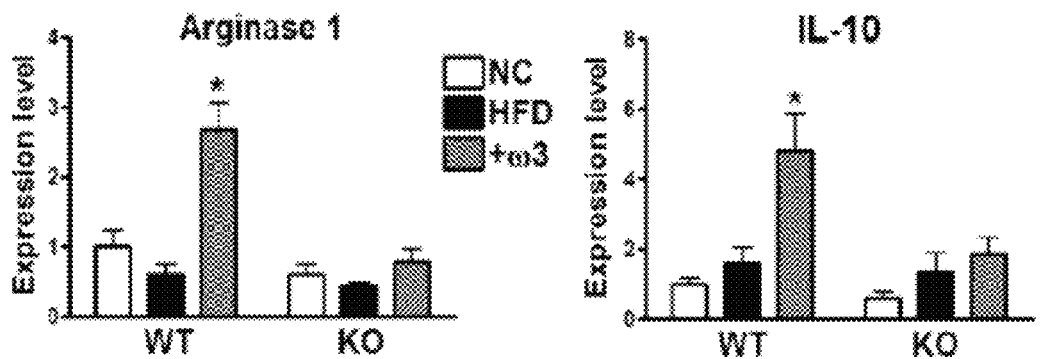

In addition to improving hepatic insulin sensitivity, ω-3 FA treatment had a beneficial effect on hepatic lipid metabolism, causing decreased liver triglycerides, DAGs, along with reduced SFA and ω-6 FA content in the various lipid classes (FIG. 13A-C and Table 2). The ω-3 FA supplementation was entirely without effect, or much less effective, at reducing hepatic lipid levels in the GPR120 KOs.

Interestingly, in the absence of ω-3 FA supplementation, GPR120 KO mice were just as susceptible to HFD-induced insulin resistance as were the WT mice. We hypothesize that this was because the 60% HFD is deficient of exogenous 0ω-3 FAs, so that ligands for GPR120 were relatively absent in these animals. To assess this, we performed a lipomics analysis of the various fatty acid classes in the chow and HFD-fed WT and KO mice. As predicted, circulating concentrations of ω-3 FAs were much lower on HFD compared to chow diets, and the administration of the ω-3 FA supplement to the HFD led to a large increase in plasma ω-3 FA content in both genotypes (FIG. 5F). This would account for the relative lack of effect of GPR120 KO on HFD alone, since ω-3 FA ligand stimulation is negligible, while the KO animals displayed an insulin resistant phenotype on chow diets when a moderate level of ω-3 FAs was provided. Importantly, the GPR120 KO mice are completely refractory to the insulin sensitizing effects of ω-3 FA administration on HFD.

To address the contribution of macrophages to the overall in vivo phenotype, we performed bone marrow transplantation (BMT) from GPR120 KOs into irradiated WT mice (adoptive transfer) to generate hematopoietic cell deletion of GPR120. The studies in the BMT WT and BMT GPR120 KO mice on chow diet revealed a highly significant 20-30% decrease in GIR in the KOs, with a more dramatic impairment in the ability of insulin to suppress hepatic glucose production (FIG. 11A). Thus, the studies in the BMT animals on the chow diet are comparable to the results (FIG. 5D) observed in WT versus whole body GPR120 KOs on chow diet. When studied on the HFD±ω-3 FA supplementation (FIG. 11B), the ω-3 FA supplemented BMT GPR120 KO animals exhibited a 30% decrease in GIR compared to the ω-3 FA supplemented BMT WTs. This was explained by skeletal muscle insulin resistance (decreased IS-GDR) and hepatic insulin resistance (decreased HGP suppression) in the GPR120 KOs compared to the WT BMT mice on the ω-3 FA supplemented HFD. These data are fully consistent with the results in the global KOs (FIG. 5E) and reinforce the concept that the in vivo phenotype we observed can be largely traced to hematopoietic cells/macrophages.

Omega-3 FAs Reduce Inflammatory Macrophages in Adipose Tissue

Figure 6A:
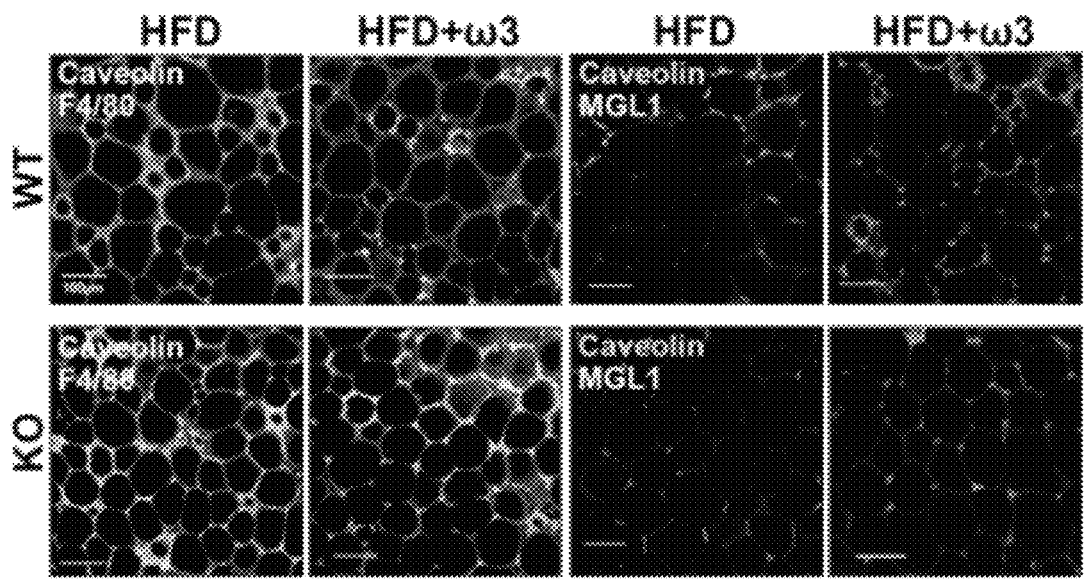
FIG. 6. Omega-3 FA enriched diet decreases inflammatory macrophage infiltration in adipose tissue. (A) Confocal merged images from epididymal fat pads from HFD and ω-3 FA enriched HFD (HFD+ω3)-fed WT and GPR120 KO mice, co-stained with anti-F4/80 and anti-Caveolin1 antibodies, left 4 panels, or anti-MGL1 and anti-Caveolin1 antibodies, right 4 panels. The image is representative of similar results from 3-4 independent experiments. Scale bar represents 100 μm. (B) Dot plot representation of CD11b versus CD11c expression for FACS data obtained from adipose tissue SVF of NC, HFD or HFD+ω3-fed WT and GPR120 KO. Scattergram is representative from three independent mice from each group. (C and D) Migratory capacity of IPMacs from WT and GPR120 KO mice as measured using an in vitro transwell chemotaxis assay as described under supplemental experimental procedures. Data are expressed as mean±SEM of three independent experiments in triplicate. *, $p<0.05$ vs. CM treatment.
Figure 6B:
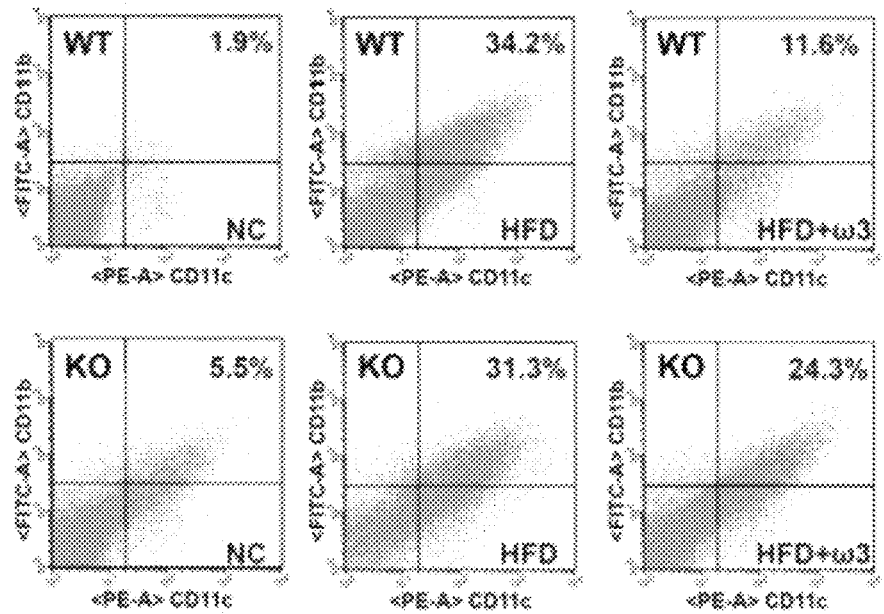

We conducted histologic examination of adipose tissue macrophages (ATMs) from WT and GPR120 KO mice on HFD or the ω-3 FA enriched HFD by immunostaining for the M1 macrophage marker F4/80 and the M2 macrophage marker MGL1 (Lumeng et al., 2008) (FIG. 6A). Consistent with previous studies (Weisberg et al., 2003; Xu et al., 2003; Nguyen et al., 2007), HFD induced a large increase in F4/80 positive ATMs, which form crown-like structures (CLS) around adipocytes in both WT and GPR120 KO mice. In contrast, MGL1 staining was minimal in both groups on HFD (FIG. 6A). On the ω-3 FA diet, we observed a decrease in F4/80 staining, along with a marked increase in MGL1 positive cells in WT mice. Importantly, no change in F4/80 or MGL1 staining was noted in the GPR120 KO mice on the ω-3 FA ☐diet. SVFs were prepared from adipose tissue and analyzed by flow cytometry to quantitate the total number of ATMs, as well as the content of CD11b+ and CD11c+ and negative macrophage subpopulations (FIG. 6B). HFD led to a large but comparable increase in CD11b+ and CD11c+ ATM content in WT and GPR120 KO mice (FIG. 6B, middle panel). Treatment with the ω-3 FA-enriched HFD caused a striking decrease in CD11b+ and CD11c+ATMs in WT mice, but was without effect in the GPR120 KO group (FIG. 6B, right panel). Thus, the FACS analysis was fully consistent with the histological results. Interestingly, CD11c+ ATM content was also greater in the GPR120 KOs on the chow diet relative to WT consistent with the insulin resistance in the KO animals.

Figure 6C:
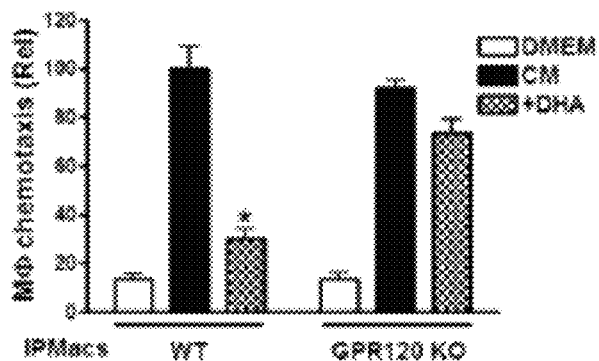
Figure 6D:
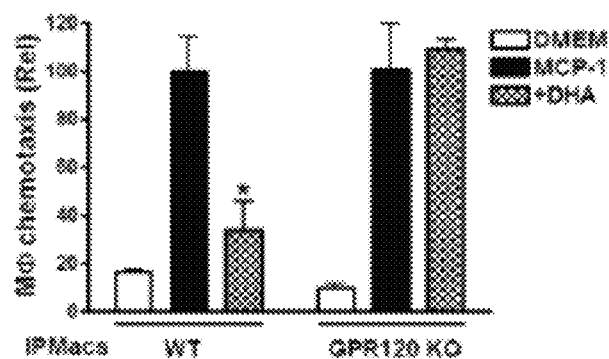

It seemed possible that the reduction in ATM content in WT animals on the ω-3 FA diet reflected decreased chemotaxis of macrophages. To test this hypothesis, we measured the migratory capacity of IPMacs from WT and GPR120 KO mice using an in vitro transwell chemotaxis assay. As seen in FIG. 6C, macrophages from both groups readily migrated towards conditioned media (CM) harvested from 3T3-L1 adipocytes. Pretreatment of macrophages with DHA for 3 hr before exposure to CM led to an 80% inhibition of chemotactic capacity in WT macrophages, but had no significant effect on IPMacs obtained from the GPR120 KO mice. Similar experiments were performed using the specific chemokine, monocyte chemotactic protein-1 (MCP-1) as a chemoattractant, rather than CM, and these experiments yielded identical results (FIG. 6D). These data indicate that ω-3 FAs cause decreased macrophage chemotaxis by acting through the GPR120 receptor, contributing to the differences in ATM content seen in FIGS. 6A and 6B.

Figure 7A:
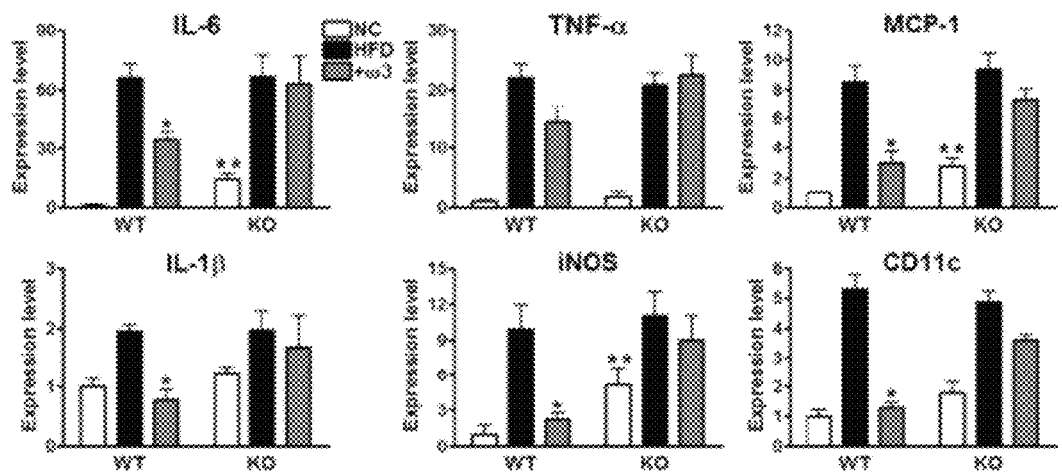
FIG. 7. M1 and M2 inflammatory gene expression levels in adipose tissue from WT vs. GPR120 KO mice. Relative mRNA levels for M1 pro-inflammatory genes (A) and M2 anti-inflammatory genes (B) in NC, HFD or HFD+ω3 (+ω3)-fed WT and GPR120 KO mice, as measured by q-PCR. Data are expressed as mean±SEM of three independent experiments in triplicate. n=7 per group, *, $p<0.05$ compared to the HFD-fed WT group. **, $p<0.05$ compared to the WT vs. GPR120 KO on NC. See also FIG. 14. Primer sequences are shown in Table 2.
Figure 7B:
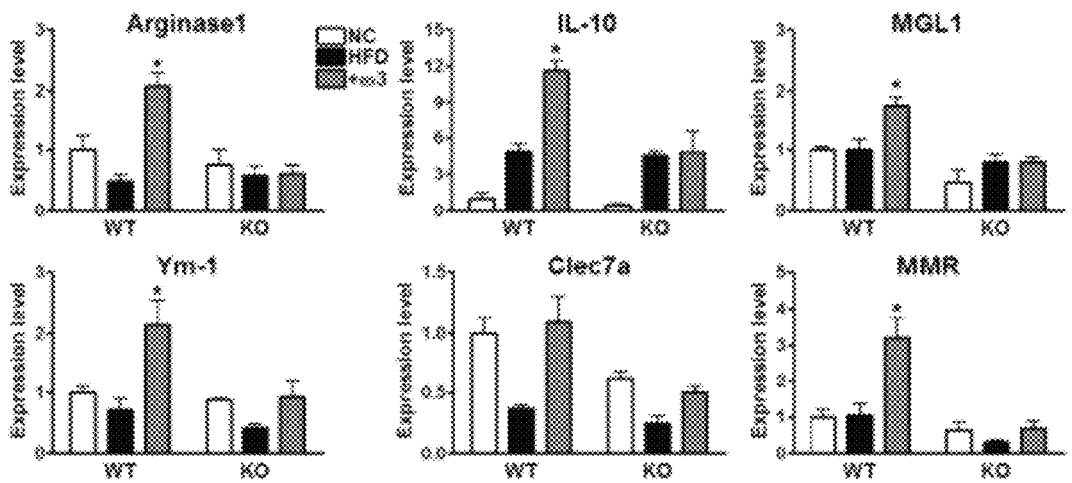
Figure 14A:
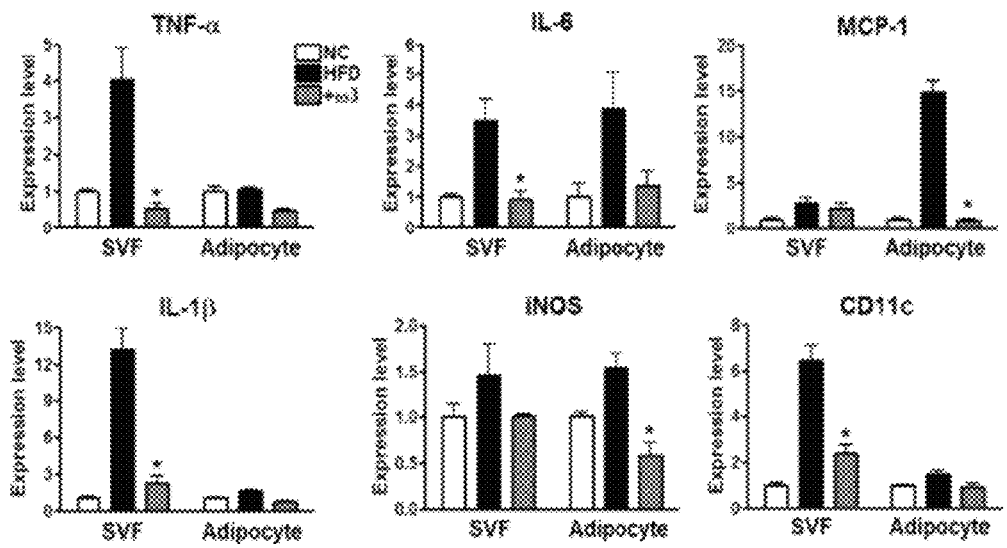
FIG. 14, related to FIG. 7. M1 and M2 inflammatory gene expression levels in the adipocyte and SVC fractions from adipose tissue. Relative mRNA levels for M1 pro-inflammatory genes (A) and M2 anti-inflammatory genes (B) in the adipocytes and SVC fractions from NC, HFD or HFD+ω3 (+ω3)-fed WT mouse adipose tissue, as measured by q-PCR. Data are expressed as mean±SEM of three independent experiments in triplicate. n=5 per group, *, p<0.05 compared to the HFD-fed group. Primer sequences are shown in Table 2.
Figure 14B:
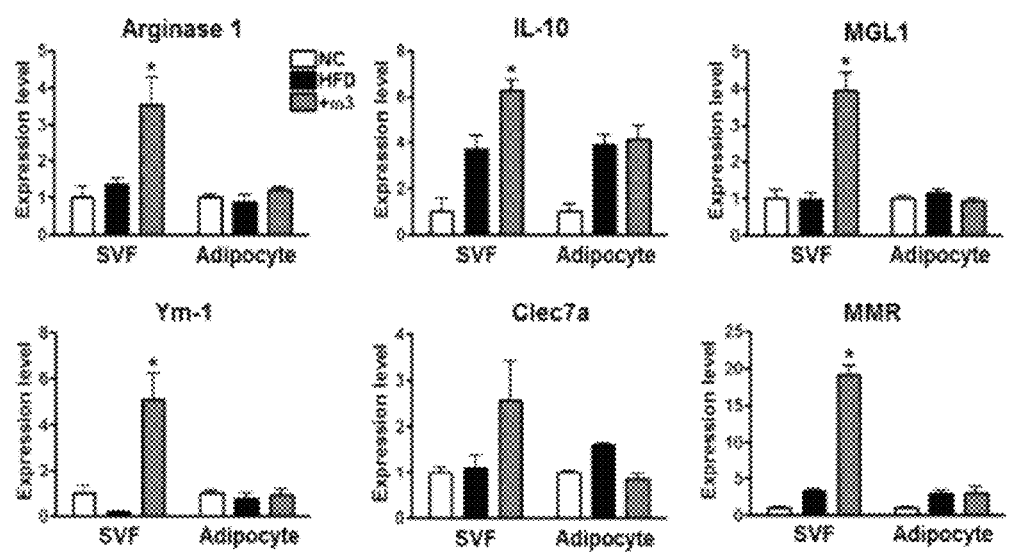

Omega-3 FAs Decrease M1 Pro-Inflammatory Gene and Increase M2 Anti-Inflammatory Gene Expression in Adipose Tissue As shown in FIG. 7A, expression of M1 inflammatory genes such as IL-6, TNF-α, MCP-1, IL-1β, iNOS, and CD11c was increased by HFD compared to chow diet in both genotypes, and was reduced in the ω-3 FA treated WT mice, but not in the GPR120 KO mice. Even on chow diet, expression of several inflammatory genes was higher in GPR120 KOs compared to WT, consistent with the insulin resistance observed in the chow-fed KO mice. Expression of the M2 anti-inflammatory genes, arginase 1, IL-10, MGL1, Ym-1, Clec7a, and MMR was increased by ω-3 FAs in WT, but not in the GPR120 KO adipose tissue (FIG. 7B). These results are consistent with FIG. 6 and demonstrate that the dietary change from HFD to ω-3 FA supplemented HFD resulted in an overall decreased pro-inflammatory profile in adipose tissue from WT, but not in GPR120 KO mice. These changes in gene expression were predominantly manifested in the SVF, except for MCP-1 and IL-6, which are known to be readily expressed in adipocytes (FIG. 14). Qualitatively similar results were seen in the liver (Figs. S6D and S6E).

Example 2

Supplemental Experimental Procedures SiRNA Electroporation siRNAs were obtained from Dharmacon. Sequences for GPR120, β-arrestin1/2, GLUT4 and Gαq/11 siRNA duplexes are available upon request. RAW 264.7 cells and 3T3-L1 adipocytes at day 8 from differentiation protocol were collected and electroporated with siRNAs as described previously (GENE PULSER, Bio-Rad) (Yoshizaki et al., 2009). Further experiments were performed after 48 hr of electroporation.

RNA Isolation, Semi-Quantitative RT-PCR and Quantitative-PCR

Total RNA was isolated using RNeasy columns (Qiagen). First strand cDNA was synthesized using a High-Capacity cDNA Reverse Transcription Kit (Applied Biosystems, Foster City, Calif.). For Semi-quantitative RT-PCR was performed as previously described (Yoshizaki et al., 2009) to measure the levels of lipid sensing GPCRs and RPS3 mRNAs. For quantitative PCR (q-PCR), the samples were run in 20 μl reaction using an MJ Research PTC-200 96-well thermocycler coupled with the Chromo 4 Four-Color Real-Time System (GMI, Inc., Ramsey, Minn.). Gene expression levels were calculated after normalization to the standard housekeeping gene RPS3 and GAPDH using the $\Delta\Delta C_T$ method as described previously (Yoshizaki et al., 2009), and expressed as relative mRNA levels compared with internal control. Primer information is in Table 2:

TABLE 2

| Name | Primer Sequence (5'-3') | SEQ ID NO: |
|---|---|---|
| GPR40 | GCTATTCCTGGGGTGTGTGT | 3 |
|  | CCCTGTGATGAGTCCCAACT | 4 |
| GPR41 | CTGCTCCTGCTCCTCTTC | 5 |
|  | CCAGGCGACTGTAGCAGTA | 6 |
| GPR43 | GGCTCTACAGCAGCATCTA | 7 |
|  | AAGCACACCAGGAAATTAAG | 8 |
| GPR84 | TCCAATTCTGTCTCCATCCT | 9 |
|  | CTGACTGGCTCAGATGAAA | 10 |
| GPR120 | CCATCCCTCTAGTGCTCGTC | 11 |
|  | TGCGGAAGAGTCGGTAGTCT | 12 |
| RPS3 | ATCAGAGAGTTGACCGCAGTTG | 13 |
|  | AATGAACCGAAGCACACCATAG | 14 |
| TNF-α | GCCACCACGCTCTTCTGCCT | 15 |
|  | GGCTGATGGTGTGGGTGAGG | 16 |
| IL-6 | CCAGAGATACAAAGAAATGATGG | 17 |
|  | ACTCCAGAAGACCAGAGGAAAT | 18 |
| MCP-1 | TCTGGACCCATTCCTTCTTG | 19 |
|  | AGGTCCCTGTCATGCTTCTG | 20 |
| IL-1β | AAATACCTGTGGCCTTGGGC | 21 |
|  | CTTGGGATCCACACTCTCCAG | 22 |
| iNOS | AATCTTGGAGCGAGTTGTGG | 23 |
|  | CAGGAAGTAGGTGAGGGCTTG | 24 |
| CD11c | ACGTCAGTACAAGGAGATGTTGGA | 25 |
|  | ATCCTATTGCAGAATGCTTCTTTACC | 26 |
| Arginase 1 | ATGGAAGAGACCTTCAGCTAC | 27 |
|  | GCTGTCTTCCCAAGAGTTGGG | 28 |
| IL-10 | CATGGCCCAGAAATCAAGGA | 29 |
|  | GGAGAAATCGATGACAGCGC | 30 |
| MGL1 | ATGATGTCTGCCAGAGAACC | 31 |
|  | ATCACAGATTTCAGCAACCTTA | 32 |
| Ym-1 | GGGCATACCTTTATCCTGAG | 33 |
|  | CCACTGAAGTCATCCATGTC | 34 |
| Clec7a | AGGTTTTTCTCAGTCTTGCCTTC | 35 |
|  | GGGAGCAGTGTCTCTTACTTCC | 36 |
| MMR | CTCGTGGATCTCCGTGACAC | 37 |
|  | GCAAATGGAGCCGTCTGTGC | 38 |
| G6Pase | GTTGAACCAGTCTCCGACCA | 39 |
|  | CGACTCGCTATCTCCAAGTGA | 40 |
| PEPCK | CTGCATAACGGTCTGGACTTC | 41 |
|  | CAGCAACTGCCCGTACTCC | 42 |
| FAS | GGAGGTGGTGATAGCCGGTAT | 43 |
|  | TGGGTAATCCATAGAGCCCAG | 44 |
| ACC1 | TAATGGGCTGCTTCTGTGACTC | 45 |
|  | CTCAATATCGCCATCAGTCTTG | 46 |
| LXRα | GCTCTGCTCATTGCCATCAG | 47 |
|  | TGTTGCAGCCTCTCTACTTGG | 48 |
| GAPDH | TCACCACCATGGAGAAGGC | 49 |
|  | GCTAAGCAGTTGGTGGTGCA | 50 |

Clec7a, C-type lectin domain family 7, member a; MMR, macrophage mannose receptor.

Cell Culture, Transfection and Luciferase Reporter Assay

Maintenance of HEK 293 and 3T3-L1 cells and differentiation of 3T3-L1 cells were performed as described (Liao et al., 2007). Adipocytes were studied at 10-14 days post-differentiation. RAW 264.7 cells were maintained in 10% low endotoxin fetal bovine serum (Hyclone)/DMEM (1 g/l of glucose). IPMacs were obtained from WT and GPR120 KO mice and cultured as described previously (Nguyen et al., 2007, Patsouris et al., 2009). L6 myoblast cells were maintained in 10% FBS/MEM until cells become confluent, and then changed medium to 2% serum contained MEM to differentiate into myocyte. For transfection of FLAG-tagged serial mutant β-arrestin2 constructs (gift from Dr. Robert Lefkowitz, Duke University), HEK 293 cells were plated in 60 mm culture dish at day before transfection. HA-tagged GPR120 or/and FLAG-tagged β-arrestin2 mutant were transfected using with Effectene reagent (Qiagen, Valencia Calif.) following as manufacturer's instructions. After 48 hr transfection, cells were stimulated with 100 µM DHA for 30 min (for interaction between GPR120 and β-arrestin2) or 1 hr (For endogenous TAB1 and β-arrestin2) before harvested cells subjected to immunoprecipitation and western blotting. For reporter assay, HEK 293 cells were co-transfected with SRE-luc and either mouse GPR120 or pcDNA3 control plasmid (without GPR120) in 24-well plate. Forty-eight hr after transfection, cells were treated with the indicated concentration of various fatty acids for 6 hr. Cells were harvested, and luciferase activities in the cell extracts were measured as previously described (Oh et al., 2005, Fan et al., 2009).

GLUT4 Translocation and 2-Deoxyglucose (2-DOG) Uptake

HA-GLUT4-eGFP expression vector were electroporated into day 8 post differentiated 3T3-L1 adipocytes for monitoring of GLUT4 translocation as previously described (Yoshizaki et al., 2007). For 2-DOG assay, 3T3-L1 adipocytes were pretreated for 30 min with the indicated drug; and stimulated with 3 ng/ml of insulin for 30 min at 37° C. L6 myocytes were pretreated for 30 min with 100 µM DHA and then stimulated with 100 ng/ml of insulin for 30 min. Glucose uptake was measured as previously described (Imamura et al., 1999).

Primary Adipose Tissue Culture

Epididymal fat pads were collected from chow fed WT and GPR120 KO mice, respectively and then mince them by razor blade into smaller pieces (1-2 cubic mm size). The minced tissues were suspended in Hepes-phosphate salt buffer (Hepes, 10 mM, KCl 4 mM, NaCl 125 mM, $KH_2PO_4$ 0.8 mM, $Na_2HPO_4$ 1.3 mM, $MgCl_2$ 1 mM, $CaCl_2$ 1 mM) and briefly centrifuged at 400×g. Supernatant was removed from the bottom with a 20 gauge needle syringe. The floating fat explants were washed once and add the Hepes-phosphate salt buffer as 25% vol/vol (for example, 0.5 ml explants+1.5 ml buffer) to plate desired aliquot into 12-well plate. The fat tissue explants were gently rotated at 37° C. for 30 minutes and then pretreated with or without 100 µM DHA for 30 minutes followed by 100 ng/ml of insulin treatment for 30 min to subject 2-DOG uptake assay. For 2-DOG assay in primary adipose tissue, [3H]-2-DOG (1 µCi/ml) was added for 10 min and then terminate the incubation by adding of 10 µM Cytochalasin B. To digest tissue explants, collagenase (Type I; 5 mg/ml) solution was added to each well and incubated plate for another 30 min. Collagen digested sample were washed once aid resuspended in 1N NaOH. Transfer the rest to a vial and count for radioactivity.

Protein Isolation, Western Blots, and Co-Immunoprecipitation

Proteins from tissues or cell lysates were extracted with radioimmune precipitation buffer in the presence of phosphatase inhibitors and protease inhibitors (Roche Applied Science). Twenty pg of proteins/lane were separated on a 10% polyacrylamide, precast SDS gel (Bio-Rad) followed by transfer on polyvinylidene difluoride membrane (Immobilon, Millipore), and western blotting was performed as described (Nguyen et al., 2005) with indicated antibodies. For immunoprecipitations, lysates were incubated with 1 µg of anti-β-arrestin2, TAK1 antibody (Cell signaling), or GFP antibody (Santa Cruz Biotechnology) overnight at 4° C. and immune complexes precipitated with Protein A/G-conjugated beads (Invitrogen). Beads were washed with PBS and resuspended in sample buffer. Lysates and immune complexes were separated by SDS-PAGE, subjected to western blotting.

Enzyme-Linked Immunosorbent Assays (ELISA)

TNF-α and IL-6 were directly quantified from RAW 264.7 cells with or without GPR120 knockdown, or IPMacs culture medium. Cells were treated with 100 µM GW9508 or DHA for 1 hr prior to treat 100 ng/ml LPS for 6 hr and then collect medium from the cells and subjected to ELISA according to the manufacturer's instructions (BIOSOURCE). For GLP-1 measurement, mouse blood was collected 1 hr after indicated diet feeding. Adequate inhibitors (protease inhibitors and Diprotin A as DPP IV inhibitor) were used while blood was collecting and then subjected to ELISA to the manufacturer's instructions (ALPCO, Salem, N.H.).

Immunocytochemistry for GPR120 Internalization Assay

GPCR internalization assay to detect colocalization with β-arrestin2 GFP was previously reported (Terrillon et al., 2004) Briefly, 48 hr after transfection of hemagglutinin (HA)-tagged GPR120 and β-arrestin2GFP into HEK 293 cells on cover slips, cells were incubated with rabbit polyclonal anti-HA antibody (Stressgen) for 1 hr at 4° C. After three washes at 4° C., cells were treated for 0, 5, and 30 min at 37° C. with DHA and then cells were washed, fixed, and permeabilized before the addition of a secondary antibody conjugated with Rhodamine (Jackson laboratory). Cells were thoroughly washed three times and then mount on the slide. The samples were analyzed by confocal microscopy by using Olympus Fluoview 1000.

Confocal Microscopy of Mouse Adipose Tissue

The method for immunofluorescene study of mouse adipose tissue was followed as described (Lumeng et al., 2008). Briefly, mice were euthanized and slowly perfused by intracardiac injection with 10 ml of 1% paraformaldehyde diluted in PBS. Finger nail sized fat pad samples were excised and blocked for 1 hr in 5% BSA in PBS with gentle rocking at RT. For detection of intracellular antigens, blocking and subsequent incubations were done in 5% BSA in PBS with 0.3% Triton X-100. Primary antibodies were diluted in blocking buffer to 0.5-1 µg/ml and added to fat samples for overnight at 4° C. After three washes, fluorochrome-conjugated secondary antibodies were added for 1 hr at RT. Fat pads were imaged on an inverted confocal microscope (Olympus Fluoview 1000). Anti-mouse antibodies used were against F4/80 and MGL1 (Abcam); Caveolin1 (BD Biosciences).

In Vitro Chemotaxis Assay

In vitro chemotaxis assay was performed as previously described (Patsouris et al., 2009). Briefly, mature 3T3-L1 adipocytes, more than 99% of cells showing large lipids droplets (12 days after differentiation protocol initiation), were used for preparation of conditioned media. Treatment with the 100 µM DHA for 6 hr was performed in serum-free DMEM cultured IPMacs. For the migration per se, 100,000 IPMacs from WT or GPR120 KO mice were used per condition. The IPMacs were placed in the upper chamber of an 8 µm polycarbonate filter (24-transwell format; Corning, Lowell, Mass.), whereas adipocyte conditioned medium or MCP-1 treatment was placed in the lower chamber. After 3 hr of migration, cells were fixed in formalin and stained with 4',6-diamidino-2-phenylindole and observed.

Fluorescence-Activated Cell Sorting (FACS) Analysis of Macrophages of Adipose Stromal Vascular Fraction Epididymal fat pads were weighed, rinsed in phosphate-buffered saline, and then minced in FACS buffer (phosphate-buffered saline plus 1% BSA). Adipocytes and stromal vascular cells were prepared from collagenase digested adipose tissue as described previously (Nguyen et al., 2007). FACS analysis of stromal vascular cells for macrophage content and subtypes were performed as previously described (Nguyen et al., 2007). Estimation of macrophage subsets numbers/g of fat was performed as follows, number of cells=percentage of cells×number of live cells in SVF/mass of fat depot (g). Numbers obtained were subsequently represented as percentage of the highest subsets.

Glucose Tolerance Test and Hyperinsulinemic-Euglycemic Clamp

Glucose tolerance tests (GTT) were performed pre- and post diet in all groups of animals. GTT testing allowed us to determine the effectiveness of insulin to reduce fasting glucose levels as previously described (Hevener et al., 2003, Saberi et al., 2009). Hyperinsulinemic-euglycemic clamps were performed in chronically cannulated mice 5 days after surgery as previously described (Saberi et al., 2009). In brief, following a 6 hr fast, blood glucose was assessed via tail nick, body mass was measured, and the mice were placed in a Lucite restrainer (Braintree Scientific, Braintree, Mass.). A basal blood sample was taken at −60 min and measured plasma insulin and free fatty acids. Equilibrating tracer solution (41.6 µCi$^3$ H/ml at 2 µl/min) was infused intravenously for 60 min. At the end of the equilibration period (t=0 min), 2×15 µl of whole blood was collected, and blood was deproteinized for the assessment of tracer specific activity and basal glucose disposal rate. Following the equilibration period, a cocktail containing 8% BSA, insulin, and tracer was infused at a constant rate (8.0 mU/kg/min and 41.6 µCi/ml at 2.0 µl/min) along with a variable glucose infusion (50% dextrose, 454 mg/ml). Blood glucose was assessed every 10 min for determination of glucose infusion rate. Glucose infusion rate was adjusted until steady-state blood glucose (120 mg/dl, ±5 mg/dl) was achieved. The clamp was terminated when steady-state conditions were maintained for >30 min (~120 min), at which time 2×15 µl of blood was collected for assessment of tracer-specific activity and insulin-stimulated glucose disposal rate (τ=~120 min). At the end of the clamp period, the mouse were exsanguinated by cardiac puncture (≥1 ml, whole blood collected), and tissues were harvested, mass recorded, and preserved as required for future analysis. To examine acute effect of DHA, clamp studies were performed on WT animals on 60% HFD for 15 weeks. On day of clamp, the animals were gavaged with saline or DHA (300 µl, EPAX 1050TG, Aalesund, Norway) 2 hr after fasting. Four hr after gavage, the animals were clamped using 8 mU/kg/min. Saline was used for administered control.

Bone Marrow Transplantation

We have performed bone marrow transplantation (BMT) experiments to ascertain the role of macrophage GPR120 in mediating whole body glucose homeostasis. BMT was performed as described (Lesniewski et al., 2007). Briefly, bone marrow obtained from WT and GPR120 KO mice (~3×10$^6$ cells) was injected through the tail vein into male irradiated (10Gy) C57BL/6 (8 weeks). Mice were allowed 8 weeks for reconstitution of donor marrow, which we verified by q-PCR and then kept the animals on either chow or 60% HFD for 15 weeks. The group on 60% HFD was switched to an isocaloric HFD supplemented with ω3 FAs for 5 weeks, and clamps were performed.

Lipidomics

DHA and EPA concentrations in plasma TG and liver total TAG were measured by Lipomics, Inc. (West Sacramento, Calif.). The lipids were extracted from plasma and tissues in the presence of authentic internal standards using chloroform mixed with methanol (2:1 vol/vol) (Folch et al., 1957) and individual lipid classes were separated by HPLC (Cao et al., 2008). Lipid class fractions were transesterified in 1% sulfuric acid (in methanol) in a sealed vial with nitrogen at 100° C. for 45 min. Fatty acid methyl esters were extracted from the mixture with hexane containing 0.05% butylated hydroxytoluene, and readied for gas chromatography under nitrogen. Finally, fatty acid methyl esters were separated and quantified by capillary gas chromatography equipped with a 30 m DB-88MS capillary column and a flame-ionization detector.

Discussion

In this report we show that GPR120 functions as an ω-3 FA receptor/sensor in pro-inflammatory macrophages and mature adipocytes. By signaling through GPR120, DHA and EPA (the major natural ω-3 FA constituents of fish oil), mediate potent anti-inflammatory effects to inhibit both TLR and TNF-α inflammatory signaling pathways. The mechanism of GPR120-mediated anti-inflammation involves inhibition of TAK1 through a β-arrestin2/TAB1 dependent effect. Since chronic tissue inflammation is an important mechanism causing insulin resistance (Xu et al., 2003', Shoelson et al., 2007, Schenk et al., 2008), the anti-inflammatory actions of ω-3 FAs exert potent insulin sensitizing effects. The in vivo anti-inflammatory and insulin sensitizing effects of ω-3 FAs are dependent on expression of GPR120, as demonstrated in studies of obese GPR120 KO animals and WT littermates. Thus, GPR120 is highly expressed in pro-inflammatory macrophages and functions as an ω-3 FA receptor, mediating the anti-inflammatory effects of this class of FAs to inhibit both the TLR2/3/4 and the TNF-α response pathways and cause systemic insulin sensitization.

GPR120 is a Gαq/11-coupled receptor, and since it is expressed in enteroendocrine L cells, past interest in this receptor has focused on its potential ability to stimulate L cell GLP-1 secretion. In the current study, we show that, in addition to L cells, GPR120 is highly expressed in pro-inflammatory, M1-like macrophages and mature adipocytes, with negligible expression in muscle, pancreatic β-cells, and hepatocytes (Gotoh et al., 2007). In the HFD/obese mouse model, GPR120 expression is highly induced in ATMs as well as resident liver macrophages (Kupffer cells). To explore the biology around GPR120, we established an artificial reporter cell assay and found that the 0ω-3 FAs, DHA, and EPA, are ligands for GPR120, and comparable to the effects of a non-selective GPR120 tool compound (GW9508), the ω-3 FAs exert potent anti-inflammatory effects in macrophages. Our results also revealed the molecular mechanisms underlying these anti-inflammatory effects. Thus, DHA stimulation of GPR120 inhibits both the TLR2/3/4 and TNF-α pro-inflammatory cascade. Since activation of IKKβ and JNK are common to TLR and TNF-α signaling, this indicates that the locus of GPR120 inhibition is at or proximal to these kinases. TAK1 activation stimulates both the IKKβ/NFκB and JNK/AP1 pathways, and the TLR and TNF-α signaling pathways converge at this step. Our data show that stimulation of GPR120 specifically inhibits TAK1 phosphorylation and activation providing a common mechanism for the inhibition of both TLR and TNF-α signaling.

Beta-arrestins can serve as important adaptor and scaffold molecules mediating the functions of a number of different GPCRs, as well as other receptor subtypes (Miller and Lefkowitz, 2001). The C-terminal region of GPR120 contains several putative β-arrestin2 binding motifs ((S/T)X4-5(S/T); Cen et al., 2001), but whether β-arrestins play any role in GPR120 function was unknown. Here we find that activation of GPR120 by DHA stimulation leads to association of the receptor with β-arrestin2, but not β-arrestin1, and that the anti-inflammatory effects of GPR120 are completely β-arrestin2 dependent. Functional immunocytochemical studies showed that DHA stimulation leads to recruitment of β-arrestin2 to the plasma membrane where it co-localizes with GPR120. This is followed by receptor and β-arrestin2 internalization, where the two are now co-localized in the cytoplasmic compartment. TAB1 is the activating protein for TAK1 and our results show that following DHA-stimulated internalization of the GPR120β-arrestin2 complex, β-arrestin2 can now associate with TAB1, as measured in co-immunoprecipitation experiments; only full-length β-arrestin2 was capable of interacting with GPR120 and TAB1. This apparently blocks the association of TAB1 with TAK1, inhibiting TAK1 activation and downstream signaling to the IKKPβ/NFκB and JNK/AP1 system. These results provide a mechanism for the β-arrestin2-mediated inhibition of TLR4, TNF-α, and TLR2/3 action. Other studies in the literature are consistent with these findings, since it has been shown that β-arrestin2 can inhibit NFκB signaling in other systems (Gao et al., 2004, Wang et al., 2006). Furthermore, Lefkowitz group has recently published an extensive proteomics analysis of β-arrestin2 interacting partners, and among the 266 proteins they identified, TAB1 was represented on the list (Xiao et al., 2007).

Figure 11D:
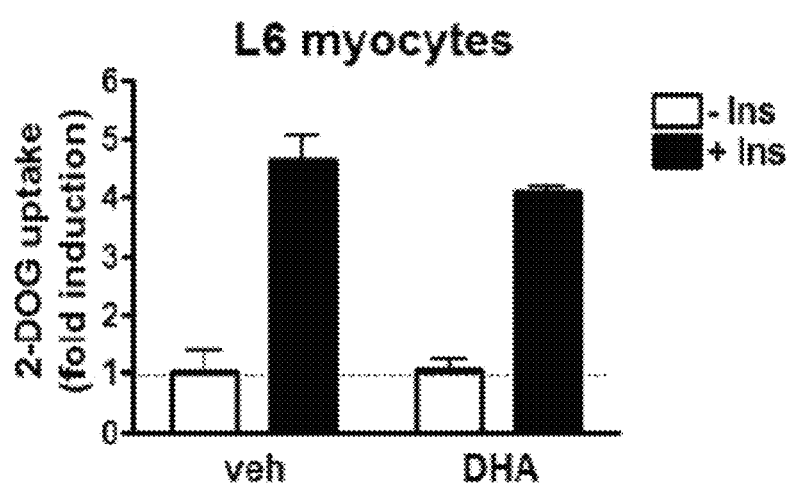
Figure 11E:
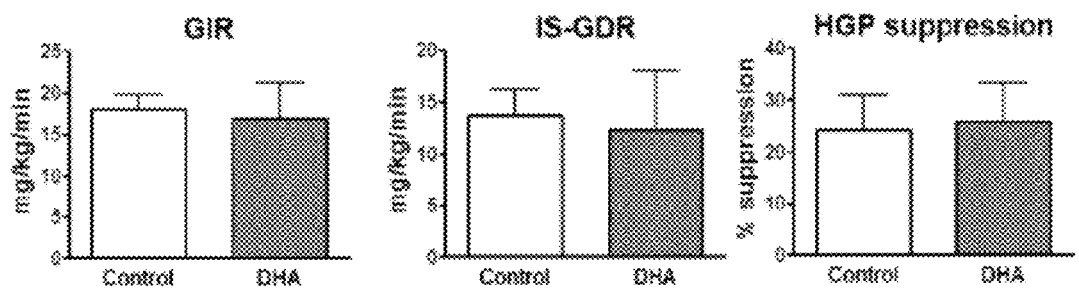
Figure 12A:
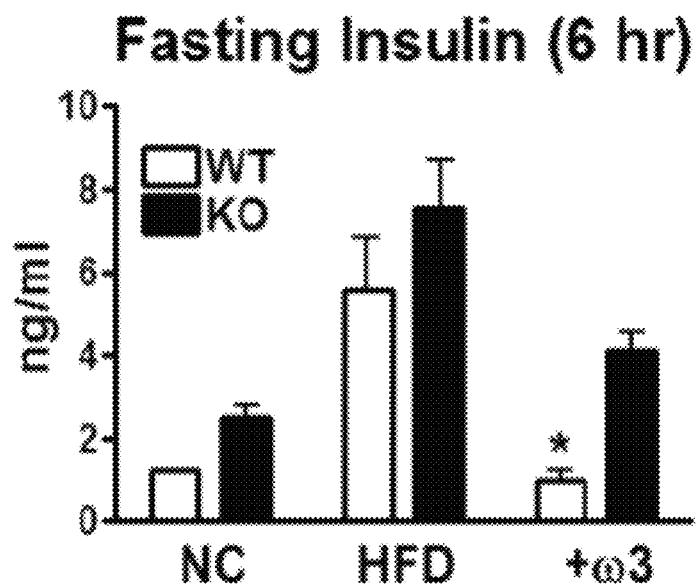
FIG. 12, related to FIG. 5. Measurement of circulating insulin, leptin, triacylglyceride, and GLP-1 levels. Mice on respective diets (n=at least 5 per group) were fasted for 6 hr. Blood was obtained through tail vein and centrifuged to obtain serum and frozen for later analyses of (A) insulin, (B) leptin and (C) TAG. (D) For GLP-1 measurements, blood was obtained from tail vein of animals 1 hr after feeding and centrifuged to obtain serum. ELISA was performed for insulin, leptin and GLP-1. Data are expressed as mean±SEM. TAG was measured by lipidomic analysis as described in the supplemental experimental procedures.
Figure 12B:
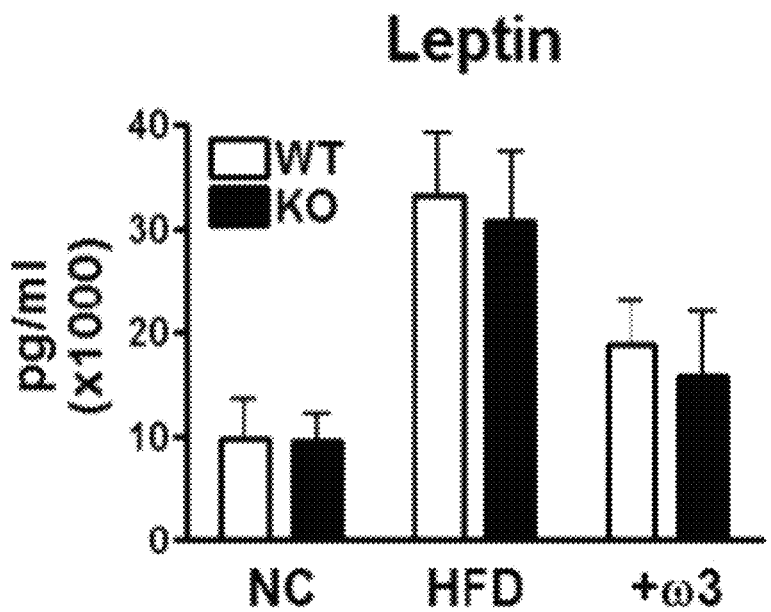
Figure 12C:
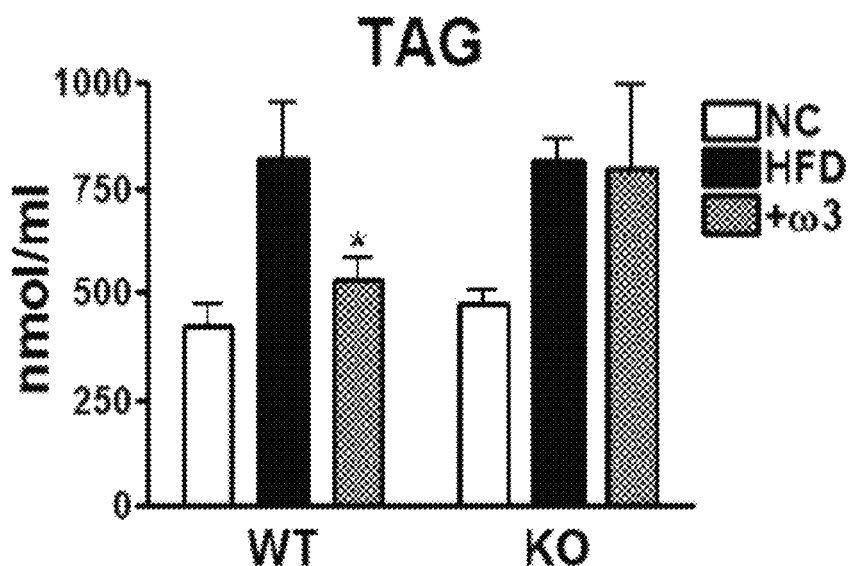
Figure 12D:
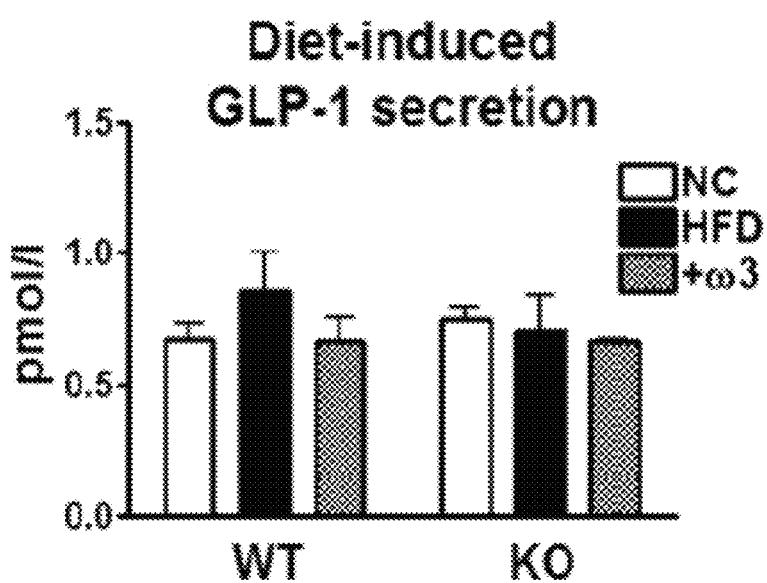

Interestingly, the anti-inflammatory effects mediated by GPR120 were entirely dependent on β-arrestin2, but independent of Gαq/11, despite the fact that GPR120 can be a Gαq/11-coupled receptor in other contexts. This provides further evidence demonstrating the concept that a single GPCR can independently signal through multiple pathways. In previous studies, we have demonstrated that Gαq/11 activation can lead to stimulation of GLUT4 translocation in adipocytes. Since GPR120 was expressed in mature adipocytes, but not preadipocytes, we explored the potential role of GPR120 in glucose transport control. Interestingly, we found that DHA stimulation of GPR120 in 3T3-L1 adipocytes increased GLUT4 translocation to the cell surface with a subsequent increase in glucose transport into the cells. RNA interference studies showed that the DHA effect on glucose uptake was GPR120, GLUT4, and Gαq/11 dependent, but independent of β-arrestin2. This effect was about 30-50% as great as the effect of insulin and the actions of DHA on glucose uptake were additive to those of a submaximally stimulating concentration of insulin. From this, it is possible to propose that these insulinometic effects contribute to the overall insulin sensitizing actions of ω-3 FAs. However, muscle glucose uptake accounts for the great majority (70-80%) of insulin stimulated glucose disposal. Furthermore, GPR120 is not expressed in muscle, and DHA did not stimulated glucose uptake in L6 myocytes (FIGS. 11C and 11D). In addition, acute administration of DHA had no stimulatory effects on IS-GDR (FIG. 11E). This reports the conclusion that the in vivo stimulatory effects of DHA on GDR are related to anti-inflammation, and that the glucose transport stimulatory effects in adipocytes contribute little to the overall phenotype.

Since chronic, low grade tissue inflammation is an important cause of obesity-related insulin resistance, we reasoned that the anti-inflammatory effects of GPR120 stimulation should be coupled to insulin sensitizing actions in vivo. This idea was confirmed in studies of WT and GPR120 KO mice. On a chow diet, the lean GPR120 KO mice were glucose intolerant, hyperinsulinemic and displayed decreased skeletal muscle and hepatic insulin sensitivity, as measured during glucose clamp studies. They also displayed increased ATM content, relative to WT mice, and a 2-5 fold higher expression level of the M1 pro-inflammatory markers, MCP-1, iNOS, and IL-6 (FIG. 7A). On HFD, GPR120 KO and WT mice became equally obese and insulin resistant. Importantly, ω-3 FA supplementation markedly increased insulin sensitivity in WT mice but was without effect in the GPR120 KOs. Consistent with these results, ω-3 FA treatment led to a decrease in ATM accumulation with reduced adipose tissue markers of inflammation in WT, but not in KO mice. In addition to direct anti-inflammatory effects in macrophages, DHA treatment inhibited the ability of primary WT macrophages to migrate towards adipocyte CM. This could be due to DHA-induced decreased chemokine secretion or down regulation of chemokine receptors, or both. In addition, it is possible that DHA, by signaling through GPR120, can mediate heterologous desensitization of other GPCR chemokine receptors. We also observed a concomitant increase in M2 markers, such as IL-10, arginase 1, MGL1, Ym-1, Clec7a, and MMR. This latter finding raises the possibility that ω-3 FAs can redirect ATMs from an M1 to an M2 polarization state. Taken together, these mechanisms account for the decreased inflammatory state. The in vivo anti-inflammatory actions of ω-3 FAs are consistent with the insulin sensitizing effects of these agents and are fully dependent on the presence of GPR120, indicating a causal relationship. Finally, the adoptive transfer studies showed that hematopoietic cell GPR120 deletion results in a comparable insulin resistant, ω-3 FA non-responsive phenotype as seen in the global GPR120 KOs, indicating that this phenotype can be traced back to inflammatory events in macrophages.

We also performed a detailed in vivo lipidomic analysis of FAs in the different lipid classes in the liver (Supplemental Table 2).

TABLE 3

Individual fatty acid content in the various lipid classes (nmol/g of liver sample)

|  | Lipid classes | Palmitic C16:0 | Stearic C18:0 | Palmitoleic C16:1n7 | Oleic C18:1n9 | ☐-Linolenic C18:3n6 | Arachidonic C20:4n6 |
|---|---|---|---|---|---|---|---|
| WT:NC | CE | 1079 ± 318 | 146 ± 22 | 85 ± 23 | 330 ± 114 | 6 ± 3 | 46 ± 7 |
|  | Cardiolipin | 1046 ± 174 | 510 ± 154 | 388 ± 28 | 915 ± 89 | 11 ± 2 | 402 ± 203 |
|  | DAG | 694 ± 98 | 125 ± 30 | 186 ± 4 | 762 ± 180 | 9 ± 3 | 82 ± 31 |
|  | FFA | 910 ± 153 | 293 ± 20 | 112 ± 20 | 530 ± 69 | 7 ± 1 | 115 ± 27 |
|  | LYPC | 600 ± 228 | 171 ± 46 | 40 ± 18 | 156 ± 62 | 5 ± 2 | 58 ± 19 |
|  | PC | 10788 ± 1648 | 3399 ± 927 | 528 ± 85 | 3482 ± 862 | 86 ± 27 | 3229 ± 666 |
|  | PE | 4862 ± 1328 | 5987 ± 1363 | 266 ± 78 | 2054 ± 526 | 19 ± 6 | 6420 ± 1884 |
|  | PS | 616 ± 168 | 1268 ± 250 | 23 ± 7 | 300 ± 62 | 3 ± 1 | 523 ± 172 |
|  | TAG | 9901 ± 2706 | 723 ± 168 | 2366 ± 839 | 14240 ± 3806 | 96 ± 20 | 396 ± 94 |

TABLE 3-continued

Individual fatty acid content in the various lipid classes (nmol/g of liver sample)

| | Lipid classes | Palmitic C16:0 | Stearic C18:0 | Palmitoleic C16:1n7 | Oleic C18:1n9 | □-Linolenic C18:3n6 | Arachidonic C20:4n6 |
|---|---|---|---|---|---|---|---|
| KO:NC | CE | 1702 ± 320 | 176 ± 12 | 93 ± 26 | 276 ± 65 | 2 ± 0.4 | 36 ± 6 |
| | Cardiolipin | 951 ± 125 | 606 ± 117 | 254 ± 44 | 890 ± 148 | 15 ± 1 | 411 ± 52 |
| | DAG | 577 ± 90 | 114 ± 8 | 91 ± 34 | 528 ± 115 | 10 ± 2 | 70 ± 4 |
| | FFA | 833 ± 125 | 254 ± 19 | 64 ± 21 | 339 ± 49 | 7 ± 1 | 77 ± 10 |
| | LYPC | 293 ± 15 | 187 ± 5 | 7 ± 2 | 51 ± 3 | 1 ± 0.3 | 56 ± 5 |
| | PC | 10760 ± 544 | 4490 ± 221 | 345 ± 66 | 2435 ± 109 | 87 ± 12 | 3401 ± 168 |
| | PE | 4346 ± 277 | 6960 ± 556 | 153 ± 25 | 1636 ± 108 | 14 ± 2 | 6273 ± 446 |
| | PS | 902 ± 270 | 1924 ± 235 | 27 ± 9 | 292 ± 67 | 5 ± 2 | 801 ± 130 |
| | TAG | 14337 ± 4492 | 1233 ± 664 | 3227 ± 1275 | 16560 ± 6067 | 224 ± 15 | 586 ± 97 |
| WT:HFD | CE | 1293 ± 98 | 183 ± 11 | 437 ± 87 | 2252 ± 303 | 6 ± 1 | 191 ± 13 |
| | Cardiolipin | 786 ± 66 | 421 ± 32 | 134 ± 21 | 1213 ± 113 | 19 ± 1 | 500 ± 28 |
| | DAG | 1689 ± 403 | 189 ± 23 | 181 ± 45 | 2392 ± 54 | 32 ± 5 | 218 ± 33 |
| | FFA | 971 ± 106 | 182 ± 6 | 83 ± 18 | 965 ± 172 | 13 ± 2 | 238 ± 41 |
| | LYPC | 393 ± 75 | 250 ± 13 | 8 ± 3 | 76 ± 11 | 2 ± 0.2 | 138 ± 6 |
| | PC | 9692 ± 540 | 5410 ± 389 | 176 ± 22 | 2512 ± 180 | 87 ± 9 | 7199 ± 295 |
| | PE | 2156 ± 140 | 4440 ± 333 | 58 ± 9 | 1322 ± 124 | 9 ± 1 | 5658 ± 313 |
| | PS | 392 ± 23 | 1421 ± 116 | 11 ± 2 | 224 ± 19 | 1 ± 0.2 | 1274 ± 105 |
| | TAG | 95051 ± 22995 | 5463 ± 1200 | 12968 ± 3700 | 148220 ± 39008 | 1784 ± 520 | 7221 ± 2125 |
| KO:HFD | CE | 1165 ± 71 | 165 ± 11 | 374 ± 109 | 2048 ± 447 | 7 ± 1 | 212 ± 16 |
| | Cardiolipin | 954 ± 121 | 674 ± 92 | 133 ± 16 | 1311 ± 165 | 23 ± 3 | 786 ± 109 |
| | DAG | 1639 ± 432 | 198 ± 25 | 145 ± 34 | 2192 ± 562 | 31 ± 7 | 220 ± 24 |
| | FFA | 910 ± 57 | 187 ± 13 | 65 ± 4 | 865 ± 62 | 12 ± 1 | 240 ± 20 |
| | LYPC | 390 ± 52 | 263 ± 19 | 6 ± 2 | 76 ± 8 | 2 ± 0.4 | 144 ± 13 |
| | PC | 9224 ± 312 | 5599 ± 444 | 146 ± 9 | 2299 ± 130 | 81 ± 9 | 7588 ± 526 |
| | PE | 1961 ± 29 | 4099 ± 223 | 51 ± 2 | 1194 ± 34 | 9 ± 1 | 5100 ± 154 |
| | PS | 404 ± 9 | 1358 ± 110 | 10 ± 1 | 233 ± 8 | 1 ± 0.2 | 1227 ± 43 |
| | TAG | 92932 ± 28951 | 6421 ± 1735 | 9855 ± 2533 | 144137 ± 49878 | 1707 ± 446 | 7556 ± 2025 |
| WT:+ω3 | CE | 865 ± 82 | 90 ± 11 | 294 ± 53 | 684 ± 60 | 4 ± 1 | 71 ± 12 |
| | Cardiolipin | 1410 ± 294 | 666 ± 78 | 263 ± 55 | 1251 ± 276 | 14 ± 4 | 322 ± 88 |
| | DAG | 875 ± 71 | 123 ± 5 | 125 ± 30 | 935 ± 87 | 8 ± 0.8 | 73 ± 5 |
| | FFA | 854 ± 61 | 150 ± 8 | 67 ± 15 | 418 ± 33 | 4 ± 0.2 | 81 ± 6 |
| | LYPC | 525 ± 34 | 199 ± 12 | 14 ± 3 | 67 ± 3 | 1 ± 0.1 | 66 ± 4 |
| | PC | 13212 ± 412 | 3750 ± 289 | 385 ± 60 | 2178 ± 57 | 38 ± 2 | 2474 ± 210 |
| | PE | 3963 ± 331 | 6397 ± 763 | 152 ± 30 | 1259 ± 31 | 8 ± 0.4 | 3478 ± 415 |
| | PS | 673 ± 17 | 1533 ± 97 | 26 ± 4 | 279 ± 16 | 2 ± 0.3 | 328 ± 28 |
| | TAG | 34899 ± 5385 | 3717 ± 603 | 5067 ± 1297 | 42842 ± 7018 | 469 ± 104 | 1602 ± 385 |
| KO:+ω3 | CE | 974 ± 71 | 112 ± 10 | 462 ± 133 | 1413 ± 500 | 5 ± 0.7 | 85 ± 12 |
| | Cardiolipin | 1376 ± 142 | 1003 ± 147 | 222 ± 24 | 1198 ± 105 | 14 ± 3 | 502 ± 107 |
| | DAG | 1000 ± 239 | 144 ± 17 | 143 ± 46 | 1413 ± 484 | 15 ± 6 | 108 ± 32 |
| | FFA | 839 ± 147 | 152 ± 8 | 71 ± 21 | 590 ± 220 | 5 ± 3 | 82 ± 60 |
| | LYPC | 523 ± 70 | 220 ± 13 | 15 ± 5 | 78 ± 10 | 2 ± 0.3 | 56 ± 20 |
| | PC | 12206 ± 537 | 4190 ± 345 | 320 ± 39 | 2452 ± 218 | 37 ± 13 | 2689 ± 861 |
| | PE | 3818 ± 425 | 7027 ± 719 | 100 ± 17 | 1272 ± 128 | 9 ± 1 | 4123 ± 420 |
| | PS | 630 ± 24 | 1645 ± 106 | 21 ± 4 | 278 ± 41 | 2 ± 0.4 | 648 ± 271 |
| | TAG | 75375 ± 15383 | 6127 ± 768 | 8862 ± 2180 | 113937 ± 31584 | 1302 ± 438 | 4999 ± 1806 |

CE, Cholesterol ester; DAG, diacylglycerol; FFA, free fatty acid; LYPC, lysophosphatidylcholine; PC, phosphatidylcholine; PE, phosphatitylethanolamine; PS, phosphatidylserine; TAG, triacylglycerol The results showed that HFD leads to an increase in total TAGs, DAGs, total SFAs, monounsaturated FAs and ω-6 FAs in WT mice, while all of these lipid changes are ameliorated with ω-3 FA treatment. In the GPR120 KO mice, all of these lipids are elevated on HFD to the same extent as in WT mice, but, ω-3 FA supplementation was either ineffective or much less effective. These results are consistent with the view that the reversal of steatosis/non-alcoholic fatty liver disease (NAFLD) by ω-3 FA treatment is mediated, in large part, by GPR120 and that the GPR120 KO mice are predisposed towards NAFLD even in the context of ω-3 FA supplementation.

Dietary DHA is rapidly esterified into chylomicrons during the process of gastrointestinal absorption, and is also packaged into VLDL triglycerides by the liver. DHA can also be esterified into phospholipids and cholesterol esters associated with circulating lipopoproteins and only a small proportion (~5%) of total plasma DHA is found in the FFA pool. Through the action of lipoprotein lipase bound to the luminal surface of endothelial cells, ω-3 FAs are cleaved from circulating triglycerides where they can act as ligands or be taken up by peripheral tissues (Polozova and Salem Jr., 2007). Recent studies have also indicated that metabolic products derived from ω-3 FAs, such as 17S-hydroxy-DHA, resolvins, and protectins may play a role in the long term resolution of inflammation and this might attenuate insulin resistance in the context of obesity (González-Périz et al., 2009). If this proves to be correct, then this could provide an additional mechanism for long term ω-3 FA-induced anti-inflammatory, insulin sensitizing effects. However, in the current studies, we found that these ω-3 FA derivatives were unable to stimulate GPR120 activation in our reporter cell assay (data not shown), indicating that GPR120 functions as a receptor for ω-3 FAs and not their biochemical products. Resolution of inflammation versus anti-inflammatory actions are distinct processes, and it is certainly possible that the products derived from ω-3 FA metabolism work on the former but not the latter.

In summary, we have found that GPR120 functions as an ω-3 FA receptor/sensor and mediates robust and broad anti-inflammatory effects, particularly in macrophages. After ligand stimulation, GPR120 couples to β-arrestin2 which is followed by receptor endocytosis and inhibition of TAB1- mediated activation of TAK1, providing a mechanism for inhibition of both the TLR and TNF-α pro-inflammatory signaling pathways. Since chronic tissue inflammation is linked to insulin resistance in obesity, we used GPR120 KO mice to demonstrate that ω-3 FAs cause GPR120-mediated anti-inflammatory and insulin sensitizing effects in vivo. Overall, these results strongly argue that anti-inflammatory effects can ameliorate insulin resistance in obesity. Taken together, GPR120 emerges as an important control point in the integration of anti-inflammatory and insulin sensitizing responses, which may prove useful in the future development of new therapeutic approaches for the treatment of insulin resistant diseases.

EXPERIMENTAL PROCEDURES

Chemicals and Reagents

GW9508 was purchased from Tocris bioscience (Ellisville, Mo.) and DHA was from Cayman chemical (Ann Arbor, Mich.). All other chemicals were purchased from Sigma unless mentioned otherwise.

Animal Care and Use

Male C57Bl/6 or GPR120 KO littermates were fed a normal chow (13.5% fat; LabDiet) or high-fat diet (60% fat; Research Diet) ad libitum for 15-20 weeks from 8 weeks of age. GPR120 KO mice and WT littermates were provided by Taconic Inc. (Hudson, N.Y.). After weeks on HFD, WT and GPR120 KO mice were switched to an isocaloric HFD-containing 27% menhaden fish oil replacement (wt/wt; menhaden fish oil: 16% EPA (C20:5n3), 9%, DHA (C22:6n3), Research Diet) (Jucker et al., 1999, Neschen et al., 2007) and fed for 5 weeks. Mice received fresh diet every 3rd day, and food consumption and body weight were monitored. Animals were housed in a specific pathogen-free facility and given free access to food and water. All procedures were approved by the University of California San Diego animal care and use committee. In vivo metabolic studies were performed as described under supplemental experimental procedures.

Data Analysis

Densitometric quantification and normalization were performed using the ImageJ 1.42q software. The values presented are expressed as the means±SEM. The statistical significance of the differences between various treatments was determined by one-way ANOVA with the Bonferroni correction using GraphPad Prism 4.0 (San Diego, Calif.). The $p<0.05$ was considered significant.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing descriptions which do not depart from the spirit or scope of the present inventive discovery. Such modifications are also intended to fall within the scope of the appended claims.

REFERENCES

1. Specifically intended to be within the scope of the present invention, and incorporated herein by reference in its entirety, is the following publication: Oh, D. et al., GPR120 Is an Omega-3 Fatty Acid Receptor Mediating Potent Anti-inflammatory and Insulin-Sensitizing Effects. Cell, 2010; 142 (5): 687-698. Other publications incorporated herein by reference in their entirety include:
2. Barak, L. S., Ferguson, S. S., Zhang, J., and Caron, M. G. (1997). A beta-arrestin/green fluorescent protein biosensor for detecting G protein-coupled receptor activation. J Biol Chem 272, 27497-27500.
3. Baron, A. D., Brechtel, G., Wallace, P., and Edelman, S. V. (1988). Rates and tissue sites of non-insulin- and insulin-mediated glucose uptake in humans. Am J Physiol 255, E769-774.
4. Briscoe, C. P., Peat, A. J., McKeown, S. C., Corbett, D. F., Goetz, A. S., Littleton, T. R., McCoy, D. C., Kenakin, T. P., Andrews, J. L., Ammala, C., et al. (2006). Pharmacological regulation of insulin secretion in MIN6 cells through the fatty acid receptor GPR40: identification of agonist and antagonist small molecules. Br J Pharmacol 148, 619-628.
5. Buettner, R., Parhofer, K. G., Woenckhaus, M., Wrede, C. E., Kunz-Schughart, L. A., Scholmerich, J., and Bollheimer, L. C. (2006). Defining high-fat-diet rat models: metabolic and molecular effects of different fat types. J Mol Endocrinol 36, 485-501.
6. Calder, P. C. (2005). Polyunsaturated fatty acids and inflammation. Biochem Soc Trans 33, 423-427.
7. Cen, B., Xiong, Y., Ma, L., and Pêi, G. (2001). Direct and differential interaction of beta-arrestins with the intracellular domains of different opioid receptors. Mol Pharmacol 59, 758-764.
8. Gao, H., Sun, Y., Wu, Y., Luan, B., Wang, Y., Qu, B., and Pei, G. (2004). Identification of beta-arrestin2 as a G protein-coupled receptor-stimulated regulator of NF-kappaB pathways. Mol Cell 14, 303-317.
9. Gether, U. (2000). Uncovering molecular mechanisms involved in activation of G protein-coupled receptors. Endocr Rev 21, 90-113.
10. Gonzalez-Periz, A., Horrillo, R., Ferre, N., Gronert, K., Dong, B., Moran-Salvador, E., Titos, E., Martinez-Clemente, M., Lopez-Parra, M., Arroyo, V., and Claria, J. (2009). Obesity-induced insulin resistance and hepatic steatosis are alleviated by omega-3 fatty acids: a role for resolvins and protectins. Faseb J 23, 1946-1957.
11. Gotoh, C., Hong, Y. H., Iga, T., Hishikawa, D., Suzuki, Y., Song, S. H., Choi, K. C., Adachi, T., Hirasawa, A., Tsujimoto, G., et al. (2007). The regulation of adipogenesis through GPR120. Biochem Biophys Res Commun 354, 591-597.
12. Hirasawa, A., Tsumaya, K., Awaji, T., Katsuma, S., Adachi, T., Yamada, M., Sugimoto, Y., Miyazaki, S., and Tsujimoto, G. (2005). Free fatty acids regulate gut incretin glucagon-like peptide-1 secretion through GPR120. Nat Med 11, 90-94.
13. Imamura, T., Vollenweider, P., Egawa, K., Clodi, M., Ishibashi, K., Nakashima, N., Ugi, S., Adams, J. W., Brown, J. H., and Olefsky, J. M. (1999). G alpha-q/11 protein plays a key role in insulin-induced glucose transport in 3T3-L1 adipocytes. Mol Cell Biol 19, 6765-6774.
14. Itoh, Y., Kawamata, Y., Harada, M., Kobayashi, M., Fujii, R., Fukusumi, S., Ogi, K., Hosoya, M., Tanaka, Y., Uejima, H., et al. (2003). Free fatty acids regulate insulin secretion from pancreatic beta cells through GPR40. Nature 422, 173-176.
15. Jucker, B. M., Cline, G. W., Banicci, N., and Shulman, G. I. (1999). Differential effects of safflower oil versus fish oil feeding on insulin-stimulated glycogen synthesis, glycolysis, and pyruvate dehydrogenase flux in skeletal muscle: a 13C nuclear magnetic resonance study. Diabetes 48, 134-140.
16. Kawai, T., and Akira, S. (2006). TLR signaling. Cell Death Differ 13, 816-825.
17. Lee, J. Y., Plakidas, A., Lee, W. H., Heikkinen, A., Chanmugam, P., Bray, G., and Hwang, D. H. (2003). Differential modulation of Toll-like receptors by fatty acids: preferential inhibition by n-3 polyunsaturated fatty acids. J Lipid Res 44, 479-486.
18. Lumeng, C. N., DelProposto, J. B., Westcott, D. J., and Saltiel, A. R. (2008). Phenotypic switching of adipose tissue macrophages with obesity is generated by spatiotemporal differences in macrophage subtypes. Diabetes 57, 3239-3246.
19. Luttrell, L. M., Ferguson, S. S., Daaka, Y., Miller, W. E., Maudsley, S., Della Rocca, G. J., Lin, F., Kawakatsu, H., Owada, K., Luttrell, D. K., et al. (1999). Beta-arrestin-dependent formation of beta2 adrenergic receptor-Src protein kinase complexes. Science 283, 655-661.
20. Luttrell, L. M., and Lefkowitz, R. J. (2002). The role of beta-arrestins in the termination and transduction of G-protein-coupled receptor signals. J Cell Sci 115, 455-465.
21. Miller, W. E., and Lefkowitz, R. J. (2001). Expanding roles for beta-arrestins as scaffolds and adapters in GPCR signaling and trafficking. Curr Opin Cell Biol 13, 139-145.
22. Neschen, S., Morino, K., Dong, J., Wang-Fischer, Y., Cline, G. W., Romanelli, A. J., Rossbacher, J. C., Moore, I. K., Regittnig, W., Munoz, D. S., et al. (2007). n-3 Fatty acids preserve insulin sensitivity in vivo in a peroxisome proliferator-activated receptor-alpha-dependent manner. Diabetes 56, 1034-1041.
23. Nguyen, M. T., Favelyukis, S., Nguyen, A. K., Reichart, D., Scott, P. A., Jenn, A., Liu-Bryan, R:, Glass, C. K., Neels, J. G., and Olefsky, J. M. (2007). A subpopulation of macrophages infiltrates hypertrophic adipose tissue and is activated by free fatty acids via Toll-like receptors 2 and 4 and JNK-dependent pathways. J Biol Chem 282, 35279-35292.
24. Oh, D. Y., Song, J. A., Moon, J. S., Moon, M. J., Kim, J. I., Kim, K., Kwon, H. B., and Seong, J. Y. (2005). Membrane-proximal region of the carboxyl terminus of the gonadotropin-releasing hormone receptor (GnRHR) confers differential signal transduction between mammalian and nonmammalian GnRHRs. Mol Endocrinol 19, 722-731.
25. Polozova, A., and Salem, N., Jr. (2007). Role of liver and plasma lipoproteins in selective transport of n-3 fatty acids to tissues: a comparative study of 14C-DHA and 3H-oleic acid tracers. J Mol Neurosci 33, 56-66.
26. Schenk, S., Saberi, M., and Olefsky, J. M. (2008). Insulin sensitivity: modulation by nutrients and inflammation. J Clin Invest 118, 2992-3002.
27. Shoelson, S. E., Herrero, L., and Naaz, A. (2007). Obesity, inflammation, and insulin resistance. Gastroenterology 132, 2169-2180.
28. Solinas, G., Vilcu, C., Neels, J. G., Bandyopadhyay, G. K., Luo, J. L., Naugler, W., Grivennikov, S., Wynshaw-Boris, A., Scadeng, M., Olefsky, J. M., and Karin, M. (2007). JNK in hematopoietically derived cells contributes to diet-induced inflammation and insulin resistance without affecting obesity. Cell Metab 6, 386-397.
29. Takaesu, G., Surabhi, R. M., Park, K. J., Ninomiya-Tsuji, J., Matsumoto, K., and Gaynor, R. B. (2003). TAK1 is critical for IkappaB kinase-mediated activation of the NF-kappaB pathway. J Mol Biol 326, 105-115.
30. Tazoe, H., Otomo, Y., Kaji, I., Tanaka, R., Karaki, S. I., and Kuwahara, A. (2008). Roles of short-chain fatty acids receptors, GPR41 and GPR43 on colonic functions. J Physiol Pharmacol 59 Suppl 2, 251-262.
31. Ulloa-Aguirre, A., Stanislaus, D., Janovick, J. A., and Conn, P. M. (1999). Structure-activity relationships of G protein-coupled receptors. Arch Med Res 30, 420-435.
32. Wang, J., Wu, X., Simonavicius, N., Tian, H., and Ling, L. (2006). Medium-chain fatty acids as ligands for orphan G protein-coupled receptor GPR84. J Biol Chem 281, 34457-34464.
33. Wang, Y., Tang, Y., Teng, L., Wu, Y., Zhao, X., and Pei, G. (2006). Association of beta-arrestin and TRAF6 negatively regulates Toll-like receptor-interleukin I receptor signaling. Nat Immunol 7, 139-147.
34. Weisberg, S. P., McCann, D., Desai, M., Rosenbaum, M., Leibel, R. L., and Ferrante, A. W., Jr. (2003). Obesity is associated with macrophage accumulation in adipose tissue. J Clin Invest 112, 1796-1808.
35. Xiao, K., McClatchy, D. B., Shukla, A. K., Zhao, Y., Chen, M., Shenoy, S. K., Yates, J. R., 3rd, and Lefkowitz, R. J. (2007). Functional specialization of beta-arrestin interactions revealed by proteomic analysis. Proc Natl Acad Sci USA 104, 12011-12016.
36. Xu, H., Barnes, G. T., Yang, Q., Tan, G., Yang, D., Chou, C. J., Sole, J., Nichols, A., Ross, J. S., Tartaglia, L. A., and Chen, H. (2003). Chronic inflammation in fat plays a crucial role in the development of obesity-related insulin resistance. J Clin invest 112, 1821-1830.
37. Cao, H., Gerhold, K., Mayers, J. R., Wiest, M. M., Watkins, S. M., and Hotamisligil, G. S. (2008). Identification of a lipokine, a lipid hormone linking adipose tissue to systemic metabolism. Cell 134, 933-944.
38. Fan, W., Imamura, T., Sonoda, N., Sears, D. D., Patsouris, D., Kim, J. J., and Olefsky, J. M. (2009). FOXO1 transrepresses peroxisome proliferator-activated receptor gamma transactivation, coordinating an insulin-induced feed-forward response in adipocytes. J Biol Chem 284, 12188-12197.
39. Folch, J., Lees, M., and Sloane Stanley, G. H. (1957). A simple method for the isolation and purification of total lipides from animal tissues. J Biol Chem 226, 497-509.
40. Hevener, A. L., He, W., Barak, Y., Le, J., Bandyopadhyay, G., Olson, P., Wilkes, J., Evans, R. M., and Olefsky, J. (2003). Muscle-specific Pparg deletion causes insulin resistance. Nat Med 9, 1491-1497.
41. Lesniewski, L. A., Hosch, S. E., Neels, J. G., de Luca, C., Pashmforoush, M., Lumeng, C. N., Chiang, S. H., Scadeng, M., Saltiel, A. R., and Olefsky, J. M. (2007). Bone marrow-specific Cap gene deletion protects against high-fat diet-induced insulin resistance. Nat Med 13, 455-462.
42. Liao, W., Nguyen, M. T., Yoshizaki, T., Favelyukis, S., Patsouris, D., Imamura, T., Verma, I. M., and Olefsky, J. M. (2007). Suppression of PPAR-gamma attenuates insulin-stimulated glucose uptake by affecting both GLUT1 and GLUT4 in 3T3-L1 adipocytes. Am J Physiol Endocrinol Metab 293, E219-227.
43. Nguyen, M. T., Satoh, H., Favelyukis, S., Babendure, J. L., Imamura, T., Sbodio, J. I., Zalevsky, J., Dahiyat, B. I., Chi, N. W., and Olefsky, J. M. (2005). JNK and tumor necrosis factor-alpha mediate free fatty acid-induced insulin resistance in 3T3-L1 adipocytes. J Biol Chem 280, 35361-35371.
44. Patsouris, D., Neels, J. G., Fan, W., Li, P. P., Nguyen, M. T., and Olefsky, J. M. (2009). Glucocorticoids and thiazolidinediones interfere with adipocyte-mediated macrophage chemotaxis and recruitment. J Biol Chem 284, 31223-31235.

45. Saberi, M., Woods, N. B., de Luca, C., Schenk, S., Lu, J. C., Bandyopadhyay, G., Verma, I. M., and Olefsky, J. M. (2009). Hematopoietic cell-specific deletion of toll-like receptor 4 ameliorates hepatic and adipose tissue insulin resistance in high-fat-fed mice. Cell Metab 10, 419-429.
46. Terrillon, S., Barberis, C., and Bouvier, M. (2004). Heterodimerization of V1a and V2 vasopressin receptors determines the interaction with beta-arrestin and their trafficking patterns. Proc Natl Acad Sci USA 101, 1548-1553.
47. Yoshizaki, T., Imamura, T., Babendure, J. L., Lu, J. C., Sonoda, N., and Olefsky, J. M. (2007). Myosin 5a is an insulin-stimulated Akt2 (protein kinase Bbeta) substrate modulating GLUT4 vesicle translocation. Mol Cell Biol 27, 5172-5183.
48. Yoshizaki, T., Milne, J. C., Imamura, T., Schenk, S., Sonoda, N., Babendure, J. L., Lu, J. C., Smith, J. J., Jirousek, M. R., and Olefsky, J. M. (2009). SIRT1 exerts anti-inflammatory effects and improves insulin sensitivity in adipocytes. Mol Cell Biol 29, 1363-1374.
49. Citation of a reference herein shall not be construed as an admission that such is prior art to the present invention.

What is claimed is:

1. A method of treating inflammation in a subject, the method comprising administering a therapeutically effective amount of a compound that binds GPR120, the compound selectively activating a β-arrestin2-dependent signaling pathway of GPR120.

2. The method of claim 1, wherein the compound that selectively activates a β-arrestin2-dependent signaling pathway is an ω-3 fatty acid.

3. The method of claim 2, wherein the ω-3 FA is DHA.

4. The method of claim 2, wherein the ω-3 FA is EPA.

5. The method of claim 1, wherein the compound selectively activates a β-arrestin2-dependent signaling pathway and does not activate a β-arrestin1-dependent signaling pathway.

6. The method of claim 1, wherein the inflammation is associated with diabetes.

7. The method of claim 1, wherein the inflammation is associated with obesity.

8. The method of claim 1, wherein the subject is a human.

9. A method of treating an inflammatory condition associated with β-arrestin2 function, the method comprising administering a therapeutically effective amount of a β-arrestin2 modulating agent to a subject in need thereof.

10. The method of claim 9, wherein the inflammatory condition is diabetes.

11. The method of claim 9, wherein the inflammatory condition is associated with obesity.

12. The method of claim 9, wherein the β-arrestin2 modulating agent is an ω-3 fatty acid.

13. The method of claim 9, wherein the ω-3 fatty acid is DHA.

14. The method of claim 9, wherein the ω-3 fatty acid is EPA.

15. The method of claim 9, wherein the compound selectively activates a β-arrestin2-dependent signaling pathway and does not activate a β-arrestin2-dependent signaling pathway.

16. The method of claim 9, wherein the subject is a human.

* * * * *